US012758630B2

(12) United States Patent
Hammond et al.

(10) Patent No.: US 12,758,630 B2
(45) Date of Patent: *Oct. 13, 2026

(54) RIBONUCLEOPROTEIN APPROACH TO BOOST THE STING SIGNALING FOR CANCER IMMUNOTHERAPY

(71) Applicant: MASSACHUSETTS INSTITUTE OF TECHNOLOGY, Cambridge, MA (US)

(72) Inventors: Paula Hammond, Newton, MA (US); Yanpu He, Cambridge, MA (US); Jiahe Li, Medford, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 747 days.

This patent is subject to a terminal disclaimer.

(21) Appl. No.: 18/001,161

(22) PCT Filed: Jun. 11, 2021

(86) PCT No.: PCT/US2021/037023

§ 371 (c)(1),
(2) Date: Dec. 8, 2022

(87) PCT Pub. No.: WO2021/252904

PCT Pub. Date: Dec. 16, 2021

(65) Prior Publication Data

US 2023/0210968 A1 Jul. 6, 2023

Related U.S. Application Data

(60) Provisional application No. 63/037,854, filed on Jun. 11, 2020.

(51) Int. Cl.
*A61K 39/39* (2006.01)
*A61K 39/00* (2006.01)

(52) U.S. Cl.
CPC .......... *A61K 39/39* (2013.01); *A61K 39/0011* (2013.01)

(58) Field of Classification Search
None
See application file for complete search history.

(56) References Cited

U.S. PATENT DOCUMENTS

| | | | | |
|---|---|---|---|---|
| 5,646,285 | A | 7/1997 | Baindur et al. | |
| 5,667,992 | A * | 9/1997 | Casey | C07K 14/005 435/69.3 |
| 10,011,630 | B2 | 7/2018 | Vernejoul et al. | |
| 10,246,480 | B2 | 4/2019 | Kim et al. | |
| 2003/0138413 | A1 * | 7/2003 | Vicari | A61K 47/6891 435/372 |
| 2011/0293637 | A1 | 12/2011 | Hacohen et al. | |
| 2021/0277077 | A1 | 9/2021 | Li | |
| 2023/0331795 | A1 | 10/2023 | Belcher et al. | |

FOREIGN PATENT DOCUMENTS

| | | | | |
|---|---|---|---|---|
| WO | 1991019735 | A1 | 12/1991 | |
| WO | 2006132969 | A1 | 12/2006 | |
| WO | WO-2018138684 | A1 * | 8/2018 | A61P 35/00 |
| WO | WO-2019092660 | A1 * | 5/2019 | C07H 21/02 |
| WO | 2019148037 | A1 | 8/2019 | |
| WO | 2021252904 | A1 | 12/2021 | |

OTHER PUBLICATIONS

Shang, Mar. 2019, Nature, vol. 567: 389-393.*
Weber, 1999, Science, vol. 243: pp. 85-88.*
Accession AVQ94753.1, Apr. 2018.*
Kennedy, R.B. et al. Polymorphisms in STING Affect Human Innate Immune Responses to Poxviruses. Frontiers in Immunology 11, 567348 (2020).
Kierkegaard et al., “Predictive and Prognostic Values of Cancer-Associated Serum Antigen (CASA) and Cancer Antigen 125 (CA 125) Levels Prior to Second-Look Laparotomy for Ovarian Cancer” 1995, Gynecol. Oncol. 59: 251-254.
Kievit et al., “Determination of tumor-related factors of influence on the uptake of the monoclonal antibody 323/A3 in experimental human ovarian cancer” 1997, Int. J. Cancer 71: 237-245.
Kim, H.-J. & Cantor, H. CD4 T-cell Subsets and Tumor Immunity: The Helpful and the Not-so-Helpful. Cancer Immunology Research 2, 91-98 (2014).
Kim, S.-H., Han, C., Kwon, B.S. & Choi, B.K. CD4 depletion potentiates anti-tumor immunity in adoptive immunotherapy by increasing IL-18Rahi endogenous CD8+ T cells. Am Assoc Immnol; 2020.
Kiniwa, T. et al. NK cells activated by Interleukin-4 in cooperation with Interleukin-15 exhibit distinctive characteristics. Proceedings of the National Academy of Sciences 113, 10139-10144 (2016).
Kocabas, B.B. et al. Dual-adjuvant effect of pH-sensitive liposomes loaded with STING and TLR9 agonists regress tumor development by enhancing Th1 immune response. Journal of Controlled Release 328, 587-595 (2020).
Kuhl, N. et al. STING agonism turns human T cells into interferon-producing cells but impedes their functionality. EMBO reports, e55536 (2023).

(Continued)

*Primary Examiner* — Amy E Juedes
(74) *Attorney, Agent, or Firm* — McDonnell Boehnen Hulbert & Berghoff LLP

(57) ABSTRACT

Disclosed herein is a non-covalent complex, comprising: a tetramer of a recombinant protein; and an agonist of a Stimulator of Interferon Gene (STING) protein or a pharmaceutically acceptable salt thereof, wherein the recombinant protein comprises a STING protein lacking a transmembrane domain (STINGΔTM protein). Additionally, provided is a vaccine composition, comprising a non-covalent complex and a pharmaceutically acceptable carrier, wherein the non-covalent complex comprises: a recombinant protein comprising a STINGΔTM protein and a tumor epitope; and an agonist of a STING protein or a pharmaceutically acceptable salt thereof. Further provided are methods of treating and preventing cancer using the disclosed complexes, pharmaceutical compositions, and vaccines.

16 Claims, 43 Drawing Sheets

Specification includes a Sequence Listing.

(56) References Cited

OTHER PUBLICATIONS

Kumamoto, Y., Mattei, L.M., Sellers, S., Payne, G.W. & Iwasaki, A. CD4+ T cells support cytotoxic T lymphocyte priming by controlling lymph node input. Proceedings of the National Academy of Sciences of the United States of America 108, 8749-8754 (2011).
LaFleur et al., "Monoclonal antibody therapeutics with up to five specificities: functional enhancement through fusion of target-specific peptides" MAbs. (Mar.-Apr. 2013) 5(2):208-18.
Laidlaw, B.J., Craft, J.E. & Kaech, S.M. The multifaceted role of CD4+ T cells in CD8+ T cell memory. Nature Reviews Immunology 16, 102-111 (2016).
Larkin, J. et al. Combined Nivolumab and Ipilimumab or Monotherapy in Untreated Melanoma. New England Journal of Medicine 373, 23-34 (2015).
Lee, J. et al. The Multifaceted Role of Th1, Th9, and Th17 Cells in Immune Checkpoint Inhibition Therapy. Frontiers in Immunology 12 (2021).
Li, Y. et al. Prebiotic-induced anti-tumor immunity attenuates tumor growth. Cell reports 30, 1753-1766. e1756 (2020).
Li, Y. et al. Multifunctional oncolytic nanoparticles deliver self-replicating IL-12 RNA to eliminate established tumors and prime systemic immunity. Nature Cancer 1, 882-893 (2020).
Li, K. et al. The lipid platform increases the activity of STING agonists to synergize checkpoint blockade therapy against melanoma. Biomaterials science 9, 765-773 (2021).
Lin, Y., Xu, J. & Lan, H. Tumor-associated macrophages in tumor metastasis: biological roles and clinical therapeutic applications. Journal of Hematology & Oncology 12, 76 (2019).
LLC, M.S.D. Study of Ulevostinag (MK-1454) Alone or in Combination With Pembrolizumab (MK-3475) in Participants With Advanced/Metastatic Solid Tumors or Lymphomas (MK-1454-001). https://beta.clinicaltrials.gov/study/NCT03010176 (Accessed May 10, 2023).
Lozza et al., "Cancer of the uterine cervix: clinical value of squamous cell carcinoma antigen (SCC) measurements" 1997 Anticancer Res. 17: 525-529.
Lu, L. et al. Clinically approved combination immunotherapy: Current status, limitations, and future perspective. Current Research in Immunology 3, 118-127 (2022).
Luan, Y.-y., Zhang, L., Peng, Y.-q., Li, Y.-y. & Yin, C.-h. STING modulates necrotic cell death in CD4 T cells via activation of PARP-1/PAR following acute systemic inflammation. International Immunopharmacology 109, 108809 (2022).
Maes, H., Taper, H. & Cocito, C. Comparison between bacillus Calmette-Guérin and the A60 mycobacterial antigen complex used as cancer-preventive immunotherapies. J Cancer Res Clin Oncol 122, 296-300 (1996).
Marabelle, A., Tselikas, L., de Baere, T. & Houot, R. Intratumoral immunotherapy: using the tumor as the remedy. Annals of Oncology 28, xii33-xii43 (2017).
Marcus, A. et al. Tumor-derived cGAMP triggers a STING-mediated interferon response in non-tumor cells to activate the NK cell response. Immunity 49, 754-763. e754 (2018).
Melero, I., Castanon, E., Alvarez, M., Champiat, S. & Marabelle, A. Intratumoural administration and tumour tissue targeting of cancer immunotherapies. Nature Reviews Clinical Oncology 18, 558-576 (2021).
Meric-Bernstam, F. et al. Phase Ib study of MIW815 (ADU-S100) in combination with spartalizumab (PDR001) in patients (pts) with advanced/metastatic solid tumors or lymphomas. Journal of Clinical Oncology 37, 2507-2507 (2019).
Mersana Therapeutics, I. Mersana Therapeutics Announces FDA Grant of Orphan Drug Designation to XMT-2056 for the Treatment of Gastric Cancer. 2022.
Molldrem J, Dermime S, Parker K, Jiang YZ, Mavroudis D, Hensel N, Fukushima P, Barrett J. Targeted T-cell therapy for human leukaemia: cytotoxic T lymphocytes specific for a peptide derived from proteinase 3 preferentially lyse human myeloid leukemia cells. Blood 1996; 88:2450-7.
Molldrem JJ, Clave E, Jiang YZ, et al. Cytotoxic T lymphocytes specific for a nonpolymorphic proteinase 3 peptide preferentially inhibit chronic myeloid leukemia colony-forming units. Blood. (1997) 90(7):2529-2534.
Mota et al., "Cathepsin E expression by normal and premalignant cervical epithelium" 1997, Am. J Pathol. 150(4): 1223-1229.
Motedayen Aval, L., Pease, J.E., Sharma, R. & Pinato, D.J. Challenges and Opportunities in the Clinical Development of STING Agonists for Cancer Immunotherapy. Journal of clinical medicine 9 (2020).
Moynihan, K.D. et al. Eradication of large established tumors in mice by combination immunotherapy that engages Innate and adaptive immune responses. Nature medicine 22, 1402-1410 (2016).
Nagai, H. et al. Elimination of CD4+ T cells enhances anti-tumor effect of locally secreted interleukin-12 on B16 mouse melanoma and induces vitiligo-like coat color alteration. Journal of investigative dermatology 115, 1059-1064 (2000).
Nicolai, C.J. et al. NK cells mediate clearance of CD8+ T cell-resistant tumors in response to STING agonists. Science Immunology 5, eaaz2738 (2020).
Nishino, M., Ramaiya, N.H., Hatabu, H. & Hodi, F.S. Monitoring immune-checkpoint blockade: response evaluation and biomarker development. Nature reviews Clinical oncology 14, 655-668 (2017).
Notelet et al., "Proliferating cell nuclear antigen (PCNA) in cerebral cavernomas: An immunocytochemical study of 42 cases" 1997 Surg. Neurol. 47: 364-370.
Ouyang S. et al., 2012. Structural analysis of the STING adaptor protein reveals a hydrophobic dimer interface and mode of cyclic di-GMP binding. Immunity. 36(6):1073-86.
Pandey et al., "Association of the DF3/MUC1 breast cancer antigen with Grb2 and the Sos/Ras exchange protein" 1995, Cancer Res. 55: 4000-4003.
Patel, S. et al. The Common R71H-G230A-R293Q Human TMEM173 Is a Null Allele. Journal of immunology (Baltimore, Md. : 1950) 198, 776-787 (2017).
Patel, S.A. & Minn, A.J. Combination Cancer Therapy with Immune Checkpoint Blockade: Mechanisms and Strategies. Immunity 48, 417-433 (2018).
Pearson, "Rapid and sensitive sequence comparison with FASTP and FASTA" (1990), Methods Enzymol. 183, 63-98.
Pearson and Lipman, "Improved tools for biological sequence comparison" (1988), Proc. Natl. Acad. Sci. U.S.A 85, 2444-2448.
Pharmaceuticals, N. Study of the Safety and Efficacy of MIW815 With PDR001 in Patients With Advanced/Metastatic Solid Tumors or Lymphomas. https://beta.clinicaltrials.gov/study/NCT03172936 (accessed May 10, 2023).
Rattan et al., (1992) Protein Synthesis: Post-translational Modifications and Aging, Ann NY Acad Sci, 663: 48-62.
Rosenberg, J. & Huang, J. CD8(+) T Cells and NK Cells: Parallel and Complementary Soldiers of Immunotherapy. Current opinion in chemical engineering 19, 9-20 (2018).
Rossi, M. et al. STING Agonist Combined to a Protein-Based Cancer Vaccine Potentiates Peripheral and Intra-Tumoral T Cell Immunity. Frontiers in immunology 12 (2021).
Ruiz-Moreno, J.S. et al. The common Haq Sting variant impairs cGAS-dependent antibacterial responses and is associated with susceptibility to Legionnaires' disease in humans. PLoS pathogens 14, e1006829 (2018).
International Search Report and Written Opinion of PCT/US2021/037023 mailed Nov. 5, 2021.
Sato, Y. et al. CD4+ T cells induce rejection of urothelial tumors after immune checkpoint blockade. JCI insight 3 (2018).
Seifter et al. (1990) Analysis for protein modifications and nonprotein cofactors, Meth. Enzymol. 182: 626-646.
Shakya, A.K., Lee, C.H., Uddin, M.J. & Gill, H.S. Assessment of Th1/Th2 Bias of STING Agonists Coated on Microneedles for Possible Use in Skin Allergen Immunotherapy. Molecular pharmaceutics 15, 5437-5443 (2018).
Sharma, P. & Allison, J.P. The future of immune checkpoint therapy. Science 348, 56-61 (2015).

(56) References Cited

OTHER PUBLICATIONS

Shields, M.D., Marin-Acevedo, J.A. & Pellini, B. Immunotherapy for Advanced Non-Small Cell Lung Cancer: A Decade of Progress. American Society of Clinical Oncology Educational Book, e105-e127 (2021).
Shitara, K. et al. First-in-human phase 1 study of IT1208, a defucosylated humanized anti-CD4 depleting antibody, in patients with advanced solid tumors. Journal for immunotherapy of cancer 7, 1-11 (2019).
Simon et al., "Peptoids: a modular approach to drug discovery" Proc. Natl. Acad. Sci. U.S.A. (1992) 89: 9367-71.
Smith and Waterman, "Identification of common molecular subsequences" (1981), J. Mol. Biol. 147, 195-197.
Sokolowska, O. et al. Immune checkpoint inhibition improves antimyeloma activity of bortezomib and STING agonist combination in Vk*MYC preclinical model. Clinical and experimental medicine (2022).
Tanaka et al., "STING specifies IRF3 phosphorylation by TBK1 in the cytosolic DNA signaling pathway" Sci Signal. (Mar. 6, 2012) 5(214):ra20.
Tay, R.E., Richardson, E.K. & Toh, H.C. Revisiting the role of CD4+ T cells in cancer immunotherapy—new insights Into old paradigms. Cancer Gene Therapy 28, 5-17 (2021).
Tie, Y., Tang, F., Wei, Y.-q. & Wei, X.-w. Immunosuppressive cells in cancer: mechanisms and potential therapeutic targets. Journal of Hematology & Oncology 15, 61 (2022).
Tolliver and O'Brien, "Elevated tumor-associated antigen CA 19-9 in a patient with an enlarged pancreas: does it always imply malignancy?" 1997, South Med. J. 90: 89-90.
Tsuruta at al., "CA19-9: a possible serum marker for embryonal carcinoma" 1997 Urol. Int. 58: 20-24.
Ueha, S. et al. Robust Antitumor Effects of Combined Anti-CD4-Depleting Antibody and Anti-PD-1/PD-L1 Immune Checkpoint Antibody Treatment in MiceAnti-CD4 and Immune Checkpoint Antibody Synergy. Cancer immunology research 3, 631-640 (2015).
Ulrich-Lewis, J.T. et al. STING is required in conventional dendritic cells for DNA vaccine induction of type IT helper cell-dependent antibody responses. Frontiers in immunology 13 (2022).
Vafaei, S. et al. Combination therapy with immune checkpoint inhibitors (ICIs); a new frontier. Cancer Cell International 22, 2 (2022).
Van Herck, S., Feng, B. & Tang, L. Delivery of STING agonists for adjuvanting subunit vaccines. Advanced Drug Delivery Reviews 179, 114020 (2021).
Varayathu, H., Sarathy, V., Thomas, B.E., Mufti, S.S. & Naik, R. Combination Strategies to Augment Immune Check Point Inhibitors Efficacy—Implications for Translational Research. Frontiers in oncology 11, 559161 (2021).
Walker, M.M. et al. Selective Loss of Responsiveness to Exogenous but Not Endogenous Cyclic-Dinucleotides in Mice Expressing STING-R231H. Frontiers in immunology 11, 238 (2020).
Wculek, S.K. et al. Dendritic cells in cancer immunology and immunotherapy. Nature reviews. Immunology 20, 7-24 (2020).
Wolchok, J.D. et al. Overall Survival with Combined Nivolumab and Ipilimumab in Advanced Melanoma. New England Journal of Medicine 377, 1345-1356 (2017).
Wu, J. & Chen, Z.J. Innate immune sensing and signaling of cytosolic nucleic acids. Annu Rev Immunol 32, 461-488 (2014).
Zajac et al., "Generation of tumoricidal cytotoxic T lymphocytes from healthy donors after in vitro stimulation with a replication-incompetent vaccinia virus encoding MART-1/Melan-A 27-35 epitope" 1997, Int. J Cancer 71: 491-496.
Zantek et al., "E-cadherin regulates the function of the EphA2 receptor tyrosine kinase" Cell Growth Differ. (1999) 10:629-38.
Zhou, Y. et al. First-line treatment for patients with advanced non-small cell lung carcinoma and high PD-L1 expression: pembrolizumab or pembrolizumab plus chemotherapy. Journal for immunotherapy of cancer 7, 120 (2019).
Zou, W., Wolchok, J.D. & Chen, L. PD-L1 (B7-H1) and PD-1 pathway blockade for cancer therapy: Mechanisms, response biomarkers, and combinations. Science translational medicine 8, 328rv324-328rv324 (2016).
Li et al., "Structurally Programmed Assembly of Translation Initiation Nanoplex for Superior mRNA Delivery" ACS Nano. 2017, 11(3): 2531-2544.
Li et al. "Polyamine-Mediated Stoichiometric Assembly of Ribonucleoproteins for Enhanced mRNA Delivery" Angew Chem Int Ed Engl. 56(44): 13709-13712, (Oct. 2017).
Li et al. "Structurally modulated codelivery of siRNA and Argonaute 2 for enhanced RNA interference" PNAS 115(12): E2696-E2705, (Feb. 2018).
Lucas et al., "Identification of a 35 kD tumor-associated autoantigen in papillary thyroid carcinoma" Anticancer Res. 16 (5A): 2493-2496, (Sep.-Oct. 1996).
Wang et al. ""A novel transcript 1-12,17, isoform of STING that sequesters cGAMP and 18dominantly inhibits innate nucleic acid sensing"". Nucleic Acid Research 46(8): 4054-4071, (May 2018).
Wang et al. "STING activator c-di-GMP enhances the anti-tumor effects of peptide vaccines in melanoma-bearing mice". Cancer Immunology Immunotherapy 64(8): 1057-1066, (May 2015).
Zhang et al. "Structural basis of STING binding with and phosphorylation by TBK1". Nature 567(7748): 394-398, (Mar. 2019).
Landman et al. "Balancing STING in antimicrobial defense and autoinflammation". Cytokine and Growth Factor Reviews 55:1-14, (Jun. 2020).
Belcher et al., U.S. Appl. No. 18/312,030, filed May 4, 2023.
Aini et al. "Messenger RNA delivery of a cartilage-anabolic transcription factor as a disease-modifying strategy for osteoarthritis treatment", Sci Rep. Jan. 5, 2016;6:18743.
Alspach, E. et al. MHC-II neoantigens shape tumour immunity and response to immunotherapy. Nature 574, 696-701 (2019).
Altschul et al. "Basic local alignment search tool", 1990, J. Mol. Biol. 215, 403-410.
Altschul et al. "Gapped BLAST and PSI-BLAST: a new generation of protein database search programs" (1997), Nucleic Acids Res, 25:3389-3402.
Agarwal, Y. et al. Intratumourally injected alum-tethered cytokines elicit potent and safer local and systemic anticancer Immunity. Nature Biomedical Engineering 6, 129-143 (2022).
Amouzegar, A., Chelvanambi, M., Filderman, J.N., Storkus, W.J. & Luke, J.J. Sting Agonists as Cancer Therapeutics. Cancers 13 (2021).
Antonelli, A.C., Binyamin, A., Hohl, T.M., Glickman, M.S. & Redelman-Sidi, G. Bacterial immunotherapy for cancer induces CD4-dependent tumor-specific immunity through tumor-intrinsic interferon-y signaling. Proceedings of the National Academy of Sciences 117, 18627-18637 (2020).
Apostolopoulos et al. "Breast cancer immunotherapy: Current status and future prospects", 1996 Immunol. Cell. Biol. 74: 457-464.
Bagchi, S., Yuan, R. & Engleman, E.G. Immune checkpoint inhibitors for the treatment of cancer: clinical impact and mechanisms of response and resistance. Annual Review of Pathology: Mechanisms of Disease 16, 223-249 (2021).
Bald, T., Krummel, M.F., Smyth, M.J. & Barry, K.C. The NK cell-cancer cycle: advances and new challenges in NK cell-based immunotherapies. Nature immunology 21, 835-847 (2020).
Barbari, C. et al. Immunotherapies and Combination Strategies for Immuno-Oncology. International journal of molecular sciences 21 (2020).
Benoit-Lizon, I. et al. CD4 T cell-intrinsic STING signaling controls the differentiation and effector functions of TH1 and TH9 cells. Journal for immunotherapy of cancer 10 (2022).
Berger, G. et al. STING activation promotes robust immune response and NK cell-mediated tumor regression in glioblastoma models. Proceedings of the National Academy of Sciences 119, e2111003119 (2022).
Bihl, F., Germain, C., Luci, C. & Braud, V.M. Mechanisms of NK cell activation: CD4+ T cells enter the scene. Cellular and Molecular Life Sciences 68, 3457 (2011).

(56) References Cited

OTHER PUBLICATIONS

Borden, E.C. Interferons α and β in cancer: therapeutic opportunities from new insights. Nature Reviews Drug Discovery 18, 219-234 (2019).
Borst, J., Ahrends, T., Babala, N., Melief, C.J. & Kastenmüller, W. CD4+ T cell help in cancer immunology and Immunotherapy. Nature Reviews Immunology 18, 635-647 (2018).
Brady et al. "Reflections on a peptide" Nature, 368, 692-693 (1994).
Carles-Kinch et al., ""Antibody targeting of the EphA2 tyrosine kinase inhibitsmalignant cell behavior"", Cancer Res. (2002) 62:2840-7.
Carlino, M.S., Larkin, J. & Long, G.V. Immune checkpoint inhibitors in melanoma. The Lancet 398, 1002-1014 (2021).
Cerboni, S et al. Intrinsic antiproliferative activity of the innate sensor STING in T lymphocytes. Journal of Experimental Medicine 214, 1769-1785 (2017).
Chen, Daniel S. & Mellman, I. Oncology Meets Immunology: The Cancer-Immunity Cycle. Immunity 39, 1-10 (2013).
Cheng at al., "The ephrins and Eph receptors in angiogenesis" 2002, Cytokine Growth Factor Rev. 13:75-85.
Cheng, N. et al. A nanoparticle-incorporated STING activator enhances antitumor immunity in PD-L1-insensitive models of triple-negative breast cancer. JCI insight 3 (2018).
Chon, H. Effect of STING agonist on tumor immune microenvironment of non-inflamed lung cancer and efficacy of Immune checkpoint blockade. Journal of Clinical Oncology 36, 178-178 (2018) (meeting abstract) https://ascopubs.org/doi/abs/10.1200/JCO.2018.36.5_suppl. 178 (accessed May 10, 2023).
Dahlenborg et al., "Human monoclonal antibodies specific for the tumour associated Thomsen-Friedenreich antigen" 1997, Int. J Cancer 70: 63-71.
Deshpande and Danishefsky, "Total synthesis of the potential anticancer vaccine KH-1 adenocarcinoma antigen"1997, Nature 387: 164-166.
Devereux et al., "A comprehensive set of sequence analysis programs for the VAX" 1984, Nucleic Acids Res., 387-395.
Dongye, Z., Li, J. & Wu, Y. Toll-like receptor 9 agonists and combination therapies: strategies to modulate the tumour immune microenvironment for systemic anti-tumour immunity. British Journal of Cancer (2022).
Dowdy, "Overcoming cellular barriers for RNA therapeutics" Nature Biotechnology 35, 222-229 (2017).
Emambux, S., Tachon, G., Junca, A. & Tougeron, D. Results and challenges of immune checkpoint inhibitors in colorectal cancer. Expert Opinion on Biological Therapy 18, 561-573 (2018).
Fishman et al., "Autoantibodies to tyrosinase: The bridge between melanoma and vitiligo" 1997 Cancer 79: 1461-1464.
Garland, K.M., Sheehy, T.L. & Wilson, J.T. Chemical and Biomolecular Strategies for STING Pathway Activation in Cancer Immunotherapy. Chemical Reviews (2022).
Ghaffari, A. et al. STING agonist therapy in combination with PD-1 immune checkpoint blockade enhances response to carboplatin chemotherapy in high-grade serous ovarian cancer. Br J Cancer 119, 440-449 (2018).
Golshani, G. & Zhang, Y. Advances in immunotherapy for colorectal cancer: a review. Therapeutic advances in gastroenterology 13, 1756284820917527 (2020).
Grosser, R., Cherkassky, L., Chintala, N. & Adusumilli, P.S. Combination Immunotherapy with Car T Cells and Checkpoint Blockade for the Treatment of Solid Tumors. Cancer cell 36, 471-482 (2019).
Haslam, A. & Prasad, V. Estimation of the Percentage of US Patients With Cancer Who Are Eligible for and Respond to Checkpoint Inhibitor Immunotherapy Drugs. JAMA network open 2, e192535 (2019).
He et al. Self-assembled cGAMP-STINGΔTM signaling complex as a bioinspired platform for cGAMP delivery. Science advances 6, eaba7589 (Jun. 2020).
He et al. Peptide-based Cancer Vaccine Delivery via the STINGΔTM-cGAMP Complex. Advanced Healthcare Materials, 2200905.
He, Y., Hong, C., Irvine, D.J., Li, J. & Hammond, P.T. In vitro STING Activation with the cGAMP-STINGΔTM Signaling Complex. Bio-protocol 11, e3905-e3905 (2021).
Huang et al., "CEA-based vaccines", Exper Rev. Vaccines (2002)1:49-63.
Huemer, F. et al. Combination Strategies for Immune-Checkpoint Blockade and Response Prediction by Artificial Intelligence. International journal of molecular sciences 21 (2020).
Mmunovative Therapies, L. Immunotherapy for Third Line Metastatic Colorectal Cancer (STIMVAX). https://beta.clinicaltrials.gov/study/NCT03172936 (accessed May 10, 2023).
Innes et al., "Significance of the metastasis-inducing protein AGR2 for outcome in hormonally treated breast cancer patients", Br. J. Cancer 94:1057-1065 (2006).
Jameson et al., "A rationally designed CD4 analogue inhibits experimental allergic encephalomyelitis" Nature, 368, 744-746 (1994).
Jailkhani, N. et al. Noninvasive imaging of tumor progression, metastasis, and fibrosis using a nanobody targeting the extracellular matrix. Proceedings of the National Academy of Sciences 116, 14181-14190 (2019).
Jenkins, R.W., Barbie, D.A. & Flaherty, K.T. Mechanisms of resistance to immune checkpoint inhibitors. British journal of cancer 118, 9-16 (2018).
Jing, W., Gershan, J.A. & Johnson, B.D. Depletion of CD4 T cells enhances immunotherapy for neuroblastoma after syngeneic HSCT but compromises development of antitumor immune memory. Blood, The Journal of the American Society of Hematology 113, 4449-4457 (2009).
Karlin et al., "Applications and statistics for multiple high-scoring segments in molecular sequences" (1993), PNAS USA, 90:5873-5877.
Kawakami and Rosenberg, "Immunobiology of human melanoma antigens MART-1 and gp100 and their use for Immuno-gene therapy" 1997, Int. Rev. Immunol. 14: 173-192.

* cited by examiner

| Seq ID | Primer name | Sequence (5' – 3') | Seq ID NO | Primer name | Sequence (5' – 3') |
|---|---|---|---|---|---|
| 29 | mSTING TM deletion.F | TTGACTCCAGCGGAAGTC | 47 | mSTING.F | ataaAGATCTttgactccagcggaagtctc |
| 30 | mSTING TM deletion.R | CATGGTGGCTCTAGAGTC | 48 | mSTING.R | ataagaatGCGGCCGCtcagatgaggtcagtgcgga |
| 31 | hSTING (S366A).F | GCTCCTCATCgcaGGAATGGAAAAGCC | 49 | mSTING (S365A).F | ACTCCTCATCgcaGGTATGGATCAGCC |
| 32 | hSTING (S366A).R | TCAGGCTCTTGGGACATC | 50 | mSTING (S365A).R | CTTGGCTCTTGGGACAGT |
| 33 | hSTING (L374A).F | GCCCCTCCCTgcaCGCACGGATT | 51 | mSTING (L373A).F | GCCTCTCCCAgcaCGCACTGACC |
| 34 | hSTING (L374A).R | TTTTCCATTCCACTGATGAGG | 52 | mSTING (L373A).R | TGATCCATACCACTGATG |
| 35 | mSTING_XbaI_F | gggctgcaggtcgactctagagccaccatgccatact | 53 | STING (dC9).F | TGAGCGGCCGCACTCGAG |
| 36 | mSTING_EcoRI_R | atcgataagcttgatatcgaattctcagatgaggtca | 54 | hSTING (dC9).R | CTTTTCCATTCCACTGATGAGGAGCTC |
| 37 | hSTING TM deletion.F | CTGGCCCCAGCTGAGATC | 55 | mSTING (dC9).R | CTGATCCATACCACTGATGAGGAGTCTTG |
| 38 | hSTING TM deletion.R | CATGGTGGCAATTCCACC | 56 | mSTING_NcoI.F | ttgactccagcggaagtctctgc |
| 39 | hSTING_FLAG.F | gatgacgacaagTGAGACCCAGGGTCACCA | 57 | mSTING_NotI.R | ggtggtgctcgagtgcggccgctcagatgaggtcagtgc |
| 40 | hSTING_FLAG.R | gtctttgtagtcAGAGAAATCCGTGCGGAG | 58 | qPCR-mTBK1.F | GACATGCCTCTCTCCTGTAGTC |
| 41 | mSTING | ttgcTTCCAACAGCGTCTACGA | 59 | qPCR-mTBK1.R | GGTGAAGCACATCACTGGTCTC |
| 42 | mSTING | cagcATTCTTGATGCCAGCACG | 60 | qPCR-mIRF3.F | CGGAAAGAAGTGTTGCGGTTAGC |
| 43 | hSTING (R238Y240A).F | tgcaAGCAACAGCATCTATGAG | 61 | qPCR-mIRF3.R | CAGGCTGCTTTTGCCATTGGTG |
| 44 | hSTING (R238Y240A).R | acagcATCCTTGATGCCAGCATG | 62 | qPCR-mIFN-beta.F | GCCTTTGCCATCCAAGAGATGC |
| 45 | hSTING.F | ataatGGATCCctggccccagctgagatct | 63 | qPCR-mIFN-beta.R | ACACTGTCTGCTGGTGGAGTTC |
| 46 | hSTING.R | ataagaatGCGGCCGCtcaagagaaatccgtgc | 64 | qPCR-mTBK1.F | GACATGCCTCTCTCCTGTAGTC |
| | | | 65 | qPCR-mTBK1.R | GGTGAAGCACATCACTGGTCTC |

FIG. 28

SEQUENCE LISTING

<160> NUMBER OF SEQ ID NOS: 67

<210> SEQ ID NO 1
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Leu Ala Pro Ala Glu Ile Ser Ala Val Cys Glu Lys Gly Asn Phe Asn
1 5 10 15

Val Ala His Gly Leu Ala Trp Ser Tyr Tyr Ile Gly Tyr Leu Arg Leu
20 25 30

Ile Leu Pro Glu Leu Gln Ala Arg Ile Arg Thr Tyr Asn Gln His Tyr
35 40 45

Asn Asn Leu Leu Arg Gly Ala Val Ser Gln Arg Leu Tyr Ile Leu Leu
50 55 60

Pro Leu Asp Cys Gly Val Pro Asp Asn Leu Ser Met Ala Asp Pro Asn
65 70 75 80

Ile Arg Phe Leu Asp Lys Leu Pro Gln Gln Thr Gly Asp Arg Ala Gly
85 90 95

Ile Lys Asp Arg Val Tyr Ser Asn Ser Ile Tyr Glu Leu Leu Glu Asn
100 105 110

Gly Gln Arg Ala Gly Thr Cys Val Leu Glu Tyr Ala Thr Pro Leu Gln
115 120 125

Thr Leu Phe Ala Met Ser Gln Tyr Ser Gln Ala Gly Phe Ser Arg Glu
130 135 140

Asp Arg Leu Glu Gln Ala Lys Leu Phe Cys Arg Thr Leu Glu Asp Ile
145 150 155 160

Leu Ala Asp Ala Pro Glu Ser Gln Asn Asn Cys Arg Leu Ile Ala Tyr
165 170 175

Gln Glu Pro Ala Asp Asp Ser Ser Phe Ser Leu Ser Gln Glu Val Leu
180 185 190

Arg His Leu Arg Gln Glu Glu Lys Glu Glu Val Thr Val Gly Ser Leu
195 200 205

Lys Thr Ser Ala Val Pro Ser Thr Ser Thr Met Ser Gln Glu Pro Glu
210 215 220

Leu Leu Ile Ser Gly Met Glu Lys Pro Leu Pro Leu Arg Thr Asp Phe
225 230 235 240

Ser

<210> SEQ ID NO 2
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

Ser Leu Ala Pro Ala Glu Ile Ser Ala Val Cys Glu Lys Gly Asn Phe
1 5 10 15

Asn Val Ala His Gly Leu Ala Trp Ser Tyr Tyr Ile Gly Tyr Leu Arg
20 25 30

Leu Ile Leu Pro Glu Leu Gln Ala Arg Ile Arg Thr Tyr Asn Gln His
35 40 45

Tyr Asn Asn Leu Leu Arg Gly Ala Val Ser Gln Arg Leu Tyr Ile Leu
50 55 60

Leu Pro Leu Asp Cys Gly Val Pro Asp Asn Leu Ser Met Ala Asp Pro
65 70 75 80

```
Asn Ile Arg Phe Leu Asp Lys Leu Pro Gln Gln Thr Gly Asp Arg Ala
                85                  90                  95

Gly Ile Lys Asp Arg Val Tyr Ser Asn Ser Ile Tyr Glu Leu Leu Glu
            100                 105                 110

Asn Gly Gln Arg Ala Gly Thr Cys Val Leu Glu Tyr Ala Thr Pro Leu
        115                 120                 125

Gln Thr Leu Phe Ala Met Ser Gln Tyr Ser Gln Ala Gly Phe Ser Arg
    130                 135                 140

Glu Asp Arg Leu Glu Gln Ala Lys Leu Phe Cys Arg Thr Leu Glu Asp
145                 150                 155                 160

Ile Leu Ala Asp Ala Pro Glu Ser Gln Asn Asn Cys Arg Leu Ile Ala
                165                 170                 175

Tyr Gln Glu Pro Ala Asp Asp Ser Ser Phe Ser Leu Ser Gln Glu Val
            180                 185                 190

Leu Arg His Leu Arg Gln Glu Glu Lys Glu Glu Val Thr Val Gly Ser
        195                 200                 205

Leu Lys Thr Ser Ala Val Pro Ser Thr Ser Thr Met Ser Gln Glu Pro
    210                 215                 220

Glu Leu Leu Ile Ser Gly Met Glu Lys Pro Leu Pro Leu Arg Thr Asp
225                 230                 235                 240

Phe Ser


<210> SEQ ID NO 3
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Leu Ala Pro Ala Glu Ile Ser Ala Val Cys Glu Lys Gly Asn Phe Asn
1               5                   10                  15

Val Ala His Gly Leu Ala Trp Ser Tyr Tyr Ile Gly Tyr Leu Arg Leu
            20                  25                  30

Ile Leu Pro Glu Leu Gln Ala Arg Ile Arg Thr Tyr Asn Gln His Tyr
        35                  40                  45

Asn Asn Leu Leu Arg Gly Ala Val Ser Gln Arg Leu Tyr Ile Leu Leu
    50                  55                  60

Pro Leu Asp Cys Gly Val Pro Asp Asn Leu Ser Met Ala Asp Pro Asn
65                  70                  75                  80

Ile Arg Phe Leu Asp Lys Leu Pro Gln Gln Thr Gly Asp Arg Ala Gly
                85                  90                  95

Ile Lys Asp Arg Val Tyr Ser Asn Ser Ile Tyr Glu Leu Leu Glu Asn
            100                 105                 110

Gly Gln Arg Ala Gly Thr Cys Val Leu Glu Tyr Ala Thr Pro Leu Gln
        115                 120                 125

Thr Leu Phe Ala Met Ser Gln Tyr Ser Gln Ala Gly Phe Ser Arg Glu
    130                 135                 140

Asp Arg Leu Glu Gln Ala Lys Leu Phe Cys Arg Thr Leu Glu Asp Ile
145                 150                 155                 160

Leu Ala Asp Ala Pro Glu Ser Gln Asn Asn Cys Arg Leu Ile Ala Tyr
                165                 170                 175

Gln Glu Pro Ala Asp Asp Ser Ser Phe Ser Leu Ser Gln Glu Val Leu
            180                 185                 190
```

```
Arg His Leu Arg Gln Glu Glu Lys Glu Glu Val Thr Val Gly Ser Leu
        195                 200                 205

Lys Thr Ser Ala Val Pro Ser Thr Ser Thr Met Ser Gln Glu Pro Glu
    210                 215                 220

Leu Leu Ile Ala Gly Met Glu Lys Pro Leu Pro Leu Arg Thr Asp Phe
225                 230                 235                 240

Ser


<210> SEQ ID NO 4
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Ser Leu Ala Pro Ala Glu Ile Ser Ala Val Cys Glu Lys Gly Asn Phe
1               5                   10                  15

Asn Val Ala His Gly Leu Ala Trp Ser Tyr Tyr Ile Gly Tyr Leu Arg
            20                  25                  30

Leu Ile Leu Pro Glu Leu Gln Ala Arg Ile Arg Thr Tyr Asn Gln His
        35                  40                  45

Tyr Asn Asn Leu Leu Arg Gly Ala Val Ser Gln Arg Leu Tyr Ile Leu
    50                  55                  60

Leu Pro Leu Asp Cys Gly Val Pro Asp Asn Leu Ser Met Ala Asp Pro
65                  70                  75                  80

Asn Ile Arg Phe Leu Asp Lys Leu Pro Gln Gln Thr Gly Asp Arg Ala
                85                  90                  95

Gly Ile Lys Asp Arg Val Tyr Ser Asn Ser Ile Tyr Glu Leu Leu Glu
            100                 105                 110

Asn Gly Gln Arg Ala Gly Thr Cys Val Leu Glu Tyr Ala Thr Pro Leu
        115                 120                 125

Gln Thr Leu Phe Ala Met Ser Gln Tyr Ser Gln Ala Gly Phe Ser Arg
    130                 135                 140

Glu Asp Arg Leu Glu Gln Ala Lys Leu Phe Cys Arg Thr Leu Glu Asp
145                 150                 155                 160

Ile Leu Ala Asp Ala Pro Glu Ser Gln Asn Asn Cys Arg Leu Ile Ala
                165                 170                 175

Tyr Gln Glu Pro Ala Asp Asp Ser Ser Phe Ser Leu Ser Gln Glu Val
            180                 185                 190

Leu Arg His Leu Arg Gln Glu Glu Lys Glu Glu Val Thr Val Gly Ser
        195                 200                 205

Leu Lys Thr Ser Ala Val Pro Ser Thr Ser Thr Met Ser Gln Glu Pro
    210                 215                 220

Glu Leu Leu Ile Ala Gly Met Glu Lys Pro Leu Pro Leu Arg Thr Asp
225                 230                 235                 240

Phe Ser


<210> SEQ ID NO 5
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 5

Leu Ala Pro Ala Glu Ile Ser Ala Val Cys Glu Lys Gly Asn Phe Asn
1 5 10 15

Val Ala His Gly Leu Ala Trp Ser Tyr Tyr Ile Gly Tyr Leu Arg Leu
20 25 30

Ile Leu Pro Glu Leu Gln Ala Arg Ile Arg Thr Tyr Asn Gln His Tyr
35 40 45

Asn Asn Leu Leu Arg Gly Ala Val Ser Gln Arg Leu Tyr Ile Leu Leu
50 55 60

Pro Leu Asp Cys Gly Val Pro Asp Asn Leu Ser Met Ala Asp Pro Asn
65 70 75 80

Ile Arg Phe Leu Asp Lys Leu Pro Gln Gln Thr Gly Asp Arg Ala Gly
85 90 95

Ile Lys Asp Arg Val Tyr Ser Asn Ser Ile Tyr Glu Leu Leu Glu Asn
100 105 110

Gly Gln Arg Ala Gly Thr Cys Val Leu Glu Tyr Ala Thr Pro Leu Gln
115 120 125

Thr Leu Phe Ala Met Ser Gln Tyr Ser Gln Ala Gly Phe Ser Arg Glu
130 135 140

Asp Arg Leu Glu Gln Ala Lys Leu Phe Cys Arg Thr Leu Glu Asp Ile
145 150 155 160

Leu Ala Asp Ala Pro Glu Ser Gln Asn Asn Cys Arg Leu Ile Ala Tyr
165 170 175

Gln Glu Pro Ala Asp Asp Ser Ser Phe Ser Leu Ser Gln Glu Val Leu
180 185 190

Arg His Leu Arg Gln Glu Glu Lys Glu Glu Val Thr Val Gly Ser Leu
195 200 205

Lys Thr Ser Ala Val Pro Ser Thr Ser Thr Met Ser Gln Glu Pro Glu
210 215 220

Leu Leu Ile Ser Gly Met Glu Lys Pro Leu Pro Ala Arg Thr Asp Phe
225 230 235 240

Ser

<210> SEQ ID NO 6
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

Ser Leu Ala Pro Ala Glu Ile Ser Ala Val Cys Glu Lys Gly Asn Phe
1 5 10 15

Asn Val Ala His Gly Leu Ala Trp Ser Tyr Tyr Ile Gly Tyr Leu Arg
20 25 30

Leu Ile Leu Pro Glu Leu Gln Ala Arg Ile Arg Thr Tyr Asn Gln His
35 40 45

Tyr Asn Asn Leu Leu Arg Gly Ala Val Ser Gln Arg Leu Tyr Ile Leu
50 55 60

Leu Pro Leu Asp Cys Gly Val Pro Asp Asn Leu Ser Met Ala Asp Pro
65 70 75 80

Asn Ile Arg Phe Leu Asp Lys Leu Pro Gln Gln Thr Gly Asp Arg Ala

-continued

```
                85                  90                  95

Gly Ile Lys Asp Arg Val Tyr Ser Asn Ser Ile Tyr Glu Leu Leu Glu
            100                 105                 110

Asn Gly Gln Arg Ala Gly Thr Cys Val Leu Glu Tyr Ala Thr Pro Leu
        115                 120                 125

Gln Thr Leu Phe Ala Met Ser Gln Tyr Ser Gln Ala Gly Phe Ser Arg
    130                 135                 140

Glu Asp Arg Leu Glu Gln Ala Lys Leu Phe Cys Arg Thr Leu Glu Asp
145                 150                 155                 160

Ile Leu Ala Asp Ala Pro Glu Ser Gln Asn Asn Cys Arg Leu Ile Ala
                165                 170                 175

Tyr Gln Glu Pro Ala Asp Asp Ser Ser Phe Ser Leu Ser Gln Glu Val
            180                 185                 190

Leu Arg His Leu Arg Gln Glu Glu Lys Glu Glu Val Thr Val Gly Ser
        195                 200                 205

Leu Lys Thr Ser Ala Val Pro Ser Thr Ser Thr Met Ser Gln Glu Pro
    210                 215                 220

Glu Leu Leu Ile Ser Gly Met Glu Lys Pro Leu Pro Ala Arg Thr Asp
225                 230                 235                 240

Phe Ser


<210> SEQ ID NO 7
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Leu Ala Pro Ala Glu Ile Ser Ala Val Cys Glu Lys Gly Asn Phe Asn
1               5                   10                  15

Val Ala His Gly Leu Ala Trp Ser Tyr Tyr Ile Gly Tyr Leu Arg Leu
            20                  25                  30

Ile Leu Pro Glu Leu Gln Ala Arg Ile Arg Thr Tyr Asn Gln His Tyr
        35                  40                  45

Asn Asn Leu Leu Arg Gly Ala Val Ser Gln Arg Leu Tyr Ile Leu Leu
    50                  55                  60

Pro Leu Asp Cys Gly Val Pro Asp Asn Leu Ser Met Ala Asp Pro Asn
65                  70                  75                  80

Ile Arg Phe Leu Asp Lys Leu Pro Gln Gln Thr Gly Asp Arg Ala Gly
                85                  90                  95

Ile Lys Asp Ala Val Ala Ser Asn Ser Ile Tyr Glu Leu Leu Glu Asn
            100                 105                 110

Gly Gln Arg Ala Gly Thr Cys Val Leu Glu Tyr Ala Thr Pro Leu Gln
        115                 120                 125

Thr Leu Phe Ala Met Ser Gln Tyr Ser Gln Ala Gly Phe Ser Arg Glu
    130                 135                 140

Asp Arg Leu Glu Gln Ala Lys Leu Phe Cys Arg Thr Leu Glu Asp Ile
145                 150                 155                 160

Leu Ala Asp Ala Pro Glu Ser Gln Asn Asn Cys Arg Leu Ile Ala Tyr
                165                 170                 175

Gln Glu Pro Ala Asp Asp Ser Ser Phe Ser Leu Ser Gln Glu Val Leu
            180                 185                 190
```

-continued

```
Arg His Leu Arg Gln Glu Glu Lys Glu Glu Val Thr Val Gly Ser Leu
        195                 200                 205

Lys Thr Ser Ala Val Pro Ser Thr Ser Thr Met Ser Gln Glu Pro Glu
    210                 215                 220

Leu Leu Ile Ser Gly Met Glu Lys Pro Leu Pro Leu Arg Thr Asp Phe
225                 230                 235                 240

Ser
```

<210> SEQ ID NO 8
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Ser Leu Ala Pro Ala Glu Ile Ser Ala Val Cys Glu Lys Gly Asn Phe
1               5                   10                  15

Asn Val Ala His Gly Leu Ala Trp Ser Tyr Tyr Ile Gly Tyr Leu Arg
            20                  25                  30

Leu Ile Leu Pro Glu Leu Gln Ala Arg Ile Arg Thr Tyr Asn Gln His
        35                  40                  45

Tyr Asn Asn Leu Leu Arg Gly Ala Val Ser Gln Arg Leu Tyr Ile Leu
    50                  55                  60

Leu Pro Leu Asp Cys Gly Val Pro Asp Asn Leu Ser Met Ala Asp Pro
65                  70                  75                  80

Asn Ile Arg Phe Leu Asp Lys Leu Pro Gln Gln Thr Gly Asp Arg Ala
                85                  90                  95

Gly Ile Lys Asp Ala Val Ala Ser Asn Ser Ile Tyr Glu Leu Leu Glu
            100                 105                 110

Asn Gly Gln Arg Ala Gly Thr Cys Val Leu Glu Tyr Ala Thr Pro Leu
        115                 120                 125

Gln Thr Leu Phe Ala Met Ser Gln Tyr Ser Gln Ala Gly Phe Ser Arg
    130                 135                 140

Glu Asp Arg Leu Glu Gln Ala Lys Leu Phe Cys Arg Thr Leu Glu Asp
145                 150                 155                 160

Ile Leu Ala Asp Ala Pro Glu Ser Gln Asn Asn Cys Arg Leu Ile Ala
                165                 170                 175

Tyr Gln Glu Pro Ala Asp Asp Ser Ser Phe Ser Leu Ser Gln Glu Val
            180                 185                 190

Leu Arg His Leu Arg Gln Glu Glu Lys Glu Glu Val Thr Val Gly Ser
        195                 200                 205

Leu Lys Thr Ser Ala Val Pro Ser Thr Ser Thr Met Ser Gln Glu Pro
    210                 215                 220

Glu Leu Leu Ile Ser Gly Met Glu Lys Pro Leu Pro Leu Arg Thr Asp
225                 230                 235                 240

Phe Ser
```

<210> SEQ ID NO 9
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

Leu Ala Pro Ala Glu Ile Ser Ala Val Cys Glu Lys Gly Asn Phe Asn
1               5                   10                  15

Val Ala His Gly Leu Ala Trp Ser Tyr Tyr Ile Gly Tyr Leu Arg Leu
            20                  25                  30

Ile Leu Pro Glu Leu Gln Ala Arg Ile Arg Thr Tyr Asn Gln His Tyr
        35                  40                  45

Asn Asn Leu Leu Arg Gly Ala Val Ser Gln Arg Leu Tyr Ile Leu Leu
    50                  55                  60

Pro Leu Asp Cys Gly Val Pro Asp Asn Leu Ser Met Ala Asp Pro Asn
65                  70                  75                  80

Ile Arg Phe Leu Asp Lys Leu Pro Gln Gln Thr Gly Asp Arg Ala Gly
                85                  90                  95

Ile Lys Asp Arg Val Tyr Ser Asn Ser Ile Tyr Glu Leu Leu Glu Asn
            100                 105                 110

Gly Gln Arg Ala Gly Thr Cys Val Leu Glu Tyr Ala Thr Pro Leu Gln
        115                 120                 125

Thr Leu Phe Ala Met Ser Gln Tyr Ser Gln Ala Gly Phe Ser Arg Glu
    130                 135                 140

Asp Arg Leu Glu Gln Ala Lys Leu Phe Cys Arg Thr Leu Glu Asp Ile
145                 150                 155                 160

Leu Ala Asp Ala Pro Glu Ser Gln Asn Asn Cys Arg Leu Ile Ala Tyr
                165                 170                 175

Gln Glu Pro Ala Asp Asp Ser Ser Phe Ser Leu Ser Gln Glu Val Leu
            180                 185                 190

Arg His Leu Arg Gln Glu Glu Lys Glu Glu Val Thr Val Gly Ser Leu
        195                 200                 205

Lys Thr Ser Ala Val Pro Ser Thr Ser Thr Met Ser Gln Glu Pro Glu
    210                 215                 220

Leu Leu Ile Ser Gly Met Glu Lys
225                 230

<210> SEQ ID NO 10
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ser Leu Ala Pro Ala Glu Ile Ser Ala Val Cys Glu Lys Gly Asn Phe
1               5                   10                  15

Asn Val Ala His Gly Leu Ala Trp Ser Tyr Tyr Ile Gly Tyr Leu Arg
            20                  25                  30

Leu Ile Leu Pro Glu Leu Gln Ala Arg Ile Arg Thr Tyr Asn Gln His
        35                  40                  45

Tyr Asn Asn Leu Leu Arg Gly Ala Val Ser Gln Arg Leu Tyr Ile Leu
    50                  55                  60

Leu Pro Leu Asp Cys Gly Val Pro Asp Asn Leu Ser Met Ala Asp Pro
65                  70                  75                  80

Asn Ile Arg Phe Leu Asp Lys Leu Pro Gln Gln Thr Gly Asp Arg Ala
                85                  90                  95

Gly Ile Lys Asp Arg Val Tyr Ser Asn Ser Ile Tyr Glu Leu Leu Glu

```
            100                 105                 110

Asn Gly Gln Arg Ala Gly Thr Cys Val Leu Glu Tyr Ala Thr Pro Leu
        115                 120                 125

Gln Thr Leu Phe Ala Met Ser Gln Tyr Ser Gln Ala Gly Phe Ser Arg
    130                 135                 140

Glu Asp Arg Leu Glu Gln Ala Lys Leu Phe Cys Arg Thr Leu Glu Asp
145                 150                 155                 160

Ile Leu Ala Asp Ala Pro Glu Ser Gln Asn Asn Cys Arg Leu Ile Ala
                165                 170                 175

Tyr Gln Glu Pro Ala Asp Asp Ser Ser Phe Ser Leu Ser Gln Glu Val
            180                 185                 190

Leu Arg His Leu Arg Gln Glu Glu Lys Glu Glu Val Thr Val Gly Ser
        195                 200                 205

Leu Lys Thr Ser Ala Val Pro Ser Thr Ser Thr Met Ser Gln Glu Pro
    210                 215                 220

Glu Leu Leu Ile Ser Gly Met Glu Lys
225                 230


<210> SEQ ID NO 11
<211> LENGTH: 379
<212> TYPE: PRT
<213> ORGANISM: Homo sapiens

<400> SEQUENCE: 11

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp Arg Ala Gly Ile Lys Asp Arg Val Tyr
225                 230                 235                 240
```

-continued

```
Ser Asn Ser Ile Tyr Glu Leu Leu Glu Asn Gly Gln Arg Ala Gly Thr
            245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375


<210> SEQ ID NO 12
<211> LENGTH: 379
<212> TYPE: PRT
<213> ORGANISM: Homo sapiens

<400> SEQUENCE: 12

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu His His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Ala Asp Arg Ala Gly Ile Lys Asp Arg Val Tyr
225                 230                 235                 240
```

```
Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Gln Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375


<210> SEQ ID NO 13
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Leu Thr Pro Ala Glu Val Ser Ala Val Cys Glu Glu Lys Lys Leu Asn
1               5                   10                  15

Val Ala His Gly Leu Ala Trp Ser Tyr Tyr Ile Gly Tyr Leu Arg Leu
            20                  25                  30

Ile Leu Pro Gly Leu Gln Ala Arg Ile Arg Met Phe Asn Gln Leu His
        35                  40                  45

Asn Asn Met Leu Ser Gly Ala Gly Ser Arg Arg Leu Tyr Ile Leu Phe
    50                  55                  60

Pro Leu Asp Cys Gly Val Pro Asp Asn Leu Ser Val Val Asp Pro Asn
65                  70                  75                  80

Ile Arg Phe Arg Asp Met Leu Pro Gln Gln Asn Ile Asp Arg Ala Gly
                85                  90                  95

Ile Lys Asn Arg Val Tyr Ser Asn Ser Val Tyr Glu Ile Leu Glu Asn
            100                 105                 110

Gly Gln Pro Ala Gly Val Cys Ile Leu Glu Tyr Ala Thr Pro Leu Gln
        115                 120                 125

Thr Leu Phe Ala Met Ser Gln Asp Ala Lys Ala Gly Phe Ser Arg Glu
    130                 135                 140

Asp Arg Leu Glu Gln Ala Lys Leu Phe Cys Arg Thr Leu Glu Glu Ile
145                 150                 155                 160

Leu Glu Asp Val Pro Glu Ser Arg Asn Asn Cys Arg Leu Ile Val Tyr
                165                 170                 175

Gln Glu Pro Thr Asp Gly Asn Ser Phe Ser Leu Ser Gln Glu Val Leu
            180                 185                 190

Arg His Ile Arg Gln Glu Glu Lys Glu Glu Val Thr Met Asn Ala Pro
        195                 200                 205
```

```
Met Thr Ser Val Ala Pro Pro Pro Ser Val Leu Ser Gln Glu Pro Arg
    210                 215                 220

Leu Leu Ile Ser Gly Met Asp Gln Pro Leu Pro Leu Arg Thr Asp Leu
225                 230                 235                 240

Ile


<210> SEQ ID NO 14
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Ser Leu Thr Pro Ala Glu Val Ser Ala Val Cys Glu Glu Lys Lys Leu
1               5                   10                  15

Asn Val Ala His Gly Leu Ala Trp Ser Tyr Tyr Ile Gly Tyr Leu Arg
            20                  25                  30

Leu Ile Leu Pro Gly Leu Gln Ala Arg Ile Arg Met Phe Asn Gln Leu
        35                  40                  45

His Asn Asn Met Leu Ser Gly Ala Gly Ser Arg Arg Leu Tyr Ile Leu
    50                  55                  60

Phe Pro Leu Asp Cys Gly Val Pro Asp Asn Leu Ser Val Val Asp Pro
65                  70                  75                  80

Asn Ile Arg Phe Arg Asp Met Leu Pro Gln Gln Asn Ile Asp Arg Ala
                85                  90                  95

Gly Ile Lys Asn Arg Val Tyr Ser Asn Ser Val Tyr Glu Ile Leu Glu
            100                 105                 110

Asn Gly Gln Pro Ala Gly Val Cys Ile Leu Glu Tyr Ala Thr Pro Leu
        115                 120                 125

Gln Thr Leu Phe Ala Met Ser Gln Asp Ala Lys Ala Gly Phe Ser Arg
    130                 135                 140

Glu Asp Arg Leu Glu Gln Ala Lys Leu Phe Cys Arg Thr Leu Glu Glu
145                 150                 155                 160

Ile Leu Glu Asp Val Pro Glu Ser Arg Asn Asn Cys Arg Leu Ile Val
                165                 170                 175

Tyr Gln Glu Pro Thr Asp Gly Asn Ser Phe Ser Leu Ser Gln Glu Val
            180                 185                 190

Leu Arg His Ile Arg Gln Glu Glu Lys Glu Glu Val Thr Met Asn Ala
        195                 200                 205

Pro Met Thr Ser Val Ala Pro Pro Pro Ser Val Leu Ser Gln Glu Pro
    210                 215                 220

Arg Leu Leu Ile Ser Gly Met Asp Gln Pro Leu Pro Leu Arg Thr Asp
225                 230                 235                 240

Leu Ile


<210> SEQ ID NO 15
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15
```

```
Leu Thr Pro Ala Glu Val Ser Ala Val Cys Glu Glu Lys Lys Leu Asn
1               5                   10                  15

Val Ala His Gly Leu Ala Trp Ser Tyr Tyr Ile Gly Tyr Leu Arg Leu
            20                  25                  30

Ile Leu Pro Gly Leu Gln Ala Arg Ile Arg Met Phe Asn Gln Leu His
        35                  40                  45

Asn Asn Met Leu Ser Gly Ala Gly Ser Arg Arg Leu Tyr Ile Leu Phe
    50                  55                  60

Pro Leu Asp Cys Gly Val Pro Asp Asn Leu Ser Val Val Asp Pro Asn
65                  70                  75                  80

Ile Arg Phe Arg Asp Met Leu Pro Gln Gln Asn Ile Asp Arg Ala Gly
                85                  90                  95

Ile Lys Asn Arg Val Tyr Ser Asn Ser Val Tyr Glu Ile Leu Glu Asn
            100                 105                 110

Gly Gln Pro Ala Gly Val Cys Ile Leu Glu Tyr Ala Thr Pro Leu Gln
        115                 120                 125

Thr Leu Phe Ala Met Ser Gln Asp Ala Lys Ala Gly Phe Ser Arg Glu
    130                 135                 140

Asp Arg Leu Glu Gln Ala Lys Leu Phe Cys Arg Thr Leu Glu Glu Ile
145                 150                 155                 160

Leu Glu Asp Val Pro Glu Ser Arg Asn Asn Cys Arg Leu Ile Val Tyr
                165                 170                 175

Gln Glu Pro Thr Asp Gly Asn Ser Phe Ser Leu Ser Gln Glu Val Leu
            180                 185                 190

Arg His Ile Arg Gln Glu Glu Lys Glu Glu Val Thr Met Asn Ala Pro
        195                 200                 205

Met Thr Ser Val Ala Pro Pro Pro Ser Val Leu Ser Gln Glu Pro Arg
    210                 215                 220

Leu Leu Ile Ala Gly Met Asp Gln Pro Leu Pro Leu Arg Thr Asp Leu
225                 230                 235                 240

Ile
```

```
<210> SEQ ID NO 16
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Ser Leu Thr Pro Ala Glu Val Ser Ala Val Cys Glu Glu Lys Lys Leu
1               5                   10                  15

Asn Val Ala His Gly Leu Ala Trp Ser Tyr Tyr Ile Gly Tyr Leu Arg
            20                  25                  30

Leu Ile Leu Pro Gly Leu Gln Ala Arg Ile Arg Met Phe Asn Gln Leu
        35                  40                  45

His Asn Asn Met Leu Ser Gly Ala Gly Ser Arg Arg Leu Tyr Ile Leu
    50                  55                  60

Phe Pro Leu Asp Cys Gly Val Pro Asp Asn Leu Ser Val Val Asp Pro
65                  70                  75                  80

Asn Ile Arg Phe Arg Asp Met Leu Pro Gln Gln Asn Ile Asp Arg Ala
                85                  90                  95

Gly Ile Lys Asn Arg Val Tyr Ser Asn Ser Val Tyr Glu Ile Leu Glu
            100                 105                 110
```

```
Asn Gly Gln Pro Ala Gly Val Cys Ile Leu Glu Tyr Ala Thr Pro Leu
        115                 120                 125

Gln Thr Leu Phe Ala Met Ser Gln Asp Ala Lys Ala Gly Phe Ser Arg
    130                 135                 140

Glu Asp Arg Leu Glu Gln Ala Lys Leu Phe Cys Arg Thr Leu Glu Glu
145                 150                 155                 160

Ile Leu Glu Asp Val Pro Glu Ser Arg Asn Asn Cys Arg Leu Ile Val
                165                 170                 175

Tyr Gln Glu Pro Thr Asp Gly Asn Ser Phe Ser Leu Ser Gln Glu Val
            180                 185                 190

Leu Arg His Ile Arg Gln Glu Glu Lys Glu Glu Val Thr Met Asn Ala
        195                 200                 205

Pro Met Thr Ser Val Ala Pro Pro Pro Ser Val Leu Ser Gln Glu Pro
    210                 215                 220

Arg Leu Leu Ile Ala Gly Met Asp Gln Pro Leu Pro Leu Arg Thr Asp
225                 230                 235                 240

Leu Ile


<210> SEQ ID NO 17
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Leu Thr Pro Ala Glu Val Ser Ala Val Cys Glu Glu Lys Lys Leu Asn
1               5                   10                  15

Val Ala His Gly Leu Ala Trp Ser Tyr Tyr Ile Gly Tyr Leu Arg Leu
            20                  25                  30

Ile Leu Pro Gly Leu Gln Ala Arg Ile Arg Met Phe Asn Gln Leu His
        35                  40                  45

Asn Asn Met Leu Ser Gly Ala Gly Ser Arg Arg Leu Tyr Ile Leu Phe
    50                  55                  60

Pro Leu Asp Cys Gly Val Pro Asp Asn Leu Ser Val Val Asp Pro Asn
65                  70                  75                  80

Ile Arg Phe Arg Asp Met Leu Pro Gln Gln Asn Ile Asp Arg Ala Gly
                85                  90                  95

Ile Lys Asn Arg Val Tyr Ser Asn Ser Val Tyr Glu Ile Leu Glu Asn
            100                 105                 110

Gly Gln Pro Ala Gly Val Cys Ile Leu Glu Tyr Ala Thr Pro Leu Gln
        115                 120                 125

Thr Leu Phe Ala Met Ser Gln Asp Ala Lys Ala Gly Phe Ser Arg Glu
    130                 135                 140

Asp Arg Leu Glu Gln Ala Lys Leu Phe Cys Arg Thr Leu Glu Glu Ile
145                 150                 155                 160

Leu Glu Asp Val Pro Glu Ser Arg Asn Asn Cys Arg Leu Ile Val Tyr
                165                 170                 175

Gln Glu Pro Thr Asp Gly Asn Ser Phe Ser Leu Ser Gln Glu Val Leu
            180                 185                 190

Arg His Ile Arg Gln Glu Glu Lys Glu Glu Val Thr Met Asn Ala Pro
        195                 200                 205

Met Thr Ser Val Ala Pro Pro Pro Ser Val Leu Ser Gln Glu Pro Arg
```

```
    210                 215                 220

Leu Leu Ile Ser Gly Met Asp Gln Pro Leu Pro Ala Arg Thr Asp Leu
225                 230                 235                 240

Ile


<210> SEQ ID NO 18
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Ser Leu Thr Pro Ala Glu Val Ser Ala Val Cys Glu Glu Lys Lys Leu
1               5                   10                  15

Asn Val Ala His Gly Leu Ala Trp Ser Tyr Tyr Ile Gly Tyr Leu Arg
            20                  25                  30

Leu Ile Leu Pro Gly Leu Gln Ala Arg Ile Arg Met Phe Asn Gln Leu
        35                  40                  45

His Asn Asn Met Leu Ser Gly Ala Gly Ser Arg Arg Leu Tyr Ile Leu
    50                  55                  60

Phe Pro Leu Asp Cys Gly Val Pro Asp Asn Leu Ser Val Val Asp Pro
65                  70                  75                  80

Asn Ile Arg Phe Arg Asp Met Leu Pro Gln Gln Asn Ile Asp Arg Ala
                85                  90                  95

Gly Ile Lys Asn Arg Val Tyr Ser Asn Ser Val Tyr Glu Ile Leu Glu
            100                 105                 110

Asn Gly Gln Pro Ala Gly Val Cys Ile Leu Glu Tyr Ala Thr Pro Leu
        115                 120                 125

Gln Thr Leu Phe Ala Met Ser Gln Asp Ala Lys Ala Gly Phe Ser Arg
    130                 135                 140

Glu Asp Arg Leu Glu Gln Ala Lys Leu Phe Cys Arg Thr Leu Glu Glu
145                 150                 155                 160

Ile Leu Glu Asp Val Pro Glu Ser Arg Asn Asn Cys Arg Leu Ile Val
                165                 170                 175

Tyr Gln Glu Pro Thr Asp Gly Asn Ser Phe Ser Leu Ser Gln Glu Val
            180                 185                 190

Leu Arg His Ile Arg Gln Glu Glu Lys Glu Glu Val Thr Met Asn Ala
        195                 200                 205

Pro Met Thr Ser Val Ala Pro Pro Pro Ser Val Leu Ser Gln Glu Pro
    210                 215                 220

Arg Leu Leu Ile Ser Gly Met Asp Gln Pro Leu Pro Ala Arg Thr Asp
225                 230                 235                 240

Leu Ile


<210> SEQ ID NO 19
<211> LENGTH: 241
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Leu Thr Pro Ala Glu Val Ser Ala Val Cys Glu Glu Lys Lys Leu Asn
```

```
1               5                   10                  15

Val Ala His Gly Leu Ala Trp Ser Tyr Tyr Ile Gly Tyr Leu Arg Leu
            20                  25                  30

Ile Leu Pro Gly Leu Gln Ala Arg Ile Arg Met Phe Asn Gln Leu His
        35                  40                  45

Asn Asn Met Leu Ser Gly Ala Gly Ser Arg Arg Leu Tyr Ile Leu Phe
    50                  55                  60

Pro Leu Asp Cys Gly Val Pro Asp Asn Leu Ser Val Val Asp Pro Asn
65                  70                  75                  80

Ile Arg Phe Arg Asp Met Leu Pro Gln Gln Asn Ile Asp Arg Ala Gly
                85                  90                  95

Ile Lys Asn Ala Val Ala Ser Asn Ser Val Tyr Glu Ile Leu Glu Asn
            100                 105                 110

Gly Gln Pro Ala Gly Val Cys Ile Leu Glu Tyr Ala Thr Pro Leu Gln
        115                 120                 125

Thr Leu Phe Ala Met Ser Gln Asp Ala Lys Ala Gly Phe Ser Arg Glu
    130                 135                 140

Asp Arg Leu Glu Gln Ala Lys Leu Phe Cys Arg Thr Leu Glu Glu Ile
145                 150                 155                 160

Leu Glu Asp Val Pro Glu Ser Arg Asn Asn Cys Arg Leu Ile Val Tyr
                165                 170                 175

Gln Glu Pro Thr Asp Gly Asn Ser Phe Ser Leu Ser Gln Glu Val Leu
            180                 185                 190

Arg His Ile Arg Gln Glu Glu Lys Glu Glu Val Thr Met Asn Ala Pro
        195                 200                 205

Met Thr Ser Val Ala Pro Pro Pro Ser Val Leu Ser Gln Glu Pro Arg
    210                 215                 220

Leu Leu Ile Ser Gly Met Asp Gln Pro Leu Pro Leu Arg Thr Asp Leu
225                 230                 235                 240

Ile


<210> SEQ ID NO 20
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Ser Leu Thr Pro Ala Glu Val Ser Ala Val Cys Glu Glu Lys Lys Leu
1               5                   10                  15

Asn Val Ala His Gly Leu Ala Trp Ser Tyr Tyr Ile Gly Tyr Leu Arg
            20                  25                  30

Leu Ile Leu Pro Gly Leu Gln Ala Arg Ile Arg Met Phe Asn Gln Leu
        35                  40                  45

His Asn Asn Met Leu Ser Gly Ala Gly Ser Arg Arg Leu Tyr Ile Leu
    50                  55                  60

Phe Pro Leu Asp Cys Gly Val Pro Asp Asn Leu Ser Val Val Asp Pro
65                  70                  75                  80

Asn Ile Arg Phe Arg Asp Met Leu Pro Gln Gln Asn Ile Asp Arg Ala
                85                  90                  95

Gly Ile Lys Asn Ala Val Ala Ser Asn Ser Val Tyr Glu Ile Leu Glu
            100                 105                 110
```

Asn Gly Gln Pro Ala Gly Val Cys Ile Leu Glu Tyr Ala Thr Pro Leu
115 120 125

Gln Thr Leu Phe Ala Met Ser Gln Asp Ala Lys Ala Gly Phe Ser Arg
130 135 140

Glu Asp Arg Leu Glu Gln Ala Lys Leu Phe Cys Arg Thr Leu Glu Glu
145 150 155 160

Ile Leu Glu Asp Val Pro Glu Ser Arg Asn Asn Cys Arg Leu Ile Val
165 170 175

Tyr Gln Glu Pro Thr Asp Gly Asn Ser Phe Ser Leu Ser Gln Glu Val
180 185 190

Leu Arg His Ile Arg Gln Glu Glu Lys Glu Glu Val Thr Met Asn Ala
195 200 205

Pro Met Thr Ser Val Ala Pro Pro Pro Ser Val Leu Ser Gln Glu Pro
210 215 220

Arg Leu Leu Ile Ser Gly Met Asp Gln Pro Leu Pro Leu Arg Thr Asp
225 230 235 240

Leu Ile

<210> SEQ ID NO 21
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

Leu Thr Pro Ala Glu Val Ser Ala Val Cys Glu Glu Lys Lys Leu Asn
1 5 10 15

Val Ala His Gly Leu Ala Trp Ser Tyr Tyr Ile Gly Tyr Leu Arg Leu
20 25 30

Ile Leu Pro Gly Leu Gln Ala Arg Ile Arg Met Phe Asn Gln Leu His
35 40 45

Asn Asn Met Leu Ser Gly Ala Gly Ser Arg Arg Leu Tyr Ile Leu Phe
50 55 60

Pro Leu Asp Cys Gly Val Pro Asp Asn Leu Ser Val Val Asp Pro Asn
65 70 75 80

Ile Arg Phe Arg Asp Met Leu Pro Gln Gln Asn Ile Asp Arg Ala Gly
85 90 95

Ile Lys Asn Arg Val Tyr Ser Asn Ser Val Tyr Glu Ile Leu Glu Asn
100 105 110

Gly Gln Pro Ala Gly Val Cys Ile Leu Glu Tyr Ala Thr Pro Leu Gln
115 120 125

Thr Leu Phe Ala Met Ser Gln Asp Ala Lys Ala Gly Phe Ser Arg Glu
130 135 140

Asp Arg Leu Glu Gln Ala Lys Leu Phe Cys Arg Thr Leu Glu Glu Ile
145 150 155 160

Leu Glu Asp Val Pro Glu Ser Arg Asn Asn Cys Arg Leu Ile Val Tyr
165 170 175

Gln Glu Pro Thr Asp Gly Asn Ser Phe Ser Leu Ser Gln Glu Val Leu
180 185 190

Arg His Ile Arg Gln Glu Glu Lys Glu Glu Val Thr Met Asn Ala Pro
195 200 205

Met Thr Ser Val Ala Pro Pro Pro Ser Val Leu Ser Gln Glu Pro Arg
210 215 220

Leu Leu Ile Ser Gly Met Asp Gln
225 230

<210> SEQ ID NO 22
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

Ser Leu Thr Pro Ala Glu Val Ser Ala Val Cys Glu Glu Lys Lys Leu
1 5 10 15

Asn Val Ala His Gly Leu Ala Trp Ser Tyr Tyr Ile Gly Tyr Leu Arg
20 25 30

Leu Ile Leu Pro Gly Leu Gln Ala Arg Ile Arg Met Phe Asn Gln Leu
35 40 45

His Asn Asn Met Leu Ser Gly Ala Gly Ser Arg Arg Leu Tyr Ile Leu
50 55 60

Phe Pro Leu Asp Cys Gly Val Pro Asp Asn Leu Ser Val Val Asp Pro
65 70 75 80

Asn Ile Arg Phe Arg Asp Met Leu Pro Gln Gln Asn Ile Asp Arg Ala
85 90 95

Gly Ile Lys Asn Arg Val Tyr Ser Asn Ser Val Tyr Glu Ile Leu Glu
100 105 110

Asn Gly Gln Pro Ala Gly Val Cys Ile Leu Glu Tyr Ala Thr Pro Leu
115 120 125

Gln Thr Leu Phe Ala Met Ser Gln Asp Ala Lys Ala Gly Phe Ser Arg
130 135 140

Glu Asp Arg Leu Glu Gln Ala Lys Leu Phe Cys Arg Thr Leu Glu Glu
145 150 155 160

Ile Leu Glu Asp Val Pro Glu Ser Arg Asn Asn Cys Arg Leu Ile Val
165 170 175

Tyr Gln Glu Pro Thr Asp Gly Asn Ser Phe Ser Leu Ser Gln Glu Val
180 185 190

Leu Arg His Ile Arg Gln Glu Glu Lys Glu Glu Val Thr Met Asn Ala
195 200 205

Pro Met Thr Ser Val Ala Pro Pro Pro Ser Val Leu Ser Gln Glu Pro
210 215 220

Arg Leu Leu Ile Ser Gly Met Asp Gln
225 230

<210> SEQ ID NO 23
<211> LENGTH: 378
<212> TYPE: PRT
<213> ORGANISM: Mus musculus

<400> SEQUENCE: 23

Met Pro Tyr Ser Asn Leu His Pro Ala Ile Pro Arg Pro Arg Gly His
1 5 10 15

Arg Ser Lys Tyr Val Ala Leu Ile Phe Leu Val Ala Ser Leu Met Ile
20 25 30

Leu Trp Val Ala Lys Asp Pro Pro Asn His Thr Leu Lys Tyr Leu Ala
35 40 45

Leu His Leu Ala Ser His Glu Leu Gly Leu Leu Leu Lys Asn Leu Cys

```
    50                  55                  60

Cys Leu Ala Glu Glu Leu Cys His Val Gln Ser Arg Tyr Gln Gly Ser
65                  70                  75                  80

Tyr Trp Lys Ala Val Arg Ala Cys Leu Gly Cys Pro Ile His Cys Met
                85                  90                  95

Ala Met Ile Leu Leu Ser Ser Tyr Phe Tyr Phe Leu Gln Asn Thr Ala
            100                 105                 110

Asp Ile Tyr Leu Ser Trp Met Phe Gly Leu Leu Val Leu Tyr Lys Ser
        115                 120                 125

Leu Ser Met Leu Leu Gly Leu Gln Ser Leu Thr Pro Ala Glu Val Ser
    130                 135                 140

Ala Val Cys Glu Glu Lys Lys Leu Asn Val Ala His Gly Leu Ala Trp
145                 150                 155                 160

Ser Tyr Tyr Ile Gly Tyr Leu Arg Leu Ile Leu Pro Gly Leu Gln Ala
                165                 170                 175

Arg Ile Arg Met Phe Asn Gln Leu His Asn Asn Met Leu Ser Gly Ala
            180                 185                 190

Gly Ser Arg Arg Leu Tyr Ile Leu Phe Pro Leu Asp Cys Gly Val Pro
        195                 200                 205

Asp Asn Leu Ser Val Val Asp Pro Asn Ile Arg Phe Arg Asp Met Leu
    210                 215                 220

Pro Gln Gln Asn Ile Asp Arg Ala Gly Ile Lys Asn Arg Val Tyr Ser
225                 230                 235                 240

Asn Ser Val Tyr Glu Ile Leu Glu Asn Gly Gln Pro Ala Gly Val Cys
                245                 250                 255

Ile Leu Glu Tyr Ala Thr Pro Leu Gln Thr Leu Phe Ala Met Ser Gln
            260                 265                 270

Asp Ala Lys Ala Gly Phe Ser Arg Glu Asp Arg Leu Glu Gln Ala Lys
        275                 280                 285

Leu Phe Cys Arg Thr Leu Glu Glu Ile Leu Glu Asp Val Pro Glu Ser
    290                 295                 300

Arg Asn Asn Cys Arg Leu Ile Val Tyr Gln Glu Pro Thr Asp Gly Asn
305                 310                 315                 320

Ser Phe Ser Leu Ser Gln Glu Val Leu Arg His Ile Arg Gln Glu Glu
                325                 330                 335

Lys Glu Glu Val Thr Met Asn Ala Pro Met Thr Ser Val Ala Pro Pro
            340                 345                 350

Pro Ser Val Leu Ser Gln Glu Pro Arg Leu Leu Ile Ser Gly Met Asp
        355                 360                 365

Gln Pro Leu Pro Leu Arg Thr Asp Leu Ile
    370                 375
```

<210> SEQ ID NO 24
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30
```

```
Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly
    130                 135


<210> SEQ ID NO 25
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Leu Glu Gln Leu Glu Ser Ile Ile Asn Phe Glu Lys Leu Thr Glu
1               5                   10                  15

Trp Thr Ser Ser
            20


<210> SEQ ID NO 26
<211> LENGTH: 1136
<212> TYPE: DNA
<213> ORGANISM: Homo sapiens

<400> SEQUENCE: 26

atgccccact ccagcctgca tccatccatc ccgtgtccca ggggtcacgg ggcccagaag     60

gcagccttgg ttctgctgag tgcctgcctg gtgaccattg ggggctagga gagccaccag    120

agcacactct ccggtacctg gtgctccacc tagcctccct gcagctggga ctgctgttaa    180

acggggtctg cagcctggct gaggagctgc gccacatcca ctccaggtac cggggcagct    240

actggaggac tgtgcgggcc tgcctgggct gcccccctccg ccgtggggcc ctgttgctgc    300

tgtccatcta tttctactac tccctcccaa atgcggtcgg cccgcccttc acttggatgc    360

ttgccctcct gggcctctcg caggcactga acatcctcct gggcctcaag ggcctggccc    420

cagctgagat ctctgcagtg tgtgaaaaag ggaatttcaa cgtggcccat gggctggcat    480

ggtcatatta catcggatat ctgcggctga tcctgccaga gctccaggcc cggattcgaa    540

cttacaatca gcattacaac aacctgctac ggggtgcagt gagccagcgg ctgtatattc    600

tcctcccatt ggactgtggg gtgcctgata acctgagtat ggctgacccc aacattcgct    660

tcctggataa actgccccag cagaccggtg accgggctgg catcaaggat cgggtttaca    720

gcaacagcat ctatgagatc tggagaacgg gcagcgggcg ggcacctgtg tcctggagta    780

cgccaccccc ttgcagactt tgtttgccat gtcacaatac agtcaagctg gctttagccg    840

ggaggatagg cttgagcagg ccaaactatc tgccggacac ttgaggacat cctggcagat    900

gcccctgagt ctcagaacaa ctgccgcctc attgcctacc aggaacctgc agatgacagc    960
```

agatctcgct gtcccaggag gttctccggc acctgcggca ggaggaaaag gaagaggtta 1020
ctgtgggcag cttgaagacc tcagcggtgc ccagtacctc cacgatgtcc caagagcctg 1080
agctcctcat cagtggaatg gaaaagcccc tccctctccg cacggatttc tcttga 1136

<210> SEQ ID NO 27
<211> LENGTH: 1133
<212> TYPE: DNA
<213> ORGANISM: Homo sapiens

<400> SEQUENCE: 27
atgccccact ccagcctgca tccatccatc ccgtgtccca ggggtcacgg ggcccagaag 60
gcagccttgg ttctgctgag tgcctgcctg gtgaccattg ggggctagga gagccaccag 120
agcacactct ccggtacctg gtgctccacc tagcctccct gcagctggga ctgctgttaa 180
acggggtctg cagcctggct gaggagctgc gccacatcca ctccaggtac cggggcagct 240
actggaggac tgtgcgggcc tgcctgggct gccccctccg ccgtggggcc ctgttgctgc 300
tgtccatcta tttctactac tccctcccaa atgcggtcgg cccgccatca cttggatgat 360
gccctcctgg gcctctcgca ggcactgaac atcctcctgg gcctcaaggg cctggcccca 420
gctgagatct ctgcagtgtg tgaaaaaggg aatttcaacg tggcccatgg gctggcatgg 480
tcatattaca tcggatatct gcggctgatc ctgccagagc tccaggcccg gattcgaact 540
tacaatcagc attacaacaa cctgctacgg ggtgcagtga gccagcggct gtatattctc 600
ctcccattgg actgtggggt gcctgataac ctgagtatgg ctgaccccaa cattcgatcc 660
tggataaact gccccagcag accggtgacc atgctggcat caaggatcgg gtttacagca 720
acagcatcta tgagcttctg gagaacgggc agcgggcggg cacctgtgtc ctggagtacg 780
ccaccccatg cagactttgt ttgccatgtc acaatacagt caagctggct ttagccggga 840
ggataggctt gagcaggcca aactatctgc cggacacttg aggacatcct ggcagatgcc 900
cctgagtctc agaacaactg ccgcctcatt gcctaccagg aacctgcaga tgacagcaga 960
tctcgctgtc ccaggaggtt ctccggcacc tgcggcagga ggaaaaggaa gaggttactg 1020
tgggcagctt gaagacctca gcggtgccca gtacctccac gatgtcccaa gagcctgagc 1080
tcctcatcag tggaatggaa aagcccctcc ctctccgcac ggatttctct tga 1133

<210> SEQ ID NO 28
<211> LENGTH: 1139
<212> TYPE: DNA
<213> ORGANISM: Homo sapiens
<220> FEATURE:
<221> NAME/KEY: modified_base
<222> LOCATION: (806)..(806)
<223> OTHER INFORMATION: a, c, t, g, unknown or other

<400> SEQUENCE: 28
atgccccact ccagcctgca tccatccatc ccgtgtccca ggggtcacgg ggcccagaag 60
gcagccttgg ttctgctgag tgcctgcctg gtgacccttt gggggctagg agagccacca 120
gagcacactc tccggtacct ggtgctccac ctagcctccc tgcagctggg actgctgtta 180
aacggggtct gcagcctggc tgaggagctg cgccacatcc actccaggta ccggggcagc 240
tactggagga ctgtgcgggc ctgcctgggc tgccccctcc gccgtggggc cctgttgctg 300
ctgtccatct atttctacta ctccctccca aatgcggtcg gcccgccctt cacttggatg 360
cttgccctcc tgggcctctc gcaggcactg aacatcctcc tgggcctcaa gggcctggcc 420

```
ccagctgaga tctctgcagt gtgtgaaaaa gggaatttca acgtggccca tgggctggca    480

tggtcatatt acatcggata tctgcggctg atcctgccag agctccaggc ccggattcga    540

acttacaatc agcattacaa caacctgcta cggggtgcag tgagccagcg gctgtatatt    600

ctcctcccat tggactgtgg ggtgcctgat aacctgagta tggctgaccc caacattcgc    660

ttcctggata aactgcccca gcagaccgct gaccgagctg gcatcaagga tcgggtttac    720

agcaacagca tctatgagct tctggagaac gggcagcggg cgggcacctg tgtcctggag    780

tacgccaccc ccttgcagac tttgrngcca tgtcacaata cagtcaagct ggctttagcc    840

gggaggatag gcttgagcag gccaaactct tctgccagac acttgaggac atcctggcag    900

atgcccctga gtctcagaac aactgccgcc tcattgccta ccaggaacct gcagatgaca    960

gcagcttctc gctgtcccag gaggttctcc ggcacctgcg gcaggaggaa aaggaagagg   1020

ttactgtggg cagcttgaag acctcagcgg tgcccagtac ctccacgatg tcccaagagc   1080

ctgagctcct catcagtgga atggaaaagc cctccctct ccgcacggat ttctcttga    1139


<210> SEQ ID NO 29
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29

ttgactccag cggaagtc                                                   18


<210> SEQ ID NO 30
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30

catggtggct ctagagtc                                                   18


<210> SEQ ID NO 31
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31

gctcctcatc gcaggaatgg aaaagcc                                         27


<210> SEQ ID NO 32
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32

tcaggctctt gggacatc                                                   18
```

<210> SEQ ID NO 33
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 33
gcccctccct gcacgcacgg att 23

<210> SEQ ID NO 34
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 34
ttttccattc cactgatgag g 21

<210> SEQ ID NO 35
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 35
gggctgcagg tcgactctag agccaccatg ccatact 37

<210> SEQ ID NO 36
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 36
atcgataagc ttgatatcga attctcagat gaggtca 37

<210> SEQ ID NO 37
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 37
ctggccccag ctgagatc 18

<210> SEQ ID NO 38
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 38
catggtggca attccacc 18

<210> SEQ ID NO 39
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 39
gatgacgaca agtgagaccc agggtcacca 30

<210> SEQ ID NO 40
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 40
gtctttgtag tcagagaaat ccgtgcggag 30

<210> SEQ ID NO 41
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 41
ttgcttccaa cagcgtctac ga 22

<210> SEQ ID NO 42
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 42
cagcattctt gatgccagca cg 22

<210> SEQ ID NO 43
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 43
tgcaagcaac agcatctatg ag 22

<210> SEQ ID NO 44
<211> LENGTH: 23

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 44
acagcatcct tgatgccagc atg 23

<210> SEQ ID NO 45
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 45
ataatggatc cctggcccca gctgagatct 30

<210> SEQ ID NO 46
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 46
ataagaatgc ggccgctcaa gagaaatccg tgc 33

<210> SEQ ID NO 47
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 47
ataaagatct ttgactccag cggaagtctc 30

<210> SEQ ID NO 48
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 48
ataagaatgc ggccgctcag atgaggtcag tgcgga 36

<210> SEQ ID NO 49
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 49
actcctcatc gcaggtatgg atcagcc 27

<210> SEQ ID NO 50
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 50
cttggctctt gggacagt 18

<210> SEQ ID NO 51
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 51
gcctctccca gcacgcactg acc 23

<210> SEQ ID NO 52
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 52
tgatccatac cactgatg 18

<210> SEQ ID NO 53
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 53
tgagcggccg cactcgag 18

<210> SEQ ID NO 54
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 54
cttttccatt ccactgatga ggagctc 27

<210> SEQ ID NO 55
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 55
ctgatccata ccactgatga ggagtcttg 29

<210> SEQ ID NO 56
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 56
ttgactccag cggaagtctc tgc 23

<210> SEQ ID NO 57
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 57
ggtggtgctc gagtgcggcc gctcagatga ggtcagtgc 39

<210> SEQ ID NO 58
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 58
gacatgcctc tctcctgtag tc 22

<210> SEQ ID NO 59
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 59
ggtgaagcac atcactggtc tc 22

<210> SEQ ID NO 60
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 60
cggaaagaag tgttgcggtt agc 23

<210> SEQ ID NO 61

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61

caggctgctt ttgccattgg tg                                            22


<210> SEQ ID NO 62
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62

gcctttgcca tccaagagat gc                                            22


<210> SEQ ID NO 63
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63

acactgtctg ctggtggagt tc                                            22


<210> SEQ ID NO 64
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64

gacatgcctc tctcctgtag tc                                            22


<210> SEQ ID NO 65
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65

ggtgaagcac atcactggtc tc                                            22


<210> SEQ ID NO 66
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66
```

-continued

```
Ser Ile Ile Asn Phe Glu Lys Leu
1               5
```

```
<210> SEQ ID NO 67
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 67

His His His His His His
1               5
```

RIBONUCLEOPROTEIN APPROACH TO BOOST THE STING SIGNALING FOR CANCER IMMUNOTHERAPY

RELATED APPLICATION(S)

This application claims the benefit of priority U.S. Provisional Application No. 63/037,854, filed Jun. 11, 2020. The entire teachings of the above application(s) are incorporated herein by reference.

BACKGROUND OF THE INVENTION

The stimulator of interferon (IFN) genes (STING) pathway constitutes a highly important part of immune responses against various cancers and infections. Consequently, administration of STING agonists such as cyclic GMP-AMP (cGAMP) has been identified as a promising approach to target these diseases. Several key challenges to cGAMP delivery stem from the molecular nature of cGAMP: as a negatively charged small molecule, it is difficult to deliver it to the cytoplasm where STING is located. Moreover, cGAMP is rapidly cleared in vivo and thus has limited access to tumors. Therefore, methods of efficient cGAMP delivery are needed.

SUMMARY OF THE INVENTION

In the first embodiment, the present invention is a non-covalent complex, comprising: a tetramer of a recombinant protein; and an agonist of a Stimulator of Interferon Gene (STING) protein or a pharmaceutically acceptable salt thereof, wherein the recombinant protein comprises a STING protein lacking a transmembrane domain (STINGΔTM protein).

In the second embodiment, the present invention is a pharmaceutical composition comprising the complex described herein with respect to the first embodiment and various aspects thereof.

In the third embodiment, the present invention is a method of treating or preventing cancer in a subject in need thereof, comprising: administering to the subject in need thereof an effective amount of a non-covalent complex, comprising: a recombinant protein; and an agonist of a STING protein or a pharmaceutically acceptable salt thereof, wherein the recombinant protein comprises a STINGΔTM protein.

In the fourth embodiment, the present invention is a vaccine composition, comprising a non-covalent complex and a pharmaceutically acceptable carrier, wherein the non-covalent complex comprises: a recombinant protein comprising a STINGΔTM protein and a tumor epitope; and an agonist of a STING protein or a pharmaceutically acceptable salt thereof.

In the fifth embodiment, the present invention is a method of initiating, enhancing or prolonging an immune response in a subject, comprising administering the subject an effective amount of the vaccine composition described herein with respect to the fourth embodiment and various aspects thereof.

In the sixth embodiment, the present invention is a kit, comprising: a pharmaceutical composition described herein with respect to the second embodiment and various aspects thereof or a vaccine composition described herein with respect to the fourth embodiment and various aspects thereof; and a pharmaceutical composition comprising an additional pharmaceutically active agent.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 28 shows a list of sequences for the primers used in the synthesis of STINGΔTM protein mutants.

DETAILED DESCRIPTION OF THE INVENTION

Figure 1:
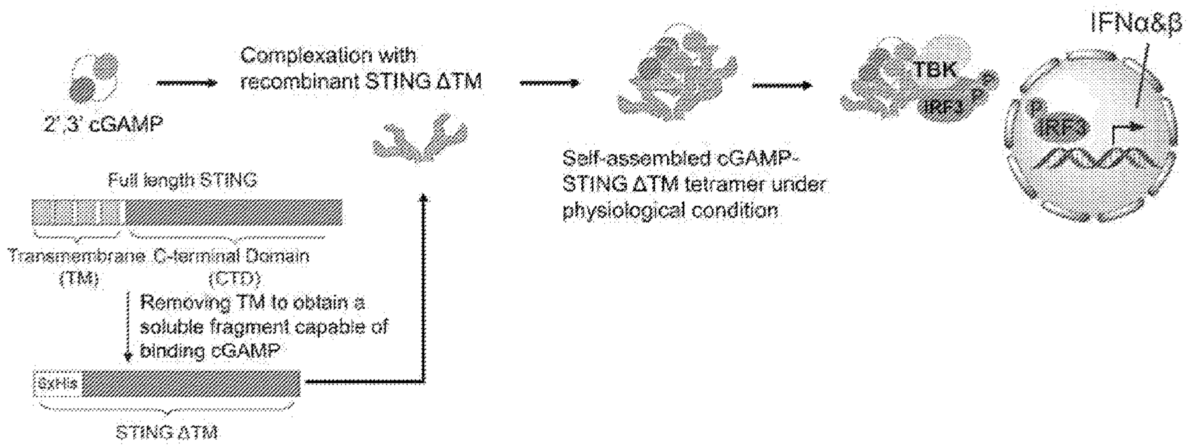
FIG. 1 shows a schematic overview of approaches of cGAMP delivery and schematics of recombinant STINGΔTM structure and therapeutic strategy: strategy of delivering cGAMP with a recombinant transmembrane-deficient STING as carrier in the form of a ribonucleoprotein complex as disclosed herein.

A description of example embodiments of the invention follows.

I. Self-Assembled CDN/STINGΔTM Complexes.

The stimulator of interferon (IFN) genes (STING) pathway constitutes a highly important part of immune responses against various cancers and infections. Consequently, administration of STING agonists such as cyclic GMP-AMP (cGAMP) has been identified as a promising approach to target these diseases. In cancer cells, STING signaling is frequently impaired by epigenetic silencing of STING; hence, conventional delivery of only its agonist cGAMP may be insufficient to trigger STING signaling. As described herein, while expression of STING lacking the transmembrane (TM) domain is known to be unresponsive to STING agonists and is dominant negative when coexpressed with the full-length STING inside cells, it has been observed that the recombinant TM-deficient STING protein complexed with cGAMP could effectively trigger STING signaling when delivered in vitro and in vivo, including in STING-deficient cell lines. Thus, this bio-inspired method using TM-deficient STING may present a new and universally applicable platform for cGAMP delivery.

Cytosolic detection of pathogen- and cancer cell-derived DNA is a major mechanism for immune clearance by inducing type I interferons (IFNs), and the stimulator of interferon genes (STING) is a master regulator that connects DNA sensing via cyclic GMP-AMP synthase (cGAS) to IFN induction. As a transmembrane protein localized to the endoplasmic reticulum, STING consists of an N-terminal transmembrane domain (TM) and a C-terminal domain (CTD), the latter of which binds STING agonists (i.e. cyclic dinucleotides (CDNs) such as 2'3' cyclic guanosine monophosphate-adenosine monophosphate (cGAMP)) and downstream signaling protein tank-binding kinase 1 (TBK1). In addition to antibacterial and antiviral infections, recent evidence has shown an important role of STING in generating a spontaneous antitumor T cell response in the tumor microenvironment (TME). Activation of the STING pathway in the TME can augment dendritic cell maturation and the production of type I interferons and other cytokines, which elicit robust antitumor T cell responses and overcome resistance against immunosuppressive cells that inhibit antitumor immunity. These findings have motivated extensive investigations on the delivery of cGAMP as a strategy for cancer immunotherapy.

Several key challenges to cGAMP delivery stem from the molecular nature of cGAMP: as a negatively charged small molecule, it is difficult to deliver it to the cytoplasm where STING is located. Moreover, cGAMP is rapidly cleared in vivo and thus has limited access to tumors. As such, existing efforts in delivering exogenous cGAMP have focused mostly on the development of novel biomaterials to improve cGAMP's bioavailability. However, one requirement for conventional cGAMP delivery to activate STING signaling is that the cell needs to have functional STING protein. Studies have shown that in cancer cells, STING signaling is frequently impaired due to epigenetic silencing of either STING or cGAMP synthase (cGAS). In addition, it is still under debate whether all human populations are responsive to treatments of direct cGAMP administration. The human TMEM173 gene encoding for STING has high heterogeneity—approximately 19% of humans carry the HAQ STING variant (with three amino acid substitutions R71H-G230A-R293Q, hence the acronym HAQ). Recent literature has shown this mutation to be a null allele, resulting in significant reduction in IFN-β expression, though some other studies argue that HAQ STING is actually functionally responsive.

Described herein is a universal cGAMP delivery platform that can trigger STING signaling independent of endogenous STING functionality to fully address cells that are STING defective or deficient in humans either due to genetic heterogeneity or cancer. Previous studies have demonstrated that transmembrane domain (TM)-deficient STING is capable of activating IRF3 in cytosolic extracts, while others have noted that the TM domain is essential for intracellular STING activation by mediating its translocation from the endoplasmic reticulum (ER) to the Golgi apparatus, where it forms punctate structures indicative of oligomerization. This oligomerization—in particular, the formation of well-defined tetrameric or higher order oligomeric structures—has been demonstrated to be essential to the STING signaling pathway by enabling TBK1 activation which results in IRF3 binding and phosphorylation. While studies have observed a small fraction of cytosolic STING to aggregate upon the addition of cGAMP, the oligomerization of full-length STING is predicted to occur more favorably at high local concentrations on 2D membranes. Surprisingly, by titrating the amount of cGAMP to recombinant, transmembrane-domain-deficient STING (STINGΔTM) of ~30 kDa, a near-complete shift in population towards a ~120 kDa molecular weight ribonucleoprotein (RNP) complex has been observed, suggesting a cGAMP-induced tetramerization. Furthermore, the functionality of this RNP was assessed and it was found to be not only capable of augmenting type I IFN production in cells with endogenous STING expression, but fully activating type I IFN in STING-defective and even STING-deficient cell lines. Finally, its application with in vivo vaccination studies was exploited and enhancement of both innate and adaptive immune responses was observed, including the augmentation of type I IFN expression in vitro and of both TNF-α and IFN-γ in vivo, robust antigen-specific T cell activation and antibody production, and significantly improved therapeutic efficiency in a prophylactic study with melanoma and a treatment study with colon cancer mouse models.

Overview of cGAMP Delivery Strategies

Most, if not all, existing strategies of STING agonist delivery involve directly encapsulating cGAMP into synthetic delivery vehicles, such as liposomes or polymersomes. The primary roles of the vehicles are to package the cyclic dinucleotide, modulate cellular uptake, and facilitate endosomal escape. The vehicles themselves play no functional role in enabling STING signaling, and thus can potentially result in decreased efficacy when treating cells with HAQ STING variants or cells deficient in endogenous STING. Consequently, a bioinspired co-delivery method that precludes the need for fully-functional endogenous STING or cGAMP release from a vehicle was devised, using a recombinant transmembrane domain-deficient STING protein as a high-affinity, stable carrier ($K_d$~73 nM (22)) for cGAMP. Furthermore, while preassembling STINGΔTM with cGAMP, it was observed that this ribonucleoprotein complex is in turn able to tetramerize in response to cGAMP binding to STINGΔTM, forming the essential structure for TBK1 recruitment and downstream signaling (FIG. 1).

cGAMP Binding Induces Near Complete Self-Assembly of STINGΔTM into Tetramers.

Figure 2:
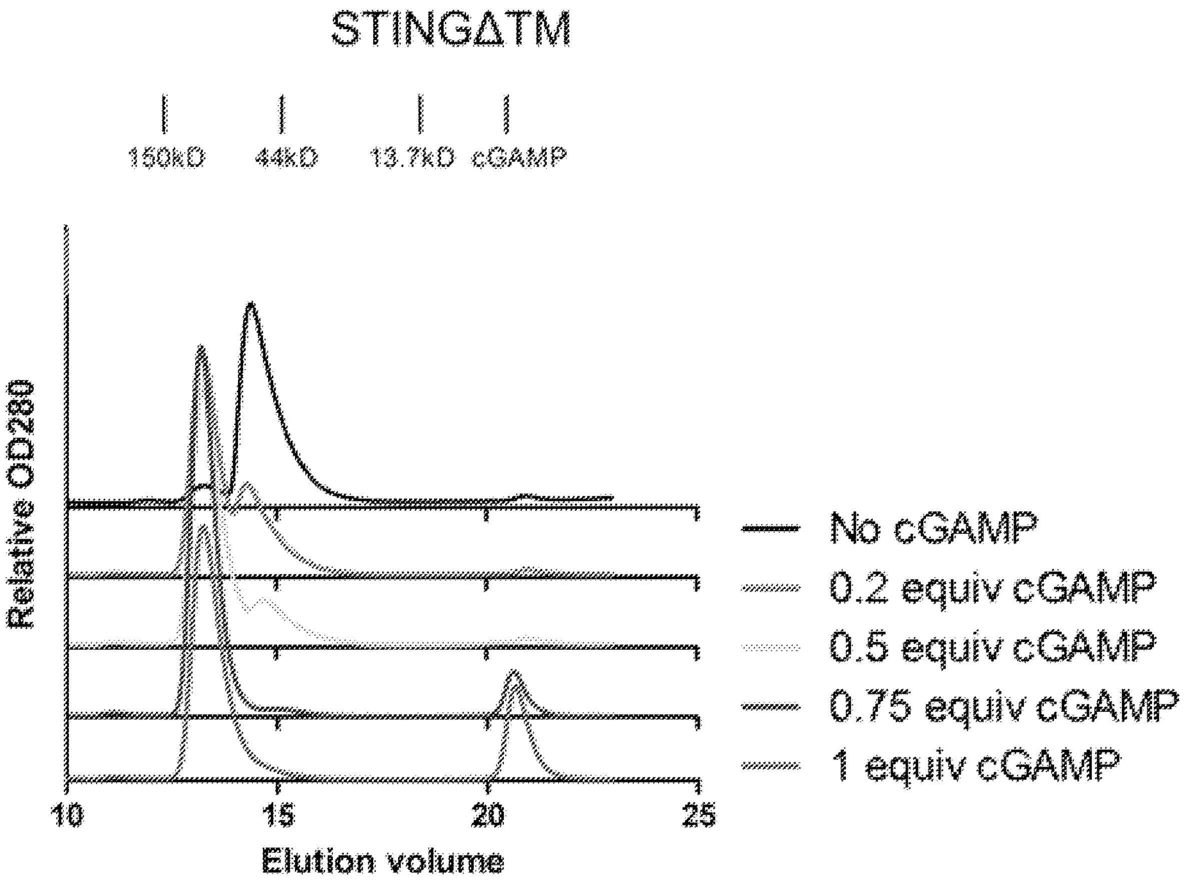
FIG. 2 shows Fast Protein Liquid Chromatography (FPLC) plot demonstrating self-assembly of cGAMP/STINGΔTM tetramer with mouse STINGΔTM in PBS, when the mouse STINGΔTM is titrated with various molar ratios of cGAMP.
Figure 3:
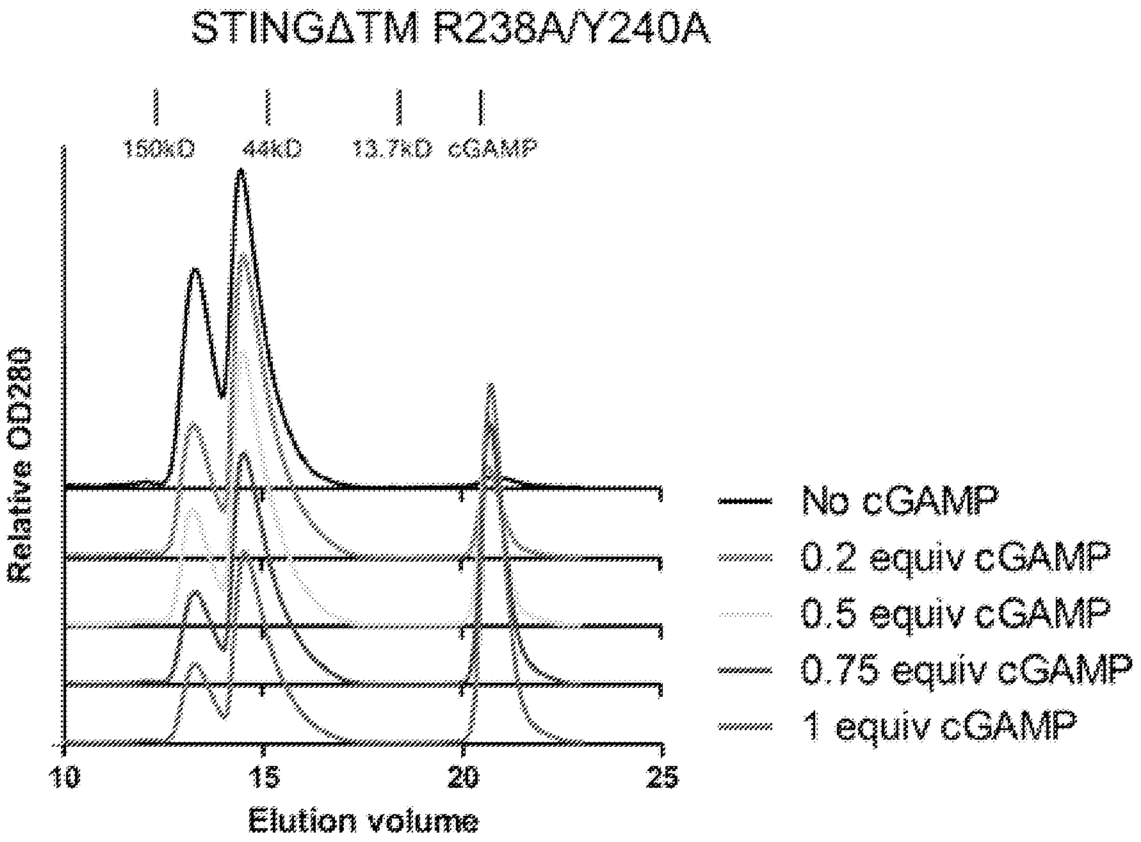
FIG. 3 shows FPLC plot demonstrating low levels of self-assembly of cGAMP/STINGΔTM tetramer with R237A/Y239A mutant STINGΔTM in PBS when the R237A/Y239A mutant STINGΔTM is titrated with various molar ratios of cGAMP.
Figure 4:
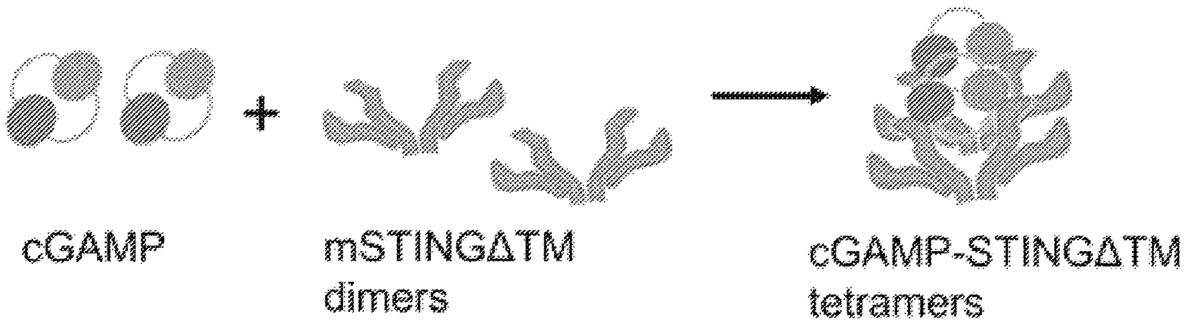
FIG. 4 is a schematic representation of cGAMP-STINGΔTM tetramer self-assembly with mouse STINGΔTM.

To characterize the interaction between cGAMP and STINGΔTM protein, fast protein liquid chromatography (FPLC) analyses was performed in phosphate-buffered saline (PBS), and observed that STINGΔTM (138-378aa) without cGAMP predominantly exist as dimers with an estimated molecular weight of 60 kDa (FIG. 2). STINGΔTM protein was titrated with various molar ratios of cGAMP, incubated the mixture to reach equilibrium, and then injected the mixture through FPLC. While increasing the molar ratio of cGAMP:STINGΔTM, it was observed that the original STINGΔTM dimer population gradually shifting towards another well-defined population with an estimated molecular weight of 120 kDa, suggesting a transition to a tetrameric conformation. No free cGAMP was eluted from FPLC when STINGΔTM were mixed at less than 0.5 molar equivalence of cGAMP. It was only after cGAMP had tetramerized all STINGΔTM, did it start to elute as free cGAMP (FIGS. 2 and 4). It was also observed with transmission electron microscopy (TEM) that STINGΔTM alone in PBS exists as particles ~14 nm in diameter, and when mixed with cGAMP the particle diameters approximately doubled to ~29 nm suggesting the formation of side-by-side tetrameric structures. To verify the role of cGAMP binding in inducing this tetramer self-assembly, a mutant STINGΔTM R238A/Y240A known to abolish the cGAMP binding capability of STING protein was generated. As shown in FIG. 3, STINGΔTM R238A/Y240A showed a partially tetrameric structure independent of cGAMP, but no further self-assembly with increasing amounts of cGAMP titrated.

Additional experiments were conducted with functional double mutants at the tetramer interface (Q272A/A276Q in mouse STINGΔTM). These mutants have been reported to disrupt oligomerization of chicken STING, as well as abolish translocation and puncta formation induced by cGAMP. Surprisingly, the formation of tetrameric structures was observed in the presence of these mutations. While beyond the scope of discussion in this work, these results may raise the possibility of a cGAMP-induced ΔTM tetrameric structure distinct from the WT STING oligomers studied in literature.

It has been reported that STING moves from the ER and aggregates via oligomerization of the cytosolic C-terminus domain (CTD) following its activation by cGAMP. This aggregation is essential for the binding and phosphorylation of TBK1, which subsequently phosphorylates IRF3 and initiates the downstream pathway. Recent structural analyses of the STING-TBK1 protein complex revealed that due to geometric constraints, the S366 of STING cannot be phosphorylated by the same TBK1 dimer it is bound to; instead, it interacts with the kinase site of the neighboring TBK1. Hence, a minimum of two neighboring dimers—a tetrameric structure—is needed for successful signaling. It was also found that after full-length STING in cells binds cGAMP, they form side-by-side tetramers that could assemble into larger oligomers to facilitate this transphosphorylation. It was observed that cells overexpressing STINGΔTM do not exhibit this clustering of STINGΔTM molecules upon addition of cGAMP—the protein is evenly distributed in the cytosol, as the N-terminus domain (NTD) which modulates the translocation from the ER is missing. However, when the tetramerized STINGΔTM protein with cGAMP was directly delivered via a commercial transfection reagent into cells, the clustering behavior of the STINGΔTM protein that is essential for IFN signaling was observed. This was corroborated by in vitro activation tests of STING signaling, the details of which are discussed in the following section. It was therefore hypothesized that the cGAMP-STINGΔTM tetrameric signaling complex created in the pre-assembly process was the pivotal factor for successful IFN signaling in cells.

cGAMP-STINGΔTM Results in Enhanced Type I IFN Signaling In Vitro

Figure 5:
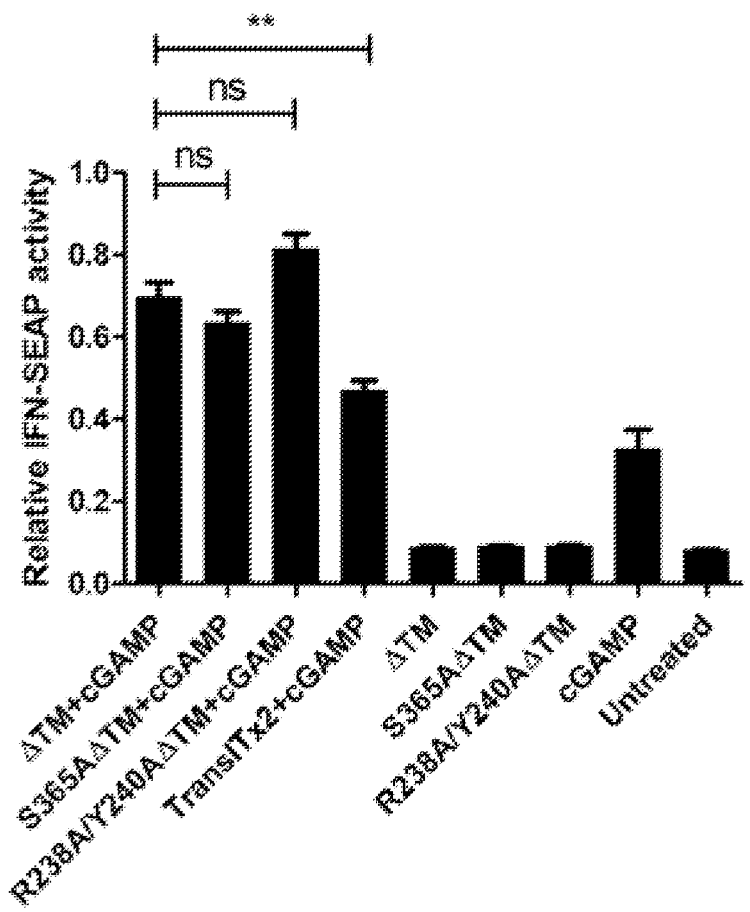
FIG. 5 is a plot demonstrating immunoblotting of endogenous expression of STING, TBK1, and IRF3 in HEK293T cell line treated with different combinations/mutations of cGAMP/STINGΔTM tetramer (10 μg of STINGΔTM with 0.25 μg of cGAMP per milliliter). Luciferase and single enzyme activity-based protein profiling (SEAP) activity were determined 24 hours after treatment. Values are reported as means±SEM. *$P<0.001$, $P<0.01$, and *$P<0.05$, as analyzed by one-way analysis of variance (ANOVA).

Unless otherwise specified, human STINGΔTM was used for all HEK293T cell in vitro IFN activation tests and mouse STINGΔTM for all remaining studies. In figure legends, all proteins delivered in vitro and in vivo (denoted as ΔTM or mutants such as S365AΔTM) are referred to as STINGΔTM proteins, and all cGAMP co-delivery groups comprise 1:1 molar equivalents of cGAMP:STINGΔTM. To verify the signaling efficacy of the cGAMP-STINGΔTM tetramer, they were first delivered to a mouse macrophage cell line RAW264.7 that has endogenous STING expression. Overall, it was observed that the vehicle-free groups elicited higher interferon expression than the groups with commercial transfection reagent, and that in both groups, cGAMP co-delivery with STINGΔTM resulted in higher interferon expression than cGAMP delivered alone (FIG. 5). Interestingly, in the presence of endogenous STING, mutant versions of cGAMP-STINGΔTM (S365A and R238A/Y240A) are as effective as the wild type protein, suggesting that S365A and R238A/Y240A mutants may act as chaperones to shuttle cGAMP into cells while utilizing endogenous wild-type (WT) STING for activation of STING signaling.

The efficacy of cGAMP-STINGΔTM tetramer in an interferon-luciferase reporter cell line HEK293T, which was deficient in endogenous STING expression but express other essential proteins for the STING signaling pathway including TBK1 and IRF3 was then tested. This cell line was generated by integrating an interferon-stimulated response element (ISRE) that drives expression of luciferase in HEK293T cells. In addition, three functional STINGΔTM mutants S366A, R238A/Y240A, and ΔC9 (deleting 9 amino acids from the C-terminus tail)—which are known to abrogate STING phosphorylation, cGAMP binding, and TBK1 binding, respectively—were included, and the results confirmed that the STINGΔTM protein is indeed functional in triggering the STING pathway independent of endogenous STING (FIG. 6).

Figure 6:
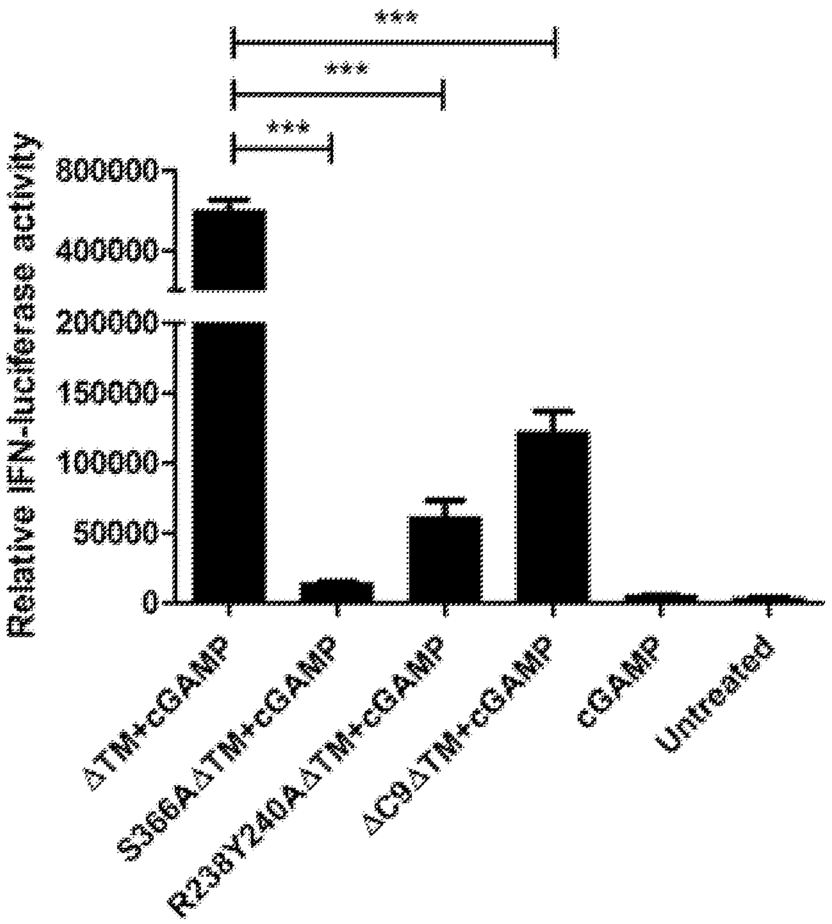
FIG. 6 is a plot demonstrating immunoblotting of endogenous expression of STING, TBK1, and IRF3 in RAW264.7 cell lines treated with different combinations/mutations of cGAMP/STINGΔTM tetramer (10 μg of STINGΔTM with 0.25 μg of cGAMP per milliliter). Luciferase and SEAP activity were determined 24 hours after treatment. Values are reported as means±SEM. *$P<0.001$, $P<0.01$, and *$P<0.05$, as analyzed by one-way ANOVA.
Figure 7:
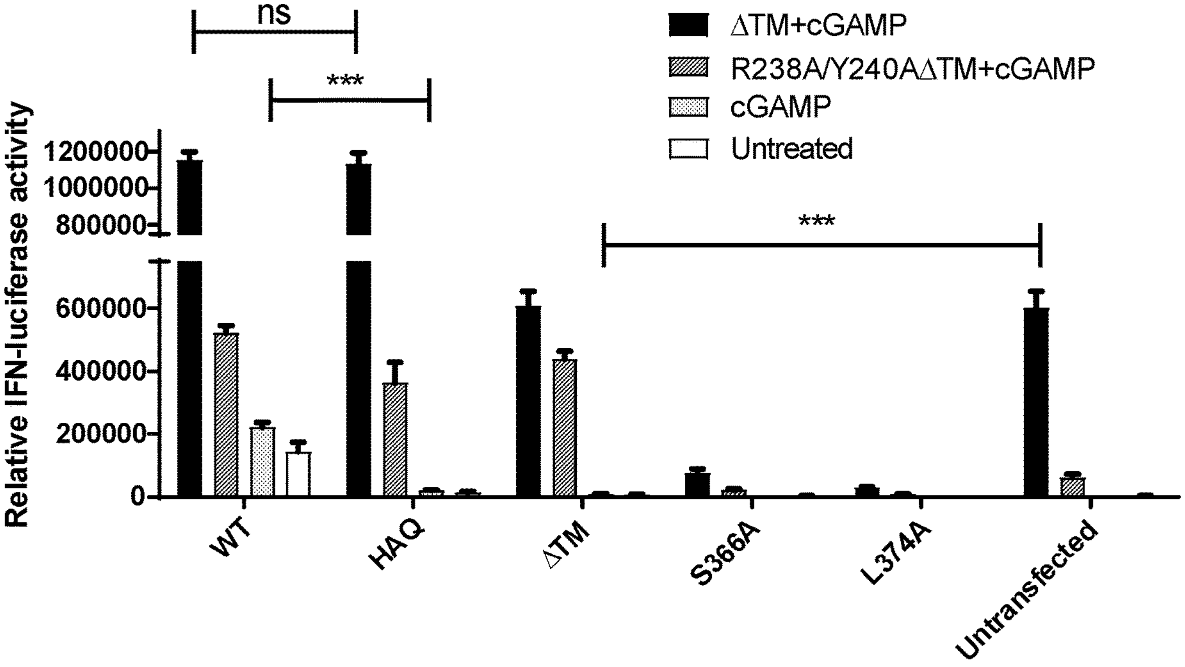
FIG. 7 shows a plot demonstrating luciferase activity in transfected HEK293T cells (n=4) treated with cGAMP/STINGΔTM tetramer (plus R238A/Y240A mutant), cGAMP only, and 10 μg of STINGΔTM with 0.25 μg of cGAMP per milliliter. Luciferase activity were determined 24 hours after treatment. Values are reported as means±SEM. *$P<0.001$, $P<0.01$, and *$P<0.05$, as analyzed by one-way ANOVA.

Although the axes of FIGS. 5 and 6 are not directly comparable due to the use of two different interferon reporters (raw ISG blue for the RAW264.7 cell line and luciferase for the HEK293T cell line), it is apparent that in both cases, IFN activity is increased via the co-delivery of cGAMP with STINGΔTM. And while there visually appears to be a far larger difference in IFN activity between the cGAMP and STINGΔTM+cGAMP group in the HEK293T system, this is due to the lack of endogenous STING in the HEK293T cell line, leading to a negligible amount of IFN activity. Conversely, this difference is less pronounced in the RAW264.7 system due to the presence of endogenous STING, which leads to measurable IFN-SEAP activity in the cGAMP-only group (as it is able to function with endogenous STING).

The interferon activity of additional small-molecule agonists using cdiGMP and cGAM(PS)$_2$—a synthetic, non-degradable cGAMP analog—were also evaluated as previously described in the HEK293T system. The system exhibited behavior similar to that of the cGAMP+STINGΔTM co-delivery group, namely that the co-delivery of STINGΔTM with these agonists resulted in increased interferon activity relative to all functional mutants tested and agonist-only controls. These studies suggest that the recombinant protein STINGΔTM-mediated enhanced type I IFN signaling derives from the preassembly of agonist and STINGΔTM, and is independent of cell type or CDN species.

Figure 8:
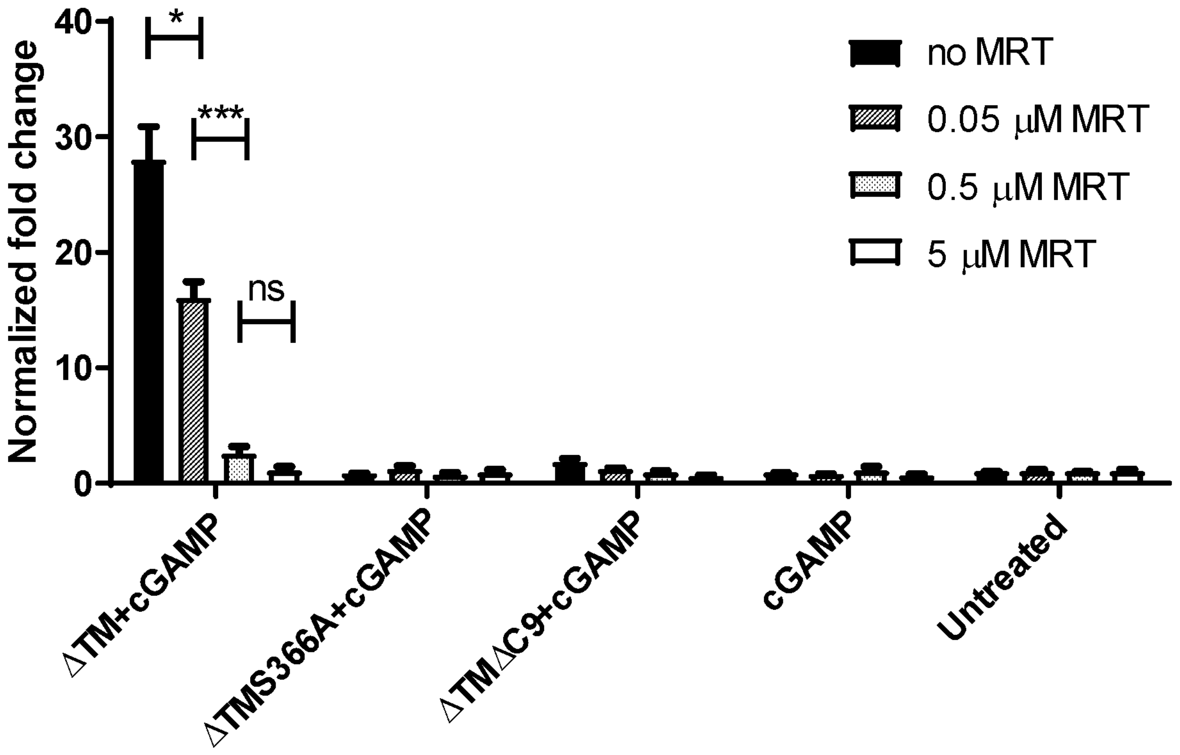
FIG. 8 shows a plot demonstrating interferon activity change in HEK293T cells (n=4) pretreated with TBK1 inhibitor MRT67307 (MRT) and then treated with different combinations/mutations of cGAMP/STINGΔTM tetramer. Values are reported as means±SEM. *$P<0.001$, $P<0.01$, and *$P<0.05$, as analyzed by one-way ANOVA.
Figure 9:
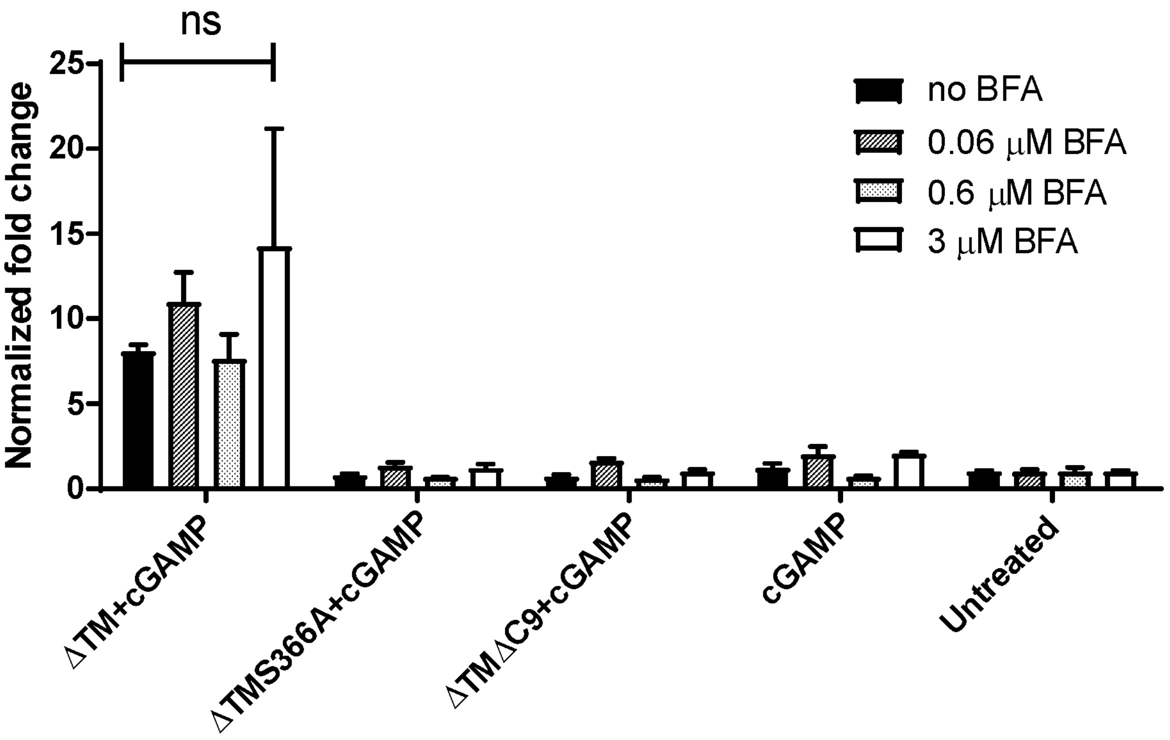
FIG. 9 shows a plot demonstrating interferon activity change in HEK293T cells (n=4) pretreated with BFA, which blocks ER-Golgi trafficking and then treated with different combinations/mutations of cGAMP/STINGΔTM tetramer. Values are reported as means±SEM. *$P<0.001$, $P<0.01$, and *$P<0.05$, as analyzed by one-way ANOVA.

Finally, several chemical inhibitors including MRT67307 (MRT), brefeldin A (BFA), chloroquine (CQ), and bafilomycin A1 (BafA1) were used to comprehensively dissect the intracellular trafficking of the tetrameric complex through confocal microscopy and quantification of interferon activity: at 6 h post-transfection, limited co-localization of STINGΔTM with Early Endosome Antigen 1 (EEA1), an early endosome marker, was observed suggesting potential escape of the early endosome into the cytosol. Interferon activity was observed to decrease with increasing concentrations of MRT (TBK1 inhibitor), which indicates that the STING signaling does proceed via a TBK1-dependent pathway (FIG. 8). Additionally, confocal microscopy images (also taken 6 h post-transfection) confirmed the co-localization of TBK1 with STINGΔTM in punctate structures that resemble those formed by cGAMP-activated full-length STING. Interactions with IRF3 has previously been shown by coimmunoprecipitation of STINGΔTM with phosphorylated IRF3. Interestingly, the presence of BFA—an inhibitor of ER-Golgi protein trafficking previously shown to block the full-length STING-induced IRF pathway—appeared to have an insignificant effect on STINGΔTM-induced STING signaling (FIG. 9). This was corroborated by no significant evidence of STINGΔTM co-localization with the Golgi apparatus with or without the addition of BFA, a markedly different phenomenon from literature reports of full-length STING localization with ERGIC disruptors.

Another departure from similar assays on full-length STING was observed upon treatment of the cells with BafA1, an autophagy inhibitor. Interferon activity was found to be significantly dependent on the concentration of BafA1, with decreasing activity observed with increasing concentrations of BafA1, which could suggest the necessity of autophagosome-lysosome fusion in STINGΔTM-induced STING signaling. The eventual degradation of STINGΔTM via a lysosomal pathway was observed in its co-localization with Lysosomal Associated Membrane Protein 1 (LAMP1) at 24 h post-transfection which was not apparent at 6 h post-transfection. This was consistent with the increased interferon activity observed upon incubation with increasing concentrations of CQ (an inhibitor of lysosomal enzymes), as had been reported in literature with full-length STING.

While in the literature there are mixed reports on HAQ sensitivity to STING agonists relative to WT STING, it was assessed whether co-delivery of STINGΔTM and cGAMP can enhance IFN in HAQ-transfected cells in comparison to cGAMP only treatment in HEK293T cells, which lack endogenous STING. HEK293T cells were transiently transfected with plasmid DNA encoding a full-length human STING (WT, 1-379aa) or the HAQ allele, as a means to simulate cells with fully functioning STING and defective STING. Meanwhile, S366A (1-379aa), L374A (1-379a) and STINGΔTM (139-379aa) were also expressed separately in 293T as negative controls. Those cells with various defective STINGs were then treated with cGAMP-STINGΔTM tetramers, cGAMP mixed with STINGΔTM (R238A/Y240A) or cGAMP only. Cells overexpressing HAQ STING were significantly less responsive to conventional cGAMP administration than cells expressing WT STING. Cells overexpressing STINGΔTM also did not result in significant interferon activity upon delivery of cGAMP only, a phenomenon previously reported in literature. However, when cGAMP was delivered in the form of cGAMP-STINGΔTM tetramers, both cells overexpressing HAQ STING and WT STING showed equally high levels of IFN expression. Increased IFN expression was also observed in cells overexpressing STINGΔTM. Untransfected cells likewise exhibited significantly higher interferon activity upon co-delivery of the cGAMP-STINGΔTM tetramers when compared to cGAMP-only controls in untransfected cells and cells overexpressing WT STING. Therefore, it has been demonstrated that the method could potentially address the issue of STING heterogeneity in humans through the co-delivery of cGAMP with a functional STINGΔTM carrier.

To conclude the in vitro characterization of the STINGΔTM-cGAMP tetrameric complex, the expression of IFN-β, TBK1, and IRF3 in RAW264.7 and DC2.4 cell lines via qPCR, as a means of better understanding the effect of the delivery system on STING signaling intermediates, was evaluated. At 6 h post-treatment with cGAMP-STINGΔTM, a slight enhancement in TBK1, but not in IRF3 expression was observed. Overall, delivery of cGAMP-STINGΔTM significantly increased the expression of IFN-β relative to cGAMP only and STINGΔTM only controls in both cell lines tested, demonstrating the capability of the system to achieve enhanced STING signaling in the presence of endogenous STING.

cGAMP-STINGΔTM Induces Dendritic Cell Maturation and Strong Humoral and Cellular Immune Responses In Vivo.

Figure 10:
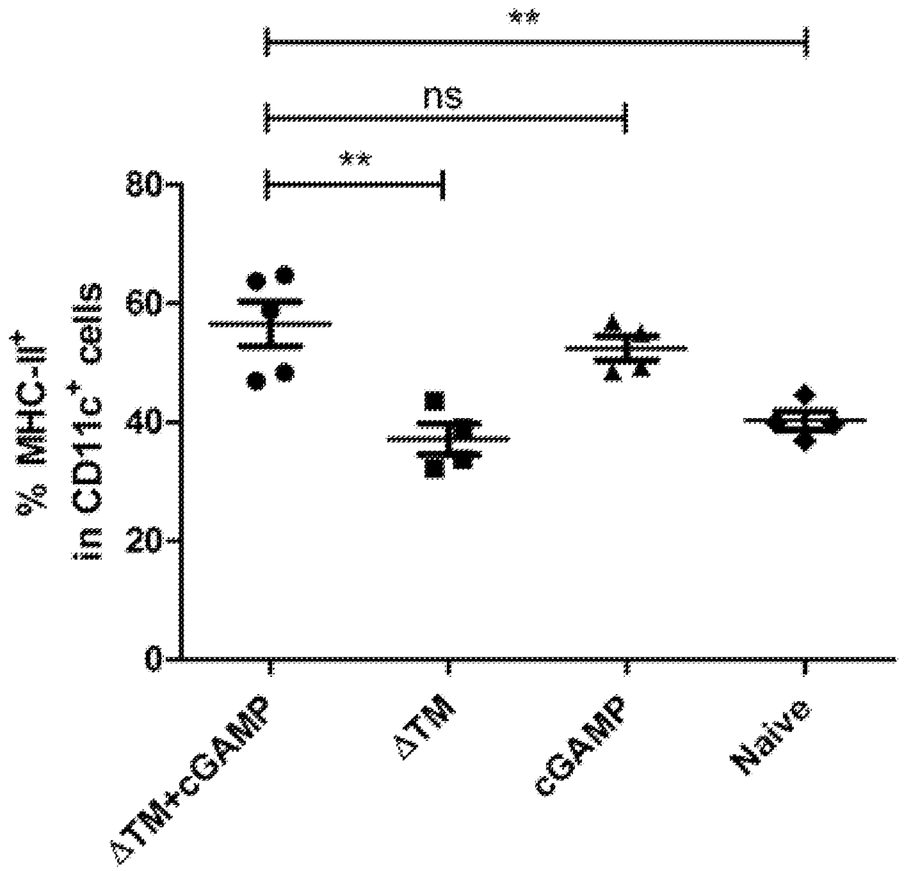
FIG. 10 shows a plot demonstrating dendritic cell activation in draining (inguinal lymph node) gated by % MHC-II$^+$ cells in CD11c$^+$ cells. Groups of C57BL/6 mice (n=4) were tail base injected with 40 μg of STINGΔTM, with or without 1 μg of cGAMP, or 1 μg of cGAMP alone on day 0, and then on day 1.5, draining (inguinal) lymph node lymphocytes were collected for analysis by flow cytometry. Values are reported as means±SEM. *P<0.001, P<0.01, and *P<0.05, as analyzed by one-way ANOVA.

To explore its application to boost the adjuvanticity potential of STING agonists (e.g. cGAMP), the influence of cGAMP-STINGΔTM on dendritic cell (DC) maturation in vitro and in vivo was first confirmed. In brief, the expression of IFN-β in DCs 6 h post-treatment with cGAMP-STINGΔTM was analyzed and a significant increase in expression levels relative to cGAMP only and STINGΔTM controls was found. The effect of the tetramers on DC maturation in vivo following the treatment of C57BL/6 mice was also confirmed, where significant upregulation of the DC maturation marker MHC-Ir in $CD11c^+$ cells in the cGAMP-STINGΔTM trial compared to STINGΔTM and naïve controls was observed (FIG. 10).

Figure 11:
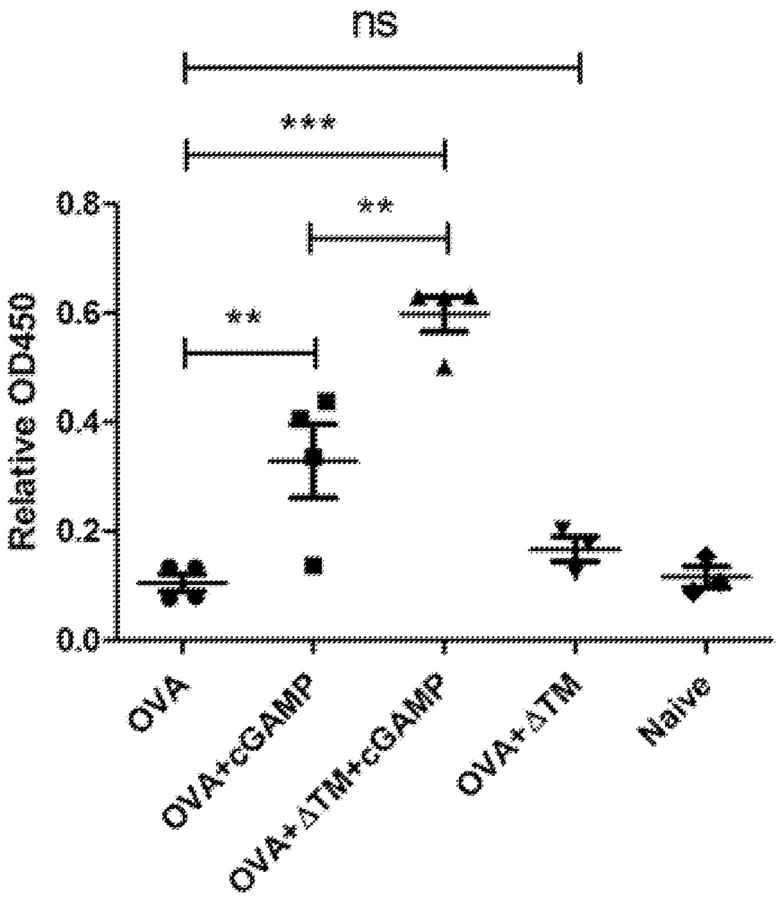
FIG. 11 shows a plot demonstrating IgG-based antigen-specific immune response after 14 days. C57BL/6 mice (n=4) were immunized with 10 μg of ovalbumin (OVA) alone or OVA mixed with 2.5 μg of cGAMP or 100 μg of STINGΔTM or both via tail base injection on days 0 and 7. On day 14 OVA-specific total immunoglobulin G (IgG) antibody level in mouse serum was measured via enzyme-linked immunosorbent assay (ELISA). Values are reported as means±SEM. *P<0.001, P<0.01, and *P<0.05, as analyzed by one-way ANOVA.
Figure 12:
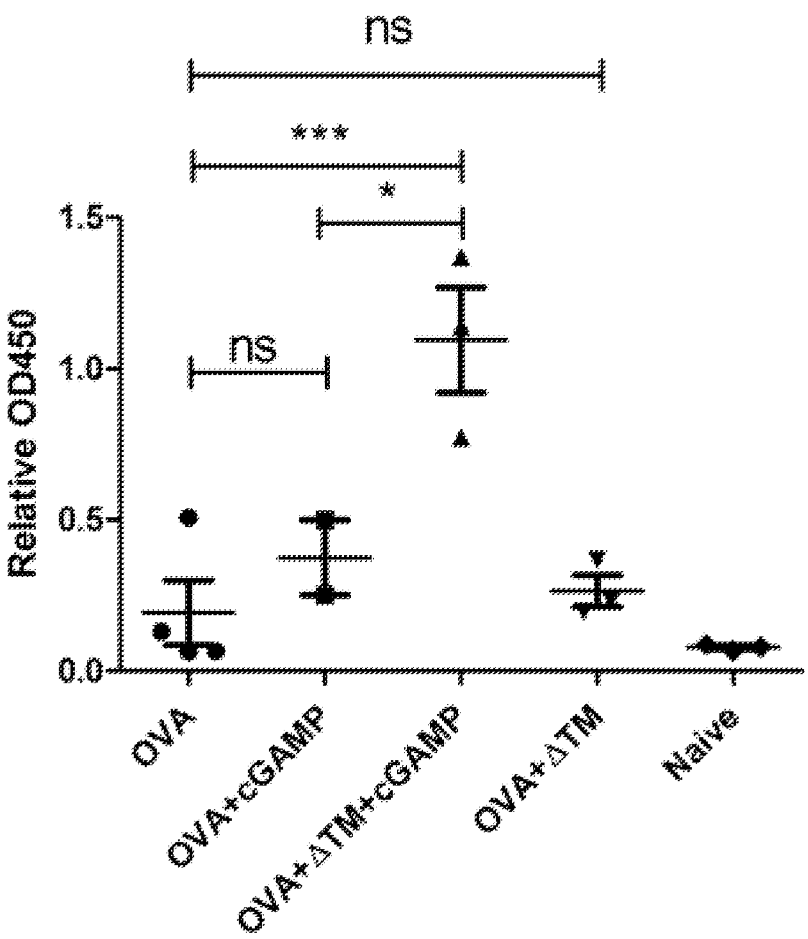
FIG. 12 shows a plot demonstrating IgG-based antigen-specific immune response after 28 days according to the protocol described for FIG. 11. Five mice were lost because of accidental cage flooding. Values are reported as means±SEM. *P<0.001, P<0.01, and *P<0.05, as analyzed by one-way ANOVA.
Figure 13:
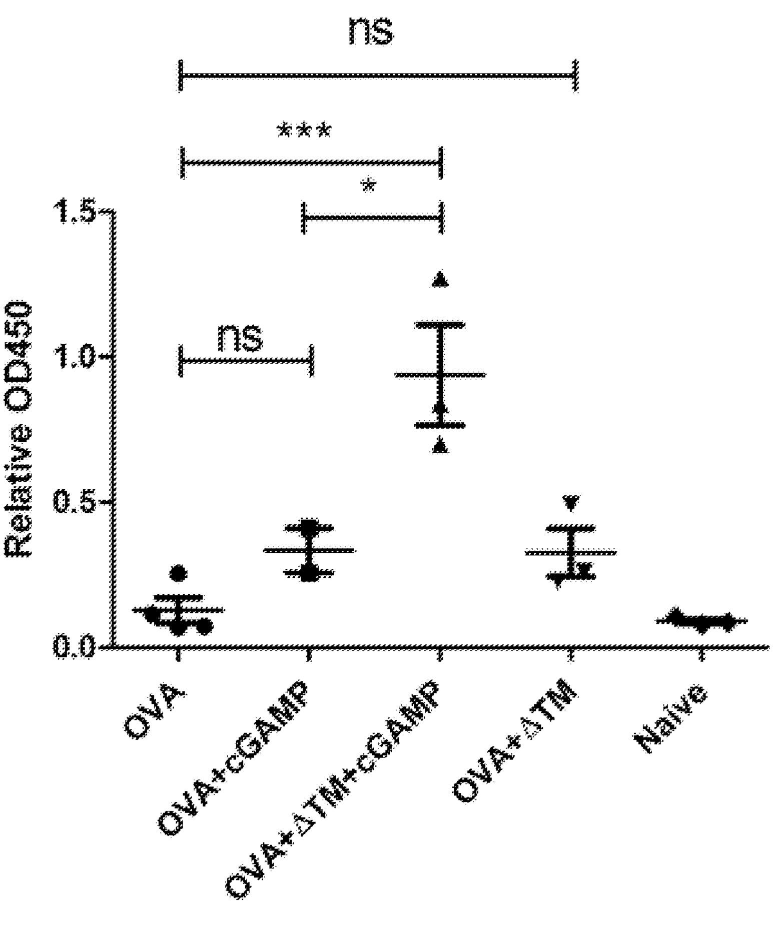
FIG. 13 shows a plot demonstrating IgG-based antigen-specific immune response after 42 days according to the protocol described for FIG. 11. Five mice were lost because of accidental cage flooding.*P<0.001, P<0.01, and *P<0.05, as analyzed by one-way ANOVA.
Figure 14:
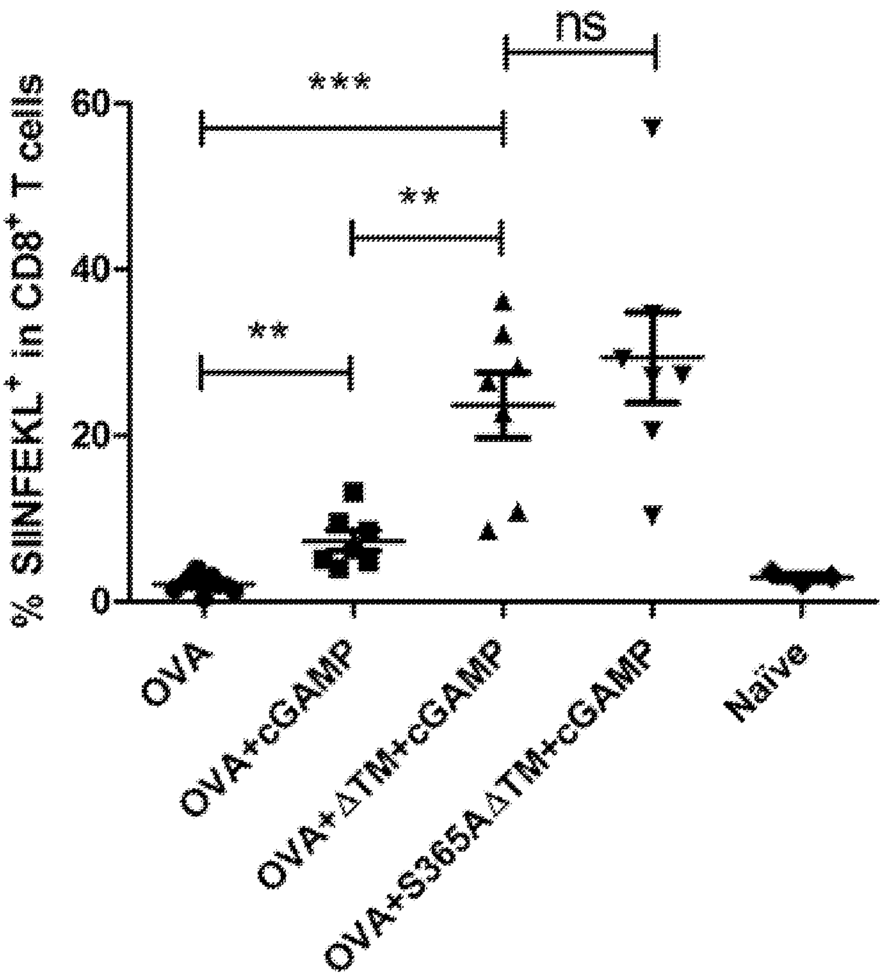
FIG. 14 shows a plot demonstrating the effect of immunization of groups of C57BL/6 mice (n=7) with 50 μg of OVA alone or OVA mixed with 1 μg of cGAMP or 40 μg of STINGΔTM (or 40 μg of S365A STINGΔTM) on days 0 and 7. On day 14, PBMCs were collected and CD8+ T cells were analyzed by CD8 OVA epitope SIINFEKL tetramer staining Values are reported as means±SEM. *P<0.001, P<0.01, and *P<0.05, as analyzed by one-way ANOVA.
Figure 15:
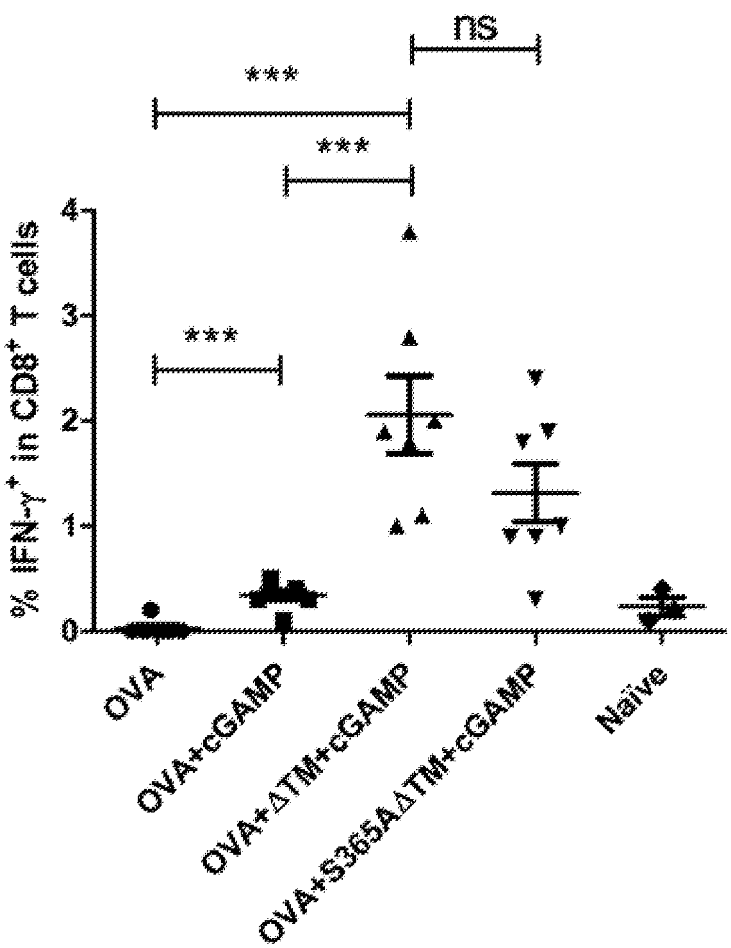
FIG. 15 shows a plot demonstrating the effect of immunization of groups of C57BL/6 mice u. On day 14, PBMCs were collected and CD8$^+$ T cells were stimulated ex vivo with CD8 OVA epitope SIINFEKL and analyzed by intracellular cytokine staining of IFN-γ. Values are reported as means±SEM. *P<0.001, P<0.01, and *P<0.05, as analyzed by one-way ANOVA.
Figure 16:
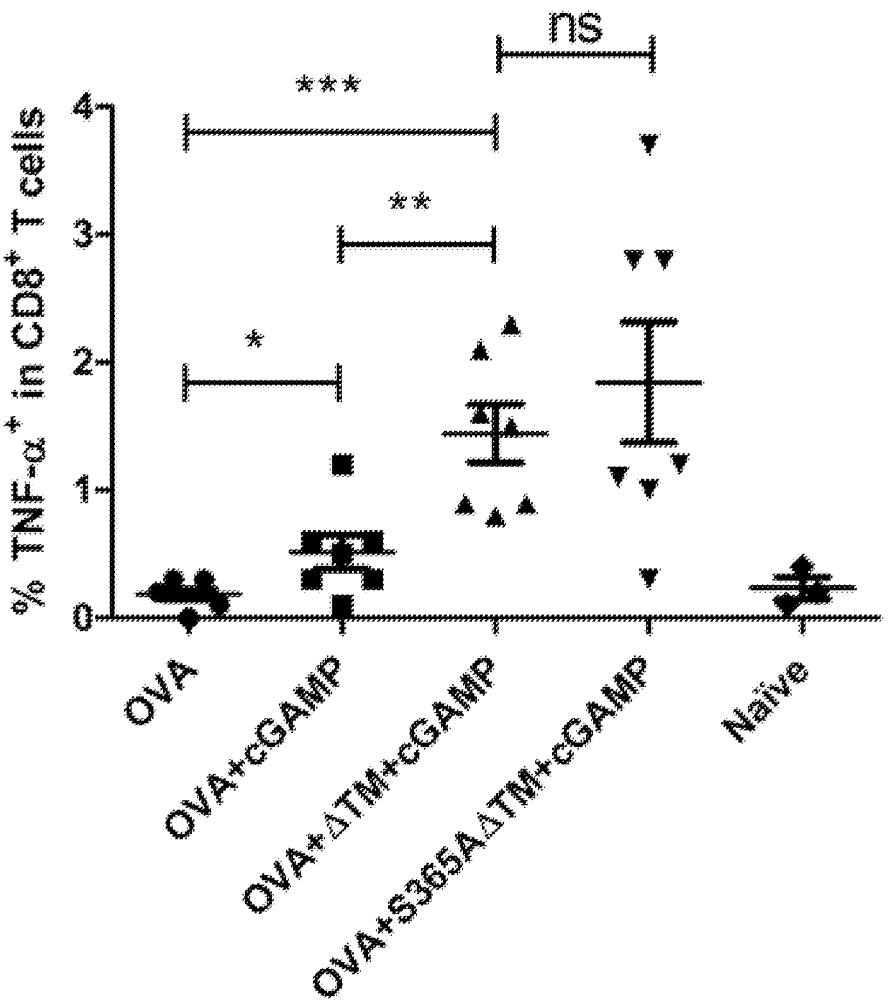
FIG. 16 shows a plot demonstrating the effect of immunization of groups of C57BL/6 mice (n=7) with 50 μg of OVA alone or OVA mixed with 1 μg of cGAMP or 40 μg of STINGΔTM (or 40 μg of S365A STINGΔTM) on days 0 and 7. On day 14, PBMCs were collected and CD8+ T cells were stimulated ex vivo with CD8 OVA epitope SIINFEKL and analyzed by intracellular cytokine staining of TNF-α. Values are reported as means±SEM. *P<0.001, P<0.01, and *P<0.05, as analyzed by one-way ANOVA.
Figure 17:
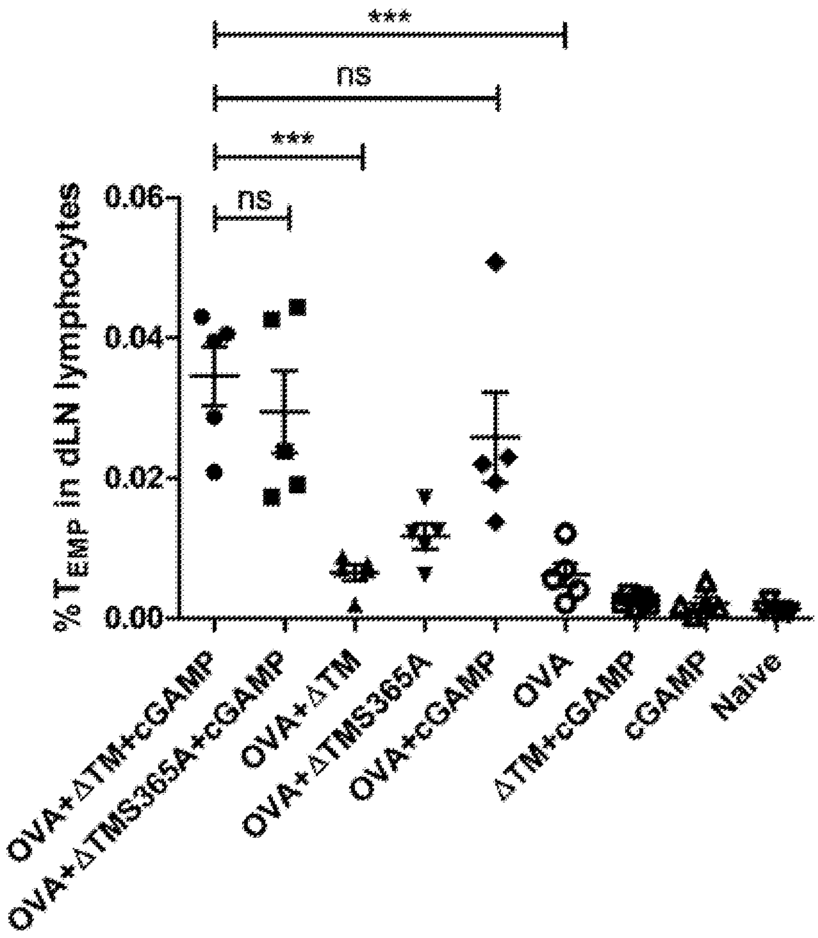
FIG. 17 shows a plot demonstrating the effect of immunization of groups of C57BL/6 mice (n=5) were immunized with 50 μg of OVA alone or OVA mixed with 1 μg of cGAMP or 40 μg of STINGΔTM (or 40 μg of S365A STINGΔTM) on days 0 and 14. On day 21, PBMCs and lymphocytes in dLN and splenocytes were collected and CD8+ T cells were analyzed by CD8 OVA epitope SIINFEKL tetramer staining. Among CD8$^+$ SIINFEKL tetramer$^+$ T cells, effector memory precursors TEMP were gated by CD27$^+$ CD62L$^-$ and KLRG1$^-$ in dLN lymphocytes. Values are reported as means±SEM. *P<0.001, P<0.01, and *P<0.05, as analyzed by one-way ANOVA.
Figure 18:
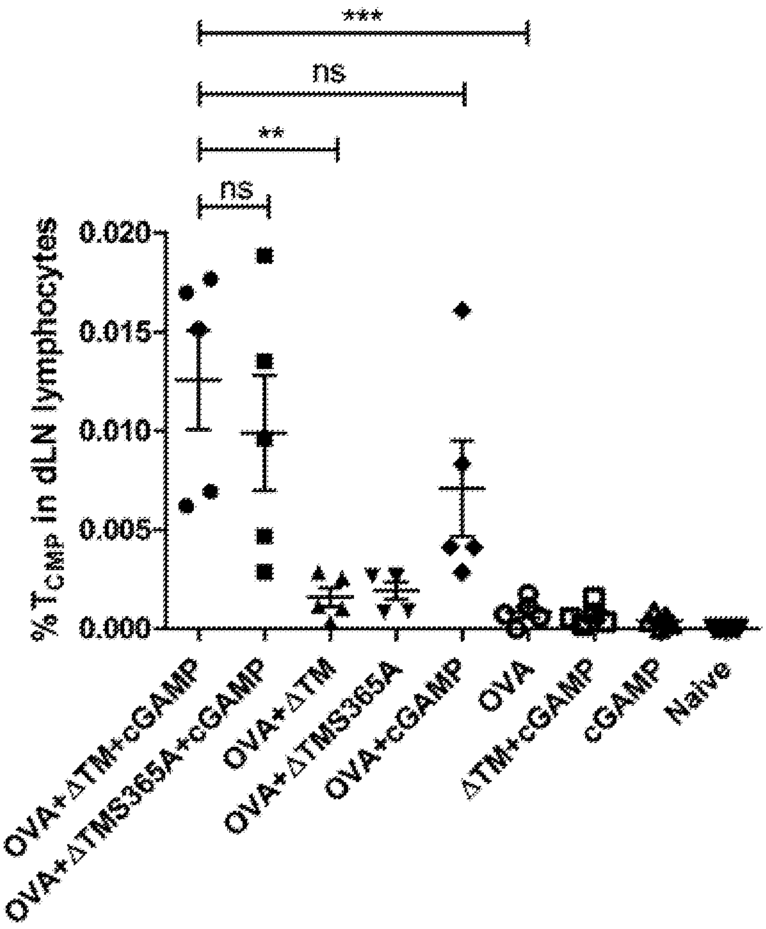
FIG. 18 shows a plot demonstrating the effect of immunization of groups of C57BL/6 mice (n=5) were immunized with 50 μg of OVA alone or OVA mixed with 1 μg of cGAMP or 40 μg of STINGΔTM (or 40 μg of S365A STINGΔTM) on days 0 and 14. On day 21, PBMCs and lymphocytes in dLN and splenocytes were collected and CD8+ T cells were analyzed by CD8 OVA epitope SIINFEKL tetramer staining. Among CD8$^+$ SIINFEKL tetramer$^+$ T cells, effector memory precursors TEMP were gated by CD27+ CD62L$^-$ and KLRG1$^-$, and central memory precursors TCMP were gated by CD27+ CD62L+ and KLRG1− in dLN lymphocytes. Values are reported as means±SEM. *P<0.001, P<0.01, and *P<0.05, as analyzed by one-way ANOVA.
Figure 19:
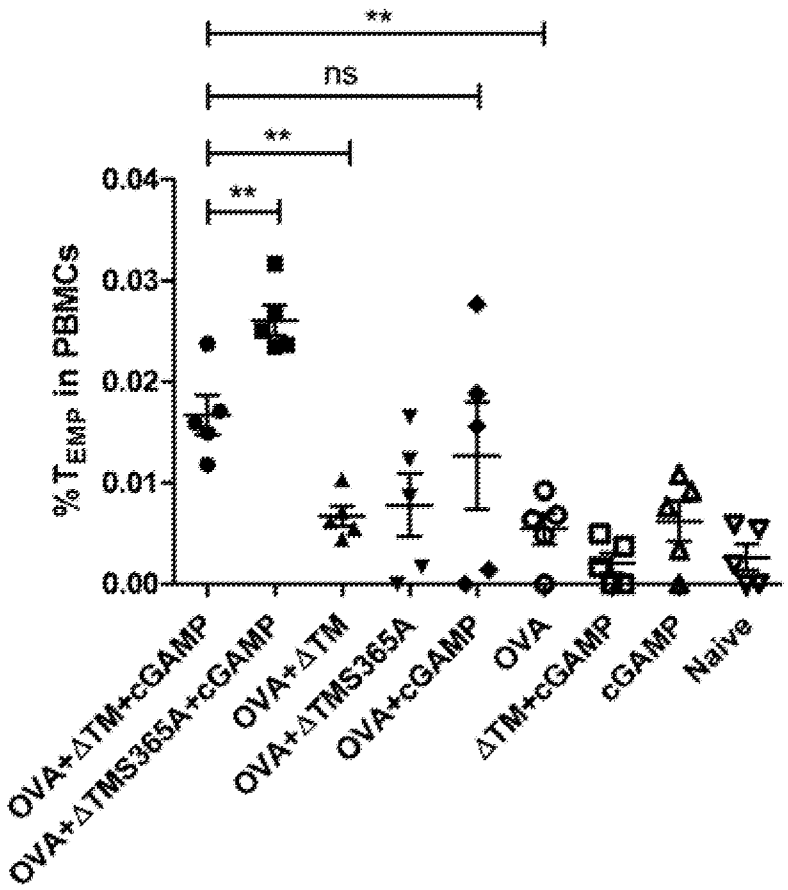
FIG. 19 shows a plot demonstrating the effect of immunization of groups of C57BL/6 mice (n=5) were immunized with 50 μg of OVA alone or OVA mixed with 1 μg of cGAMP or 40 μg of STINGΔTM (or 40 μg of S365A STINGΔTM) on days 0 and 14. On day 21, PBMCs and lymphocytes in dLN and splenocytes were collected and CD8+ T cells were analyzed by CD8 OVA epitope SIINFEKL tetramer staining. Among CD8$^+$ SIINFEKL tetramer$^+$ T cells, effector memory precursors TEMP were gated by CD27$^+$ CD62L$^-$ and KLRG1$^-$ in PBMCs. Values are reported as means±SEM. *P<0.001, P<0.01, and *P<0.05, as analyzed by one-way ANOVA.
Figure 20:
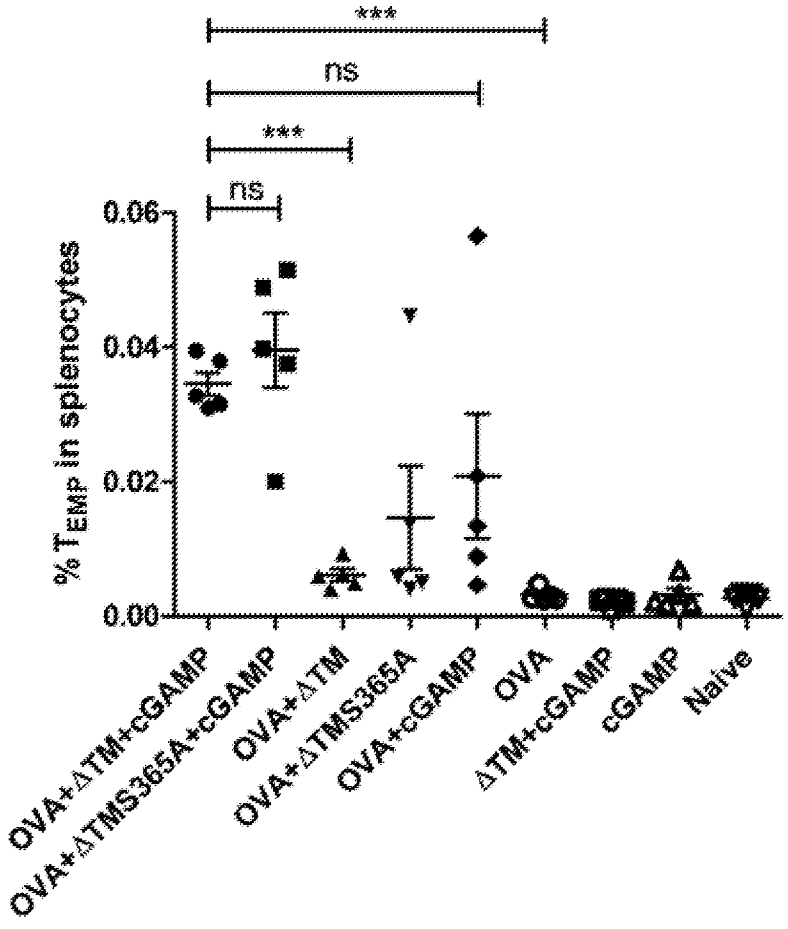
FIG. 20 shows a plot demonstrating the effect of immunization of groups of C57BL/6 mice (n=5) that were immunized with 50 μg of OVA alone or OVA mixed with 1 μg of cGAMP or 40 μg of STINGΔTM (or 40 μg of S365A STINGΔTM) on days 0 and 14. On day 21, PBMCs and lymphocytes in dLN and splenocytes were collected and CD8+ T cells were analyzed by CD8 OVA epitope SIINFEKL tetramer staining. Among CD8$^+$ SIINFEKL tetramer$^+$ T cells, effector memory precursors TEMP were gated by CD27$^+$ CD62L$^-$ and KLRG1$^-$ in splenocytes. Values are reported as means±SEM. *P<0.001, P<0.01, and *P<0.05, as analyzed by one-way ANOVA.
Figure 21:
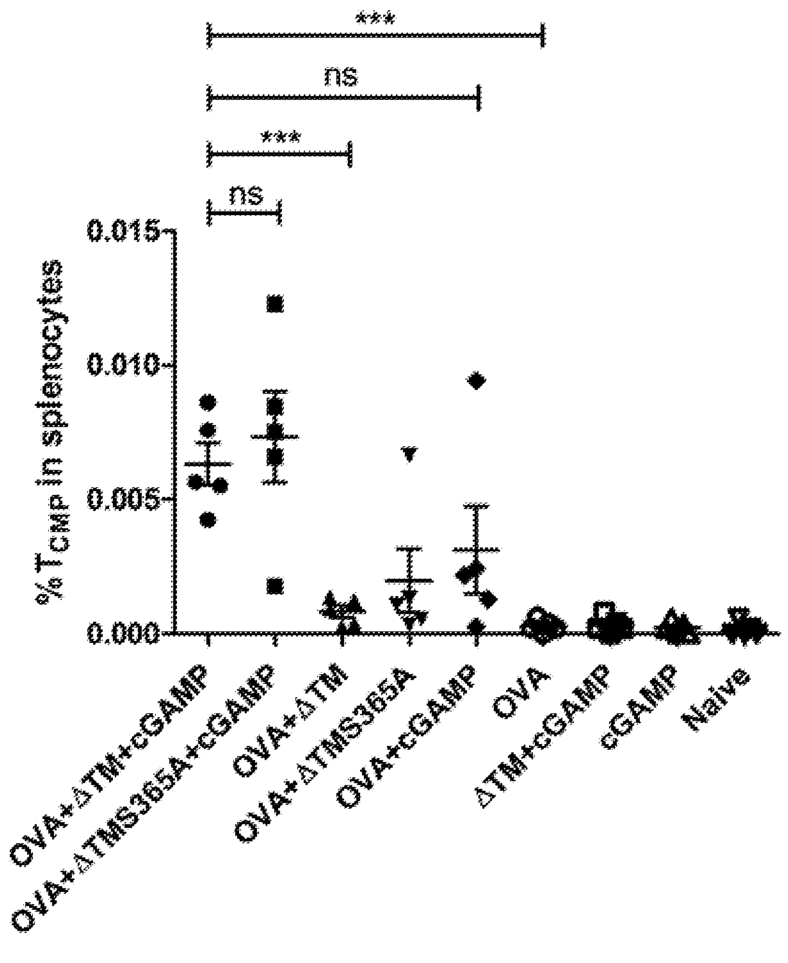
FIG. 21 shows a plot demonstrating the effect of immunization of groups of C57BL/6 mice (n=5) that were immunized with 50 μg of OVA alone or OVA mixed with 1 μg of cGAMP or 40 μg of STINGΔTM (or 40 μg of S365A STINGΔTM) on days 0 and 14. On day 21, PBMCs and lymphocytes in dLN and splenocytes were collected and CD8+ T cells were analyzed by CD8 OVA epitope SIINFEKL tetramer staining. Among CD8$^+$ SIINFEKL tetramer$^+$ T cells, effector memory precursors TEMP were gated by CD27+ CD62L$^-$ and KLRG1$^-$, and central memory precursors TCMP were gated by CD27+ CD62L+ and KLRG1− in splenocytes. Values are reported as means±SEM. *P<0.001, P<0.01, and *P<0.05, as analyzed by one-way ANOVA.

The humoral immune response elicited against OVA antigens with or without the STING-cGAMP adjuvant was then evaluated. Five groups of C57BL/6 mice were immunized on day 0 and boosted on day 7 with 10 μg OVA alone, or OVA mixed with 2.5 cGAMP and/or 100 μg STINGΔTM via tail base injection. On day 14, 28, and 42, sera were collected for enzyme-linked immunosorbent assay (ELISA) to determine the anti-OVA total IgG level. The groups vaccinated with the combination of OVA+cGAMP+STINGΔTM generated a significantly more robust and sustained total IgG-based antigen-specific immune response compared to other control groups (FIGS. 11-13). Additional experiments also demonstrated that no systemic toxicity occurred from tetramer delivery, specifically that there was no significant increase in the level of inflammatory cytokines (IL-6 and TNF-α) when compared to the injection of PBS. Release of cGAMP-STINGΔTM from the tail base was also sustained for over a week, with trafficking to the draining (inguinal) lymph nodes that was 20-50 fold higher than in either STINGΔTM-only or cGAMP-only controls.

The antigen-specific T cell activation via tetramer and intracellular cytokine staining of peripheral blood mononuclear cells (PBMCs) was then quantified. Groups of C57BL/6 were immunized on day 0 and boosted on day 7 via tail base injection with 50 μg OVA alone, or OVA mixed with 1 μg cGAMP and/or 40 μg STINGΔTM (or 40 μg S365A STINGΔTM). On day 14, mice were bled and PBMCs were separated from the whole blood. For tetramer staining PBMCs were stained with anti-CD8 antibody and H-$2K^b$/SIINFEKL tetramer. For intracellular cytokine staining, cells were first stimulated with SIINFEKL peptide. They were then stained with anti-CD8 antibody and permeabilized for intracellular cytokine staining of TNF-α and IFN-γ. FIG. 9 shows that antigen delivered with both STINGΔTM and S365AΔTM plus cGAMP significantly increased the percentage of $SIINFEKL^+$ and both TNF-α- and IFN-γ-secreting $CD8^+$ T cells, which indicates that the tetramers resulted in successful IFN induction in T cells and is consistent with the in vitro STING signaling activation tests with RAW264.7 cells.

Finally, the induction of memory T cell response through the use of model antigen OVA was investigated. Groups of C57Bl/6 mice were immunized on day 0 and boosted on day 14 via tail base injection with 50 μg OVA alone, or OVA mixed with 1 μg cGAMP and/or 40 μg STINGΔTM (or 40 μg S365A STINGΔTM). On day 21, mice were sacrificed to harvest lymphocytes from the draining lymph nodes (dLN, inguinal) and splenocytes. As shown in FIGS. 17-21, the delivery of cGAMP-STINGΔTM resulted in the significant enhancement of SIINFEKL-specific central memory T cell precursors ($CD8^+$ $SIINFEKL^+$ $CD27^+$ $CD62L^+$ $KLRG1^-$) and effector memory T cell precursors ($CD8^+$ $SIINFEKL^+$ $CD27^+$ $CD62L^-$ $KLRG1^-$).

cGAMP-STINGΔTM Enhances the Antitumor Therapeutic Efficacy

Figure 22:
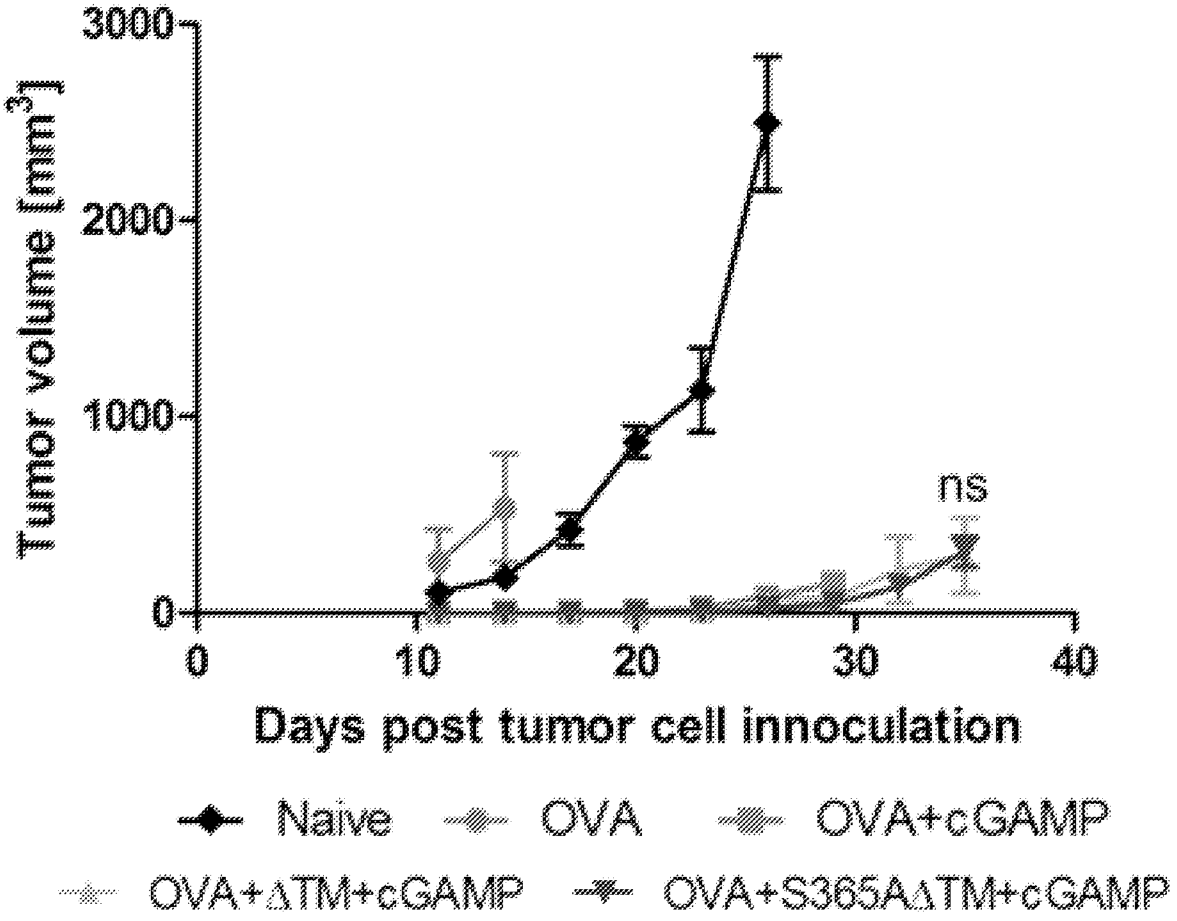
FIG. 22 shows a plot demonstrating overall tumor growth curve. Groups of C57BL/6 (n=7) mice were immunized with 50 μg of OVA alone or OVA mixed with 1 μg of cGAMP or 40 μg of STINGΔTM (or 40 μg of S365ASTINGΔTM) on days 0 and 7. On day 21, mice were challenged with 1 million B16-OVA cells subcutaneously.
Figure 23:
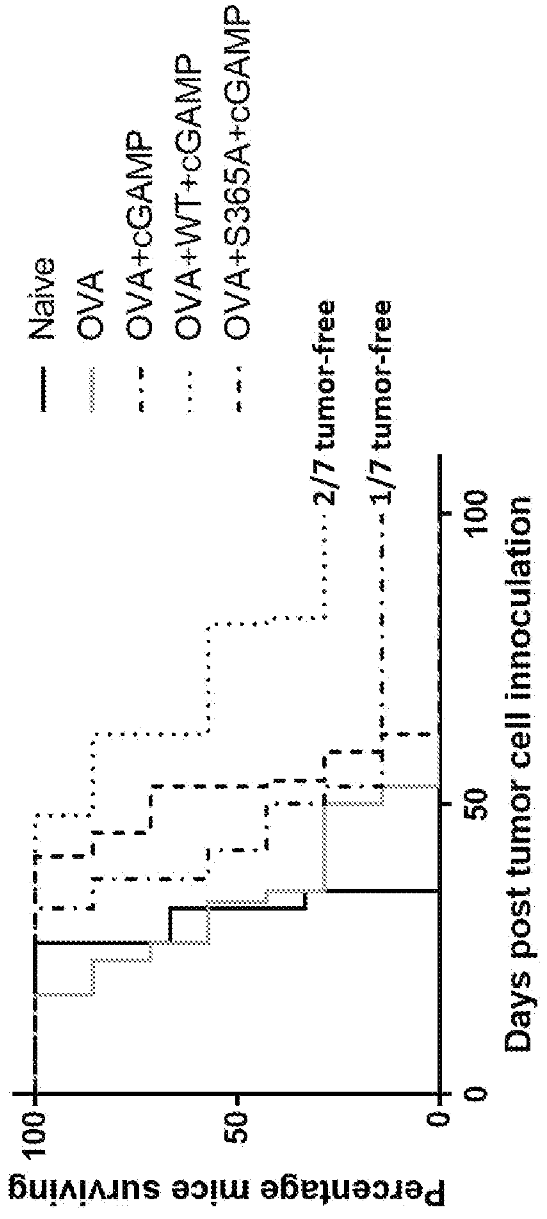
FIG. 23 shows a plot demonstrating survival curve of mice under the protocol as described for FIG. 22.
Figure 24:
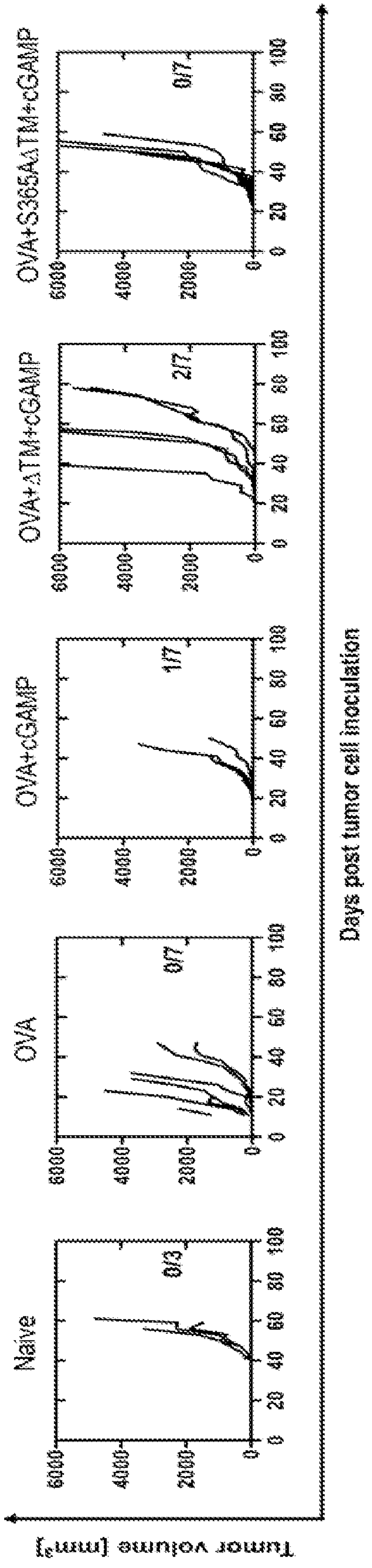
FIG. 24 shows a plot demonstrating individual tumor growth curve under the protocol as described for FIG. 22, with numbers of surviving mice at the end of study (day 100) denoted.

To explore the potential of cGAMP-STINGΔTM tetramer as a new mode of STING agonist-based cancer immunotherapy, the antitumor efficacy of cGAMP-STINGΔTM tetramers with a prophylactic study, using a melanoma cell line modified to express SIINFEKL peptide (B16-OVA) as an antigen epitope for vaccination was first evaluated. Groups of animals from the tetramer and intracellular cytokine staining study were challenged with 1 million B16-OVA cells at day 21 via subcutaneous injection. Tumor sizes were measured every 3 days to monitor the cancer progression and was recorded prior to the death of any mouse within a group. As such, anti-tumor therapeutic efficacy was evaluated from both tumor volume (FIG. 22) and mouse survival (FIGS. 23 and 24). Groups vaccinated with cGAMP+OVA, cGAMP+S365AΔTM+OVA, and cGAMP+ΔTM+OVA showed significantly enhanced protection against tumor challenge compared to the untreated and OVA only control groups (FIG. 22). Among these groups, cGAMP+ΔTM+OVA exhibited the slowest tumor progression and most prolonged survival, with 2 out of 7 mice achieving total protection and remaining tumor-free (FIGS. 23 and 24). The cGAMP+S365AΔTM+OVA group was also observed to result in improved survival when compared to cGAMP+OVA group. The vaccination efficacy is consistent with the IFN-γ and TNF-α expression level observed in the intracellular cytokine staining.

Figure 25:
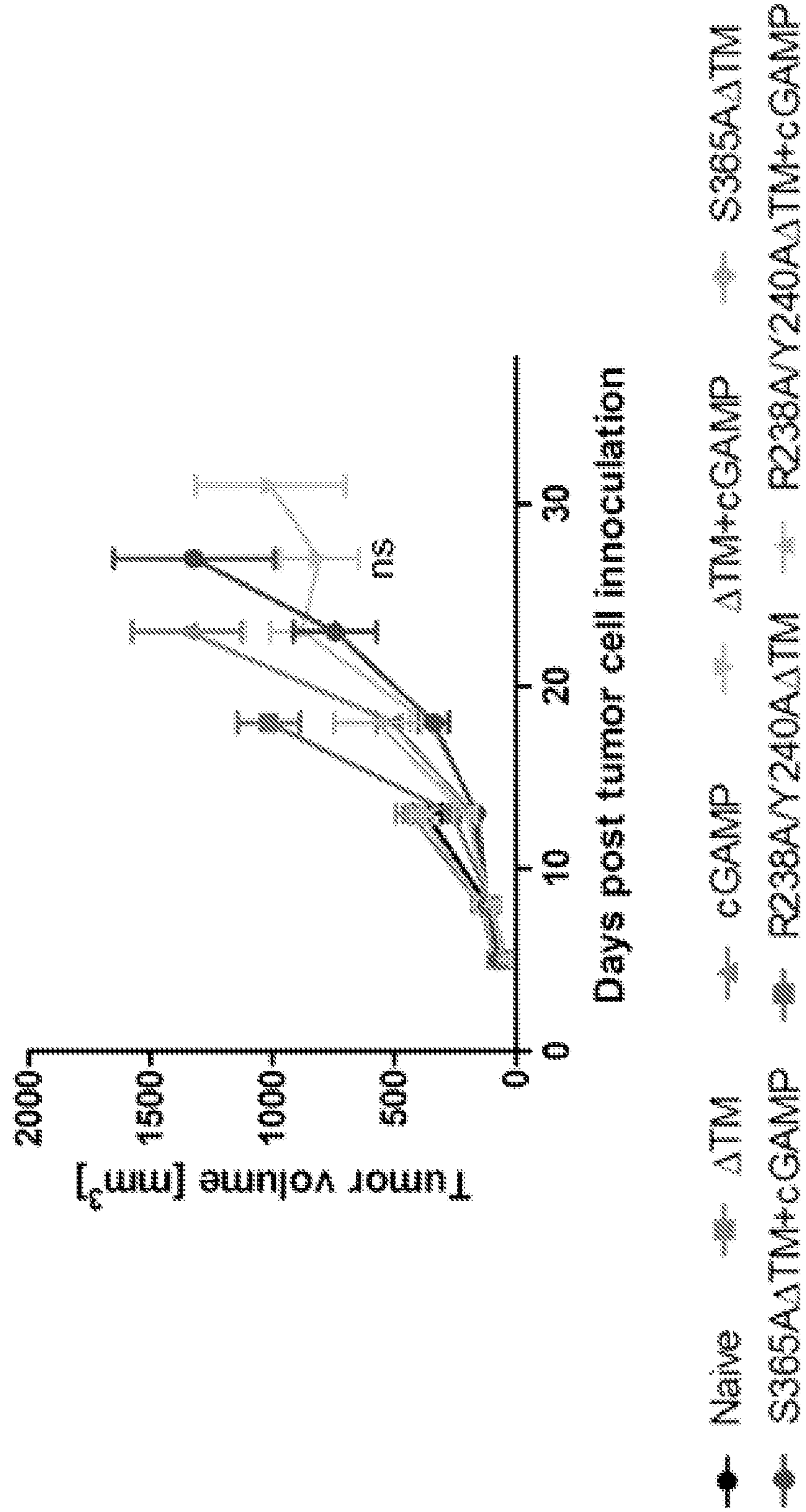
FIG. 25 shows a plot demonstrating overall tumor growth curve. Groups of C57BL/6 (n=7) mice were first inoculated with 1 million MC38 cells and then treated with 100 μg of STINGΔTM (or 100 μg of S365A, R237A/Y239A STINGΔTM) mixed with 2.5 μg of cGAMP starting on day 7 for five times, 7 days apart via intratumoral injection.
Figure 26:
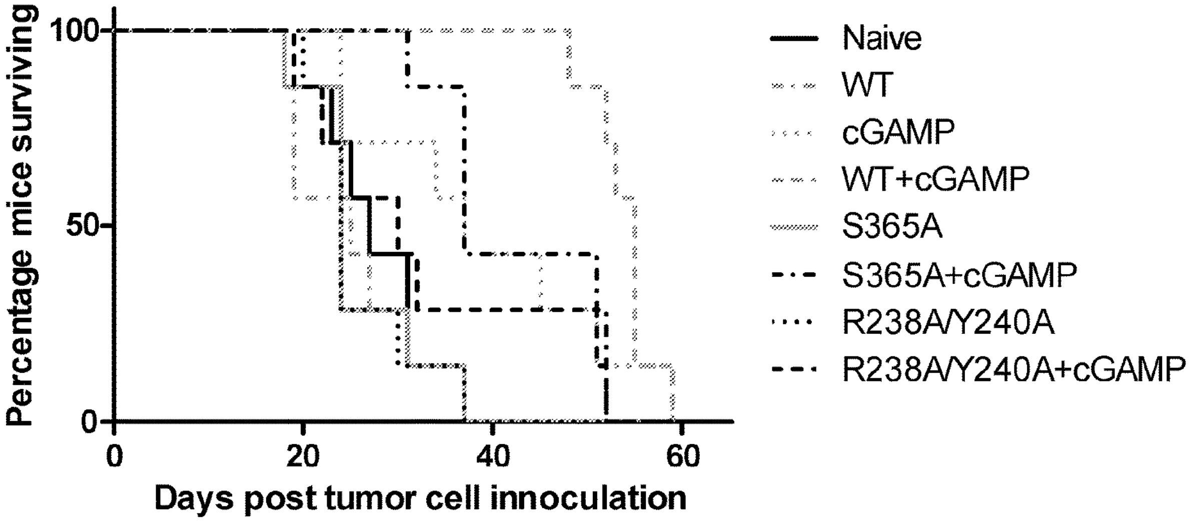
FIG. 26 shows a plot demonstrating survival curve of mice under the protocol as described for FIG. 25.
Figure 27:
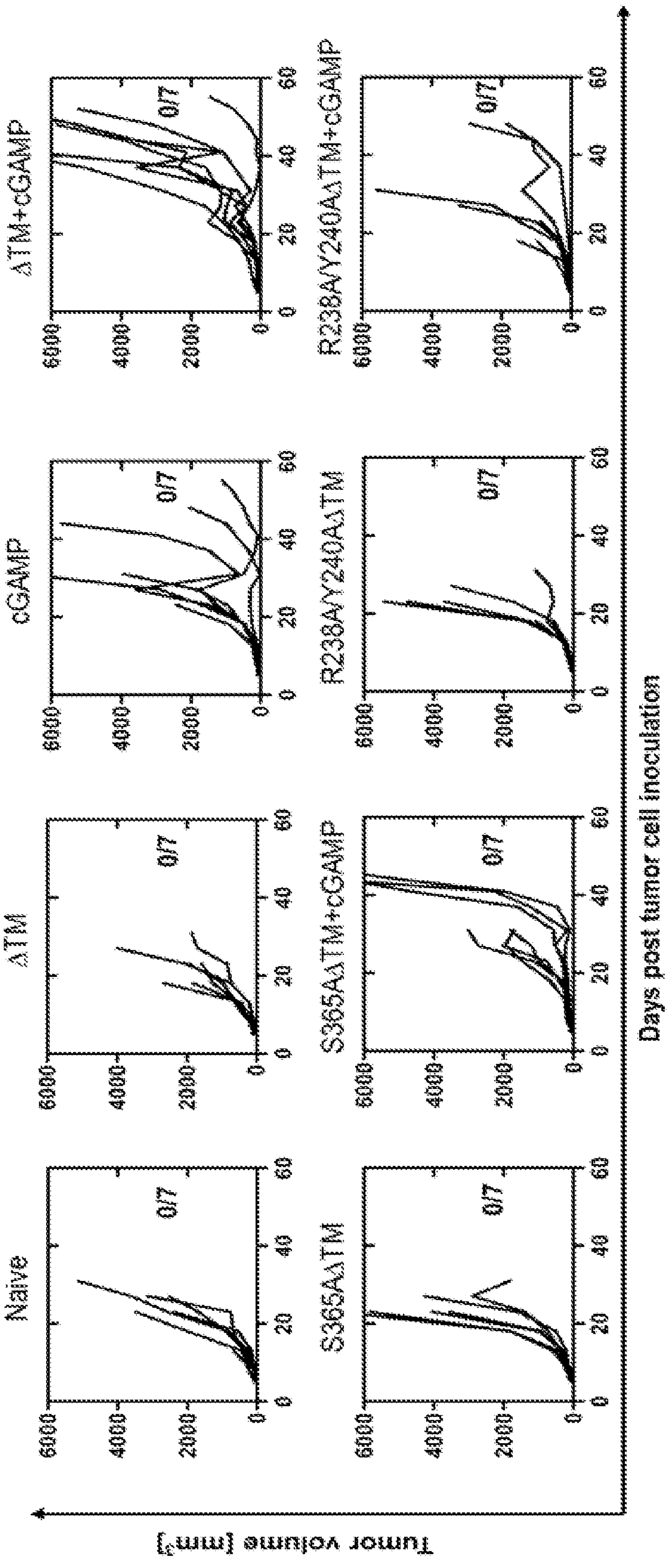
FIG. 27 shows a plot demonstrating individual tumor growth curve under the protocol as described for FIG. 25, with numbers of surviving mice at the end of study (day 60) denoted.

A therapeutic treatment study with an MC38 colon cancer model was then performed. C57BL/6 mice were inoculated with 1 million MC38 cells subcutaneously on day 0. After the primary tumor was established (between 50-80 $mm^3$), 100 μg STINGΔTM (plus S365A, or R238A/Y240A) with or without 2.5 μg cGAMP were injected intratumorally on days 7, 14, 21, 28 and 35. The tumor size and survival were monitored on a schedule similar to that of the prophylactic study. Treatment with cGAMP, cGAMP+S365AΔTM, and cGAMP+ΔTM significantly reduced tumor burden, with the cGAMP+ΔTM group having the overall best therapeutic effect and most prolonged survival (FIGS. 25-27).

Numerous studies have suggested that the transmembrane domain of STING protein is essential for intracellular STING signaling. Indeed, a STING-deficient cell line overexpressing TM deficient STING will not undergo STING signaling upon free cGAMP delivery. However, an interesting and well-defined self-assembled tetrameric structure of the TM deficient STING protein with cGAMP under physiological conditions has been discovered, and found that when delivered to the cell, this ribonucleoprotein complex could effectively trigger the STING signaling pathway independent of the status of endogenous STING. While already confirmed through size exclusion chromatography, these tetramers could be further characterized via electrophoresis and ultracentrifugation in later studies. Ultimately, this approach as a bioinspired method for cGAMP therapeutics was developed to introduce a highly effective means of cGAMP delivery that potentially addresses the occurrence of defective STING in humans either due to cancer epigenetics or genetic heterogeneity. In the interest of translational relevance, the therapeutic efficacy of the platform was tested in vivo and it was determined that the cGAMP-STINGΔTM tetramers can promote robust humoral response and antigen-specific T cell activation and elicit superior anti-tumoral immunity against a melanoma and a colon cancer model. In light of the role of activating STING signaling towards overcoming resistance against immune checkpoint blockade, future work can explore the delivery of cGAMP-STINGΔTM tetramers in combination with anti-PD(L)1 and anti-CTLA4. Alternatively, genetic fusion of STINGΔTM tetramers with tumor specific antigen peptides may enable simultaneous delivery of STING agonist-based adjuvant and antigens into dendritic cells to maximize the immune response. In summary, this work may open a new paradigm towards engineering immune adaptors to address vaccinology and immunotherapy.

In some embodiments, the therapeutic cancer vaccine includes a neoantigen that is identified by a genetic sequencing of the RNA (or DNA) contained in a hematologic tumor or a solid tumor-tissue sample obtained by needle biopsy, surgical excision, or other suitable method from one or more tumor sites of a patient. The genetic sequencing of a patient's tumor sample may be performed by techniques readily known to one skilled in the art or by using standard procedures, as described, for example, in U.S. Patent Publication No. 2011/0293637, Composition and Methods of Identifying Tumor Specific Neoantigens, incorporated herein by reference in its entirety for all purposes. After the genetic sequencing is completed, the identified peptide sequences surrounding the cancer mutation are evaluated for their potential binding affinity to the patient's Class I and Class II Major Histocompatibility Complex (MHC) proteins. By using techniques readily known to one skilled in the art, the neoantigen peptides with the highest binding affinity for the patient's MHC proteins are selected for use in the vaccine. In certain aspects, one or more of the identified neoantigen peptides are engineered by using automated synthetic techniques, readily known to those skilled in the art.

MHC proteins on the surface of antigen-presenting cells (APC) bind and present peptide antigens to the helper and effector T cells of the immune system, thus directing an immune response to the tumor. MHC Class I proteins typically present peptides of 8-11 amino acids in length while MHC Class II proteins present peptides of 20-25 amino acids. Such neoantigen peptides can be utilized as the tumor antigen component of a cancer vaccine.

In come embodiments, the method of cancer treatment by inducing humoral and cellular immune responses against cancer cells in a patient may include administering the vaccine to the patient at a prescribed dose by intravenous, intradermal, subcutaneous, intramuscular, intranodal, or intra-tumoral injection, or any combination thereof. According to another aspect, the patient can receive multiple vaccine injections at separate sites or the patient may receive multiple vaccine injections at the same site. According to yet another aspect, the patient receives multiple vaccinations at prescribed time intervals. According to other aspects, the time intervals may include time intervals such as every 1, 2, 3, or 4 weeks or every 2 to 4 weeks.

II. Peptide-Fused-STINGΔTM-CDN Complexes.

Peptide-based vaccines are an attractive class of vaccines due to their efficient synthesis process and easy quality control. With the advent of bioinformatic tools in efficiently predicting neo-antigens, peptide vaccines have gained tremendous attention in cancer immunotherapy. However, the delivery of peptide vaccines has remained a major challenge, primarily due to ineffective transport to lymph nodes and low immunogenicity. Described herein is a strategy for peptide vaccine delivery by first fusing the peptide to the cytosolic domain of the stimulator of interferon genes protein (STINGΔTM), then mixing the peptide-STINGΔTM protein with STING agonist cGAMP. The process results in the formation of self-assembled cGAMP-peptide-STINGΔTM tetramers, which enables efficient lymph node trafficking of the peptide. Moreover, the cGAMP/STINGΔTM complex acts not only as a protein carrier for the peptide, but also as a potent adjuvant capable of triggering STING signaling independent of endogenous STING protein—an especially important attribute considering that certain cancer cells epigenetically silence their endogenous STING expression. It has been demonstrated with model antigen SIINFEKL that the platform elicits effective STING signaling in vitro, draining lymph node targeting in vivo, effective T cell priming in vivo as well as anti-tumoral immune response in a mouse melanoma model, providing a versatile solution to the challenges faced in peptide vaccine delivery.

In the past decade, the field of oncology has been revolutionized by cancer immunotherapy, which utilizes the antigen-directed cytotoxicity of T cells to eliminate tumor cells. Neoantigens, cancer-specific peptides that are absent from the human genome, have thus emerged as promising antigenic targets for T cells to generate anti-tumor responses. Various techniques have enabled the efficient identification and optimization of neoantigens, which can then be easily synthesized and characterized before they are administered to the patient as personalized cancer vaccines. However, despite advances in neoantigen research, the potency of peptide antigens are in general lacking due to insufficient trafficking to the draining lymph nodes and poor immunogenicity from ineffective activation of antigen presenting cells (APCs). These challenges have motivated studies on the development of immune-stimulatory adjuvants and carriers, including the fusion of peptide epitopes to transport proteins or antibodies for enhanced targeting and accumulation in draining lymph nodes, as well as the co-delivery of peptides with adjuvants in synthetic cargos such as polymersomes, liposomes, gold nanoparticles, and hydrogels.

Among these adjuvants, those that interact with the STING pathway have gained increasing attention as a therapeutic target in cancer immunotherapy, due in large to STING's potent activation of antigen presenting cells (APCs) and anti-tumoral T cell responses. Consequently, STING agonists such as 2'3' cyclic guanosine monophosphate (GMP)—adenosine monophosphate (AMP) (cGAMP) have been included in various cancer vaccines to enhance the efficacy of checkpoint blockade. As described above, STING can be used as a biologic and carrier, where the cytosolic domain of STING protein (STINGΔTM) is repurposed as a fully functional platform for cGAMP delivery. It was determined that STINGΔTM self-assembles with cGAMP at physiological conditions to form a well-defined tetrameric complex that is capable of triggering STING signaling even in STING-deficient cell lines, and also observed an effective transport of the cGAMP-STINGΔTM complex to the draining lymph nodes after tail base injection in mice.

In light of the aforementioned challenges in peptide vaccine delivery, this bioinspired cGAMP-STINGΔTM signaling complex was leveraged to deliver a model antigen epitope from chicken ovalbumin amino acids 252-272: GLEQLESIINFEKLTEWTSS (denoted as SIINFEKL) by fusing the peptide to the N-terminus of STINGΔTM protein and then complexing the fusion protein with cGAMP, facilitating a co-localized delivery of antigen epitope, adjuvant cGAMP, and cGAMP's functional carrier STINGΔTM. This resulted in a similar self-assembled signaling complex of SIINFEKL-STINGΔTM with cGAMP that could activate type-I interferon in vitro, activate APCs ex vivo and in vivo, and traffic to the inguinal lymph nodes. It was also observed to elicit robust antigen-specific T-cell responses and an anti-tumoral response in a prophylactic B16 melanoma mouse model, demonstrating the potential of this platform in addressing the poor immunogenicity and ineffective lymph node trafficking of peptide vaccines.

Overview of the delivery strategy: as described above, pre-dimerized STINGΔTM to self-assembles in the presence of cGAMP a well-defined cGAMP-STINGΔTM tetramer, which results in lymphatic accumulation several times higher than the that of an equal amount of STINGΔTM protein injected (possibly due to the increase of size from STINGΔTM dimer to cGAMP-STINGΔTM tetramer). Inspired by the platform's performance in lymph node trafficking and its function as a highly potent adjuvant, a peptide vaccine delivery was sought by fusing the model antigen epitope peptide to the N-terminus of the STINGΔTM protein. Its C-terminus-fused counterpart was also synthesized as part of a pilot vaccination study in BL/6 mice, though fusion at the N-terminus resulted in a significantly higher level of TNF-$\alpha_+$/CD8$^+$ cells relative to an OVA+cGAMP control. As a result, all subsequent experiments were conducted with peptides fused at the N-terminus of STINGΔTM.

Figure 29:
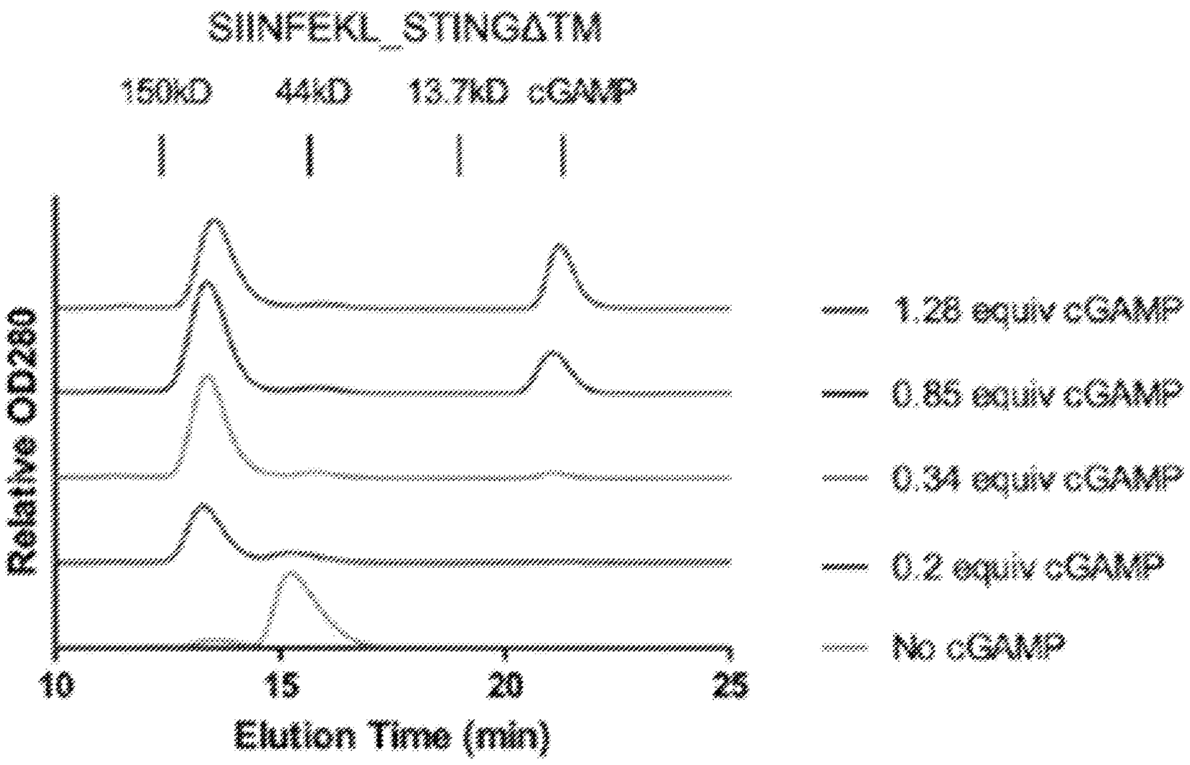
FIG. 29 shows FPLC analyses of mouse SIINFEKL_STINGΔTM in PBS, titrated with various molar equivalences of cGAMP.
Figure 30:
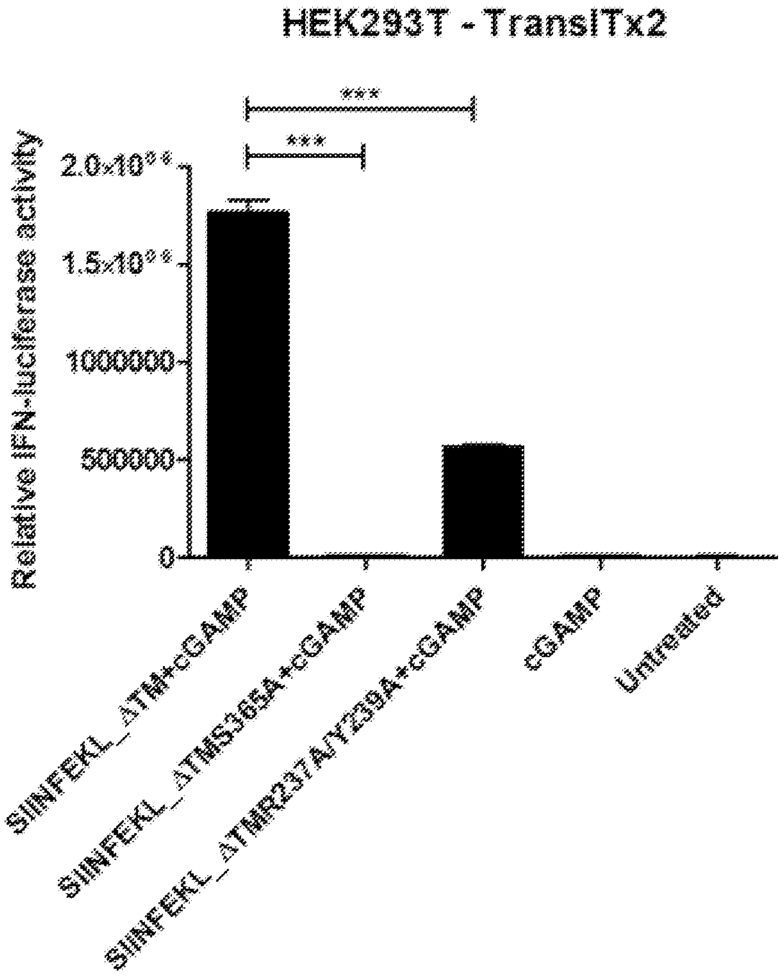
FIG. 30 shows a plot demonstrating that peptide-fused STINGΔTM/cGAMP complex effectively activates STING signaling in vitro. HEK293T cells (n=3) treated with SIINFEKL peptide-fused STINGΔTM/cGAMP complexes along with mutant controls, with the help of TransITx2. Interferon-luciferase activity was measured 24 hours post treatment. Values are reported as means±SEM.
Figure 31:
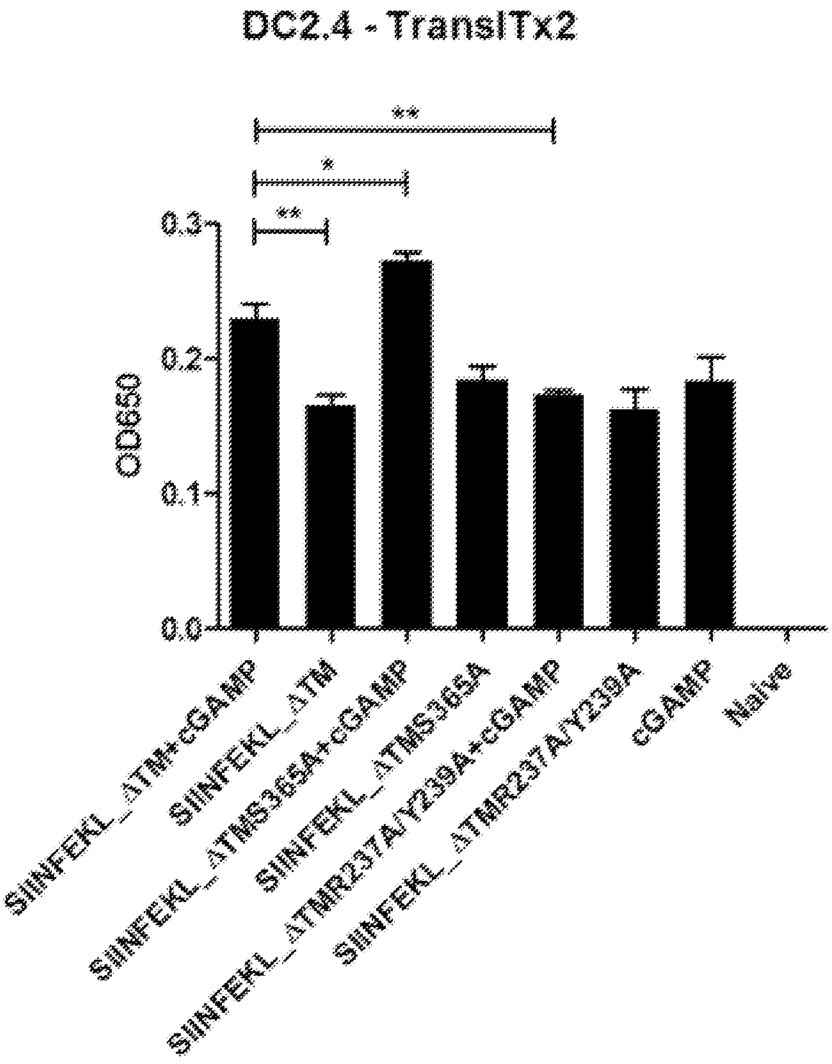
FIG. 31 shows a plot demonstrating that peptide-fused STINGΔTM/cGAMP complex effectively activates STING signaling in vitro. DC2.4 cells (n=3) treated with SIINFEKL peptide-fused STINGΔTM/cGAMP complexes along with mutant controls with the help of TransITx2. STING activation was determined by measuring secreted CXCL10 concentration in the culture media 48 hours post treatment. Values are reported as means±SEM.
Figure 32:
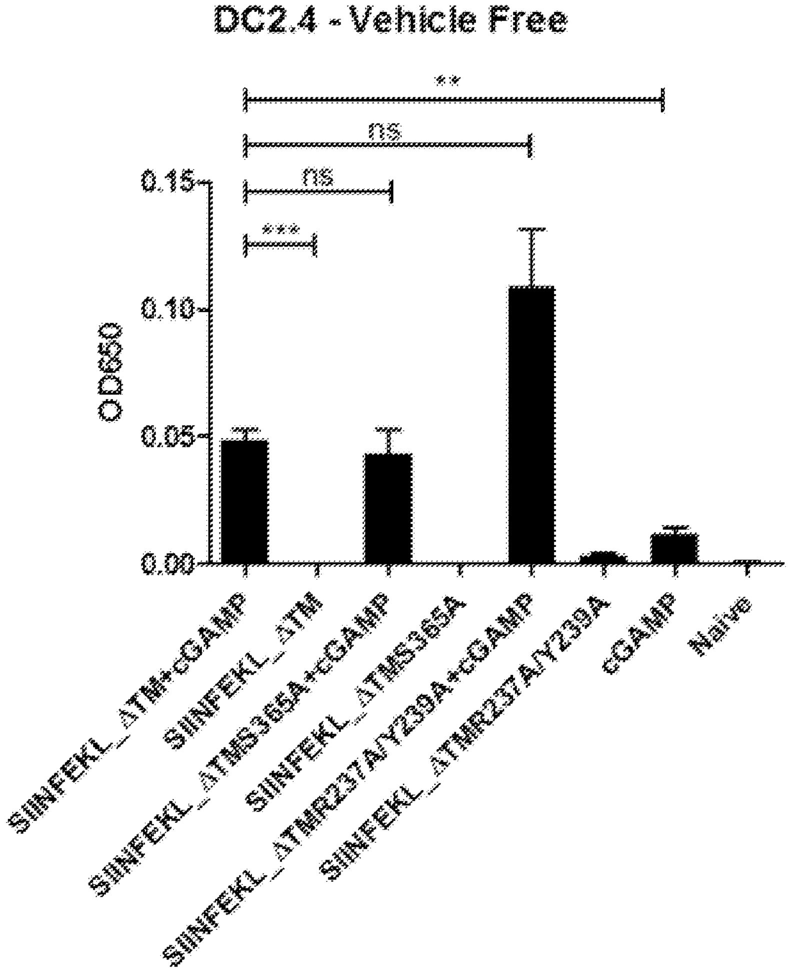
FIG. 32 shows a plot demonstrating that peptide-fused STINGΔTM/cGAMP complex effectively activates STING signaling in vitro. DC2.4 cells (n=3) treated with SIINFEKL peptide-fused STINGΔTM/cGAMP complexes along with mutant controls without TransITx2. STING activation was determined by measuring secreted CXCL10 concentration in the culture media 48 hours post treatment. Values are reported as means±SEM.
Figure 33:
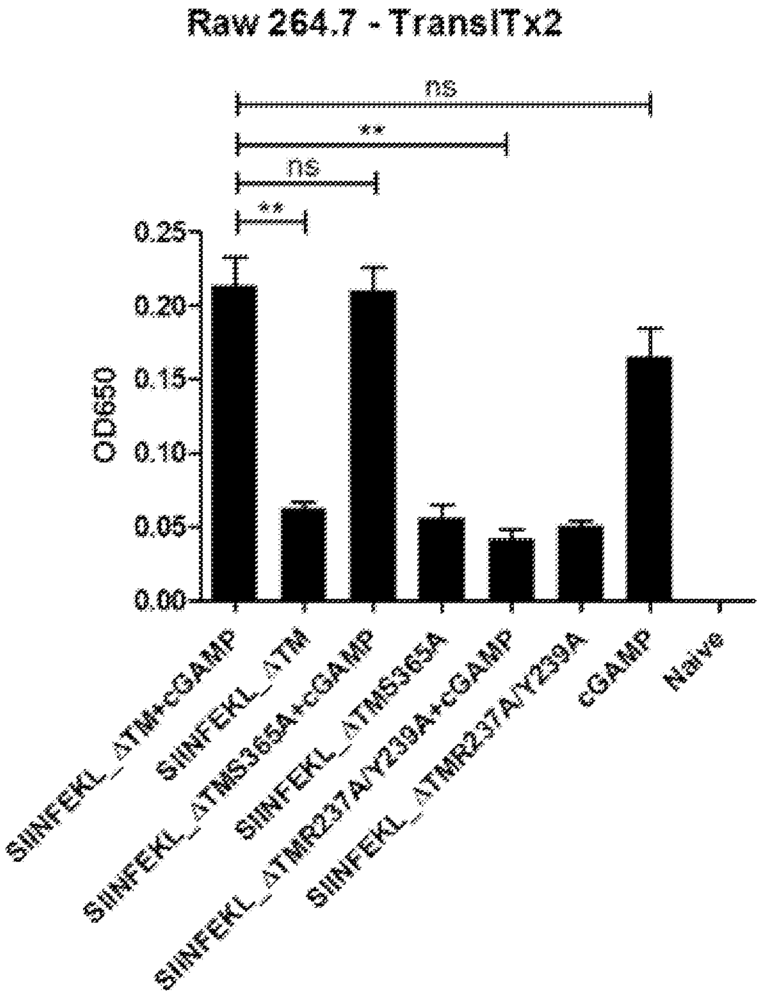
FIG. 33 shows a plot demonstrating that peptide-fused STINGΔTM/cGAMP complex effectively activates STING signaling in vitro. Raw264.7 cells (n=3) treated with SIINFEKL peptide-fused STINGΔTM/cGAMP complexes along with mutant controls with the help of TransITx2. STING activation was determined by measuring secreted CXCL10 concentration in the culture media 48 hours post treatment. Values are reported as means±SEM.
Figure 34:
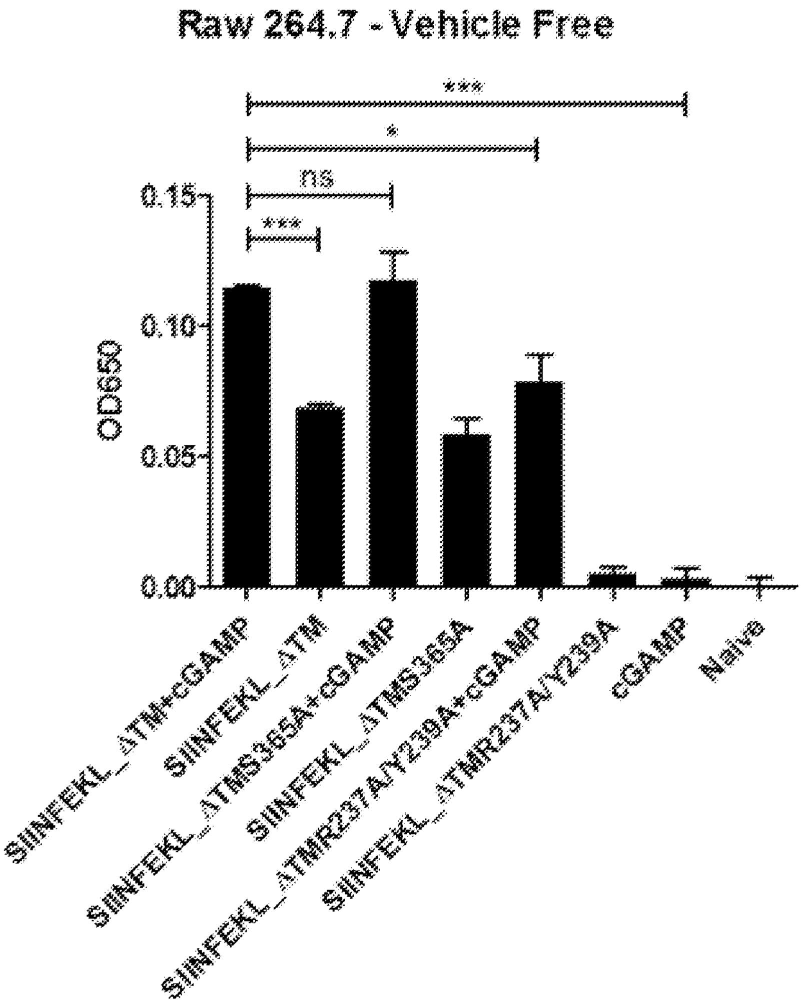
FIG. 34 shows a plot demonstrating that peptide-fused STINGΔTM/cGAMP complex effectively activates STING signaling in vitro. Raw264.7 cells (n=3) treated with SIINFEKL peptide-fused STINGΔTM/cGAMP complexes along with mutant controls without TransITx2. STING activation was determined by measuring secreted CXCL10 concentration in the culture media 48 hours post treatment. Values are reported as means±SEM.

In this study, the SIINFEKL peptide—the class I (Kb)-restricted peptide epitope of chicken ovalbumin (OVA) presented by class I MHC molecules—was used as the model antigen. To verify that the fusion of SIINFEKL to cytosolic STING will not alter its tetramerization- and in turn, its desirable size for lymph node accumulation-SIINFEKL-STINGΔTM protein was analyzed with fast protein liquid chromatography (FPLC) and stepwise titration with increasing molar ratios of cGAMP (FIG. 29).

This process resulted in the formation of a monodisperse, tetrameric cGAMP-SIINFEKL-STINGΔTM complex (~120 kD) from the SIINFEKL-STINGΔTM dimers (~60 kD), with excess cGAMP eluting off after all SIINFEKL-STINGΔTM had been saturated. In contrast, the R237A/Y239A mutant of SIINFEKL-STINGΔTM, which is unable to bind cGAMP, results in no peak shift upon cGAMP titration. These results corroborate the conclusion that the tetramerization of SIINFEKL-STINGΔTM is induced through cGAMP's specific interaction with STINGΔTM.

cGAMP-SIINFEKL-STINGΔTM activates STING signaling in vitro: studies of the functionality of the complex as a peptide vaccine adjuvant that triggers STING signaling. Both cell lines with and without endogenous STING were used to evaluate interferon activity resulting from this treatment, in order to account for potential epigenetic silencing of STING in certain cancer cells and the possibility of deficient downstream signaling from the HAQ mutation, which exists in 19% of the human population.

Significantly stronger interferon activity was observed upon the delivery of cGAMP-SIINFEKL-STINGΔTM to HEK293T cells via commercial transfection reagent TransITx2. This is in contrast to the cGAMP-only treatment group, which exhibits no STING signaling due to lack of endogenous STING protein. Treatment with functional mutants R237A\Y239A and S365A—which are unable to bind cGAMP and undergo TBK1 phosphorylation, respectively—likewise resulted in ineffective STING signaling. Ultimately, these mutant controls demonstrate the use of SIINFEKL-STINGΔTM as a functional adaptor protein instead of an inert vehicle, underscoring its key ability to circumvent diminished STING signaling.

Delivery of the treatment groups to the two cell lines with endogenous STING—DC2.4 and RAW264.7—resulted in STING activity for cGAMP-only, cGAMP-SIINFEKL-STINGΔTM, and cGAMP-SIINFEKL-STINGΔTM mutants (FIGS. 30-34). This was evaluated via measuring the concentration of mouse CXCL10, a chemokine secreted further downstream of STING signaling. Active uptake (vehicle free) of the cGAMP-SIINFEKL-STINGΔTM complex and its mutants was observed in both cell lines, though cGAMP-only treatments could only be successfully delivered with the aid of a transfection reagent. Once introduced to the cells via commercial transfection reagent, the cGAMP-only control resulted in similar levels of activity to cGAMP-SIINFEKL-STINGΔTM and its mutants, with only the R237A/Y239A mutant resulting in significantly lower interferon activity in the RAW264.7 cell line. This suggests that SIINFEKL-STINGΔTM may function primarily or partially as a carrier in the presence of endogenous STING, as opposed to playing a critical role in triggering STING signaling under STING-depleted conditions.

Figure 35:
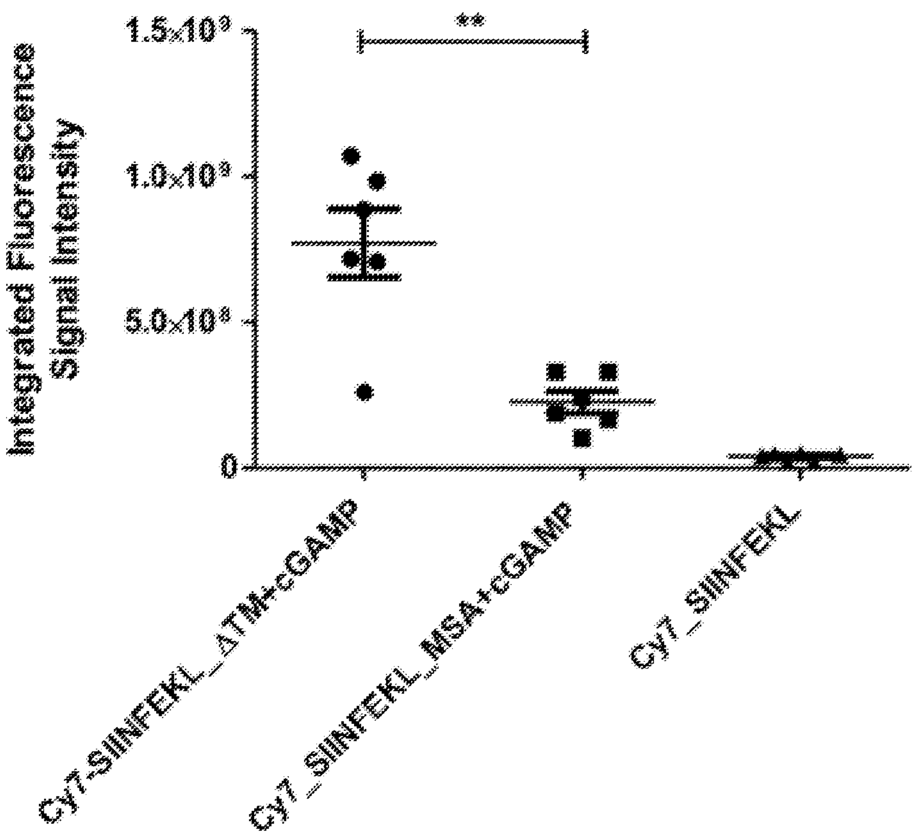
FIG. 35 shows a plot demonstrating integrated fluorescent intensity of Cy7 labeled protein/peptide in inguinal lymph nodes. Groups of Balb/c mice (n=3) that were tail-base injected with cGAMP-Cy7-SIINFEKL-STINGΔTM complex, cGAMP plus Cy7-SIINFEKL_MSA, or Cy7-SIINFEKL at same equivalences of SIINFEKL peptide. Inguinal lymph nodes were harvested at 24 hours post injection for the imaging.

Draining lymph node trafficking and T cell priming: as noted above introduction, the low lymphatic trafficking of peptides presents an obstacle in the development of peptide vaccine candidates. Researchers in the field have demonstrated that fusion of the epitope peptide to a transport protein, such as mouse serum albumin (MSA), may ameliorate this problem. The efficacy of the cGAMP-SIINFEKL-STINGΔTM platform in targeting the lymphatic system against that of SIINFEKL-MSA+cGAMP and SIINFEKL-only was evaluated, and it was determined that SIINFEKL-STINGΔTM exhibited significantly higher accumulation in the draining lymph node 24 hours post tail base injection (FIG. 35)

Figure 36:
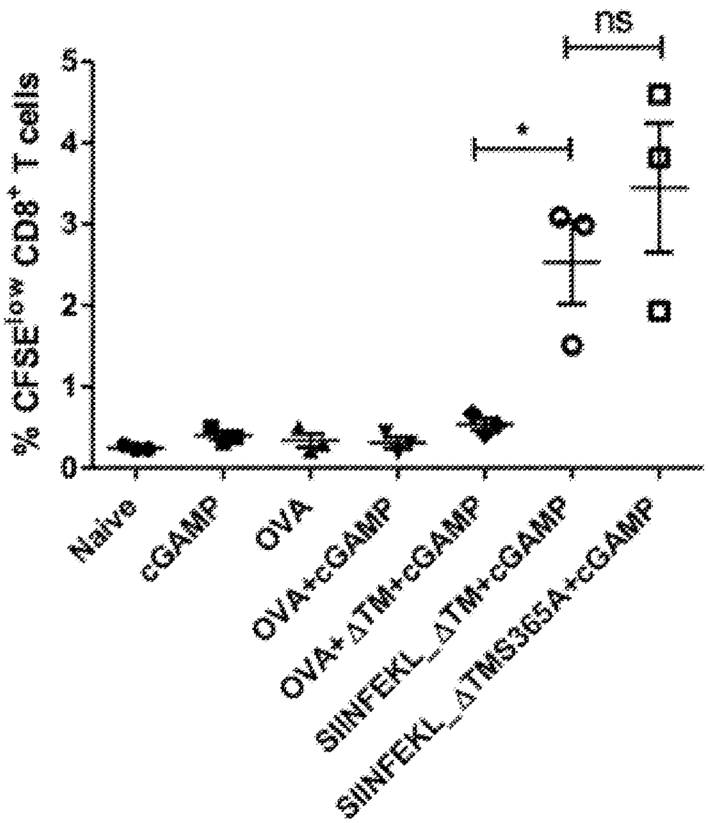
FIG. 36 shows a plot demonstrating antigen specific T cells that were gated as CFSE low CD8+ cells. DC2.4 cells were first treated with cGAMP/SIINFEKL-STINGΔTM along with controls, and co-cultured with CFSE stained OT1 lymphocytes the following day. Cells were collected 3 days after co-culture for flow cytometry analysis.

Following that, an ex vivo antigen presentation assay with DC2.4 cells was performed in order to evaluate peptide-specific immune responses. DC2.4 cells were first treated for 24 hours with either cGAMP-SIINFEKL-STINGΔTM complexes or controls such as OVA full protein, OVA+cGAMP, and cGAMP-SIINFEKL-STINGΔTM S365A mutants containing an equivalent amount of the SIINFEKL peptide. These cells were then co-cultured for three days with CFSE-stained lymphocytes harvested from OT1 mice that had been engineered to produce SIINFEKL-specific CD8 T-cells, stained with CD8 antibody, and analyzed via flow cytometry for actively proliferating OT1 CD8 T-cells in response to SIINFEKL presentation (represented by the $CFSE^{low}/CD8^{+}$ population). Treatment with cGAMP-SIINFEKL-STINGΔTM or the cGAMP-SIINFEKL-STINGΔTM S365A mutant resulted in significantly stronger T cell responses in comparison to all other treatment groups (FIG. 36). This is in good agreement with the previous in vitro results, where no statistical difference between these two treatment groups were observed in DC2.4 cells with endogenous STING.

Figure 37:
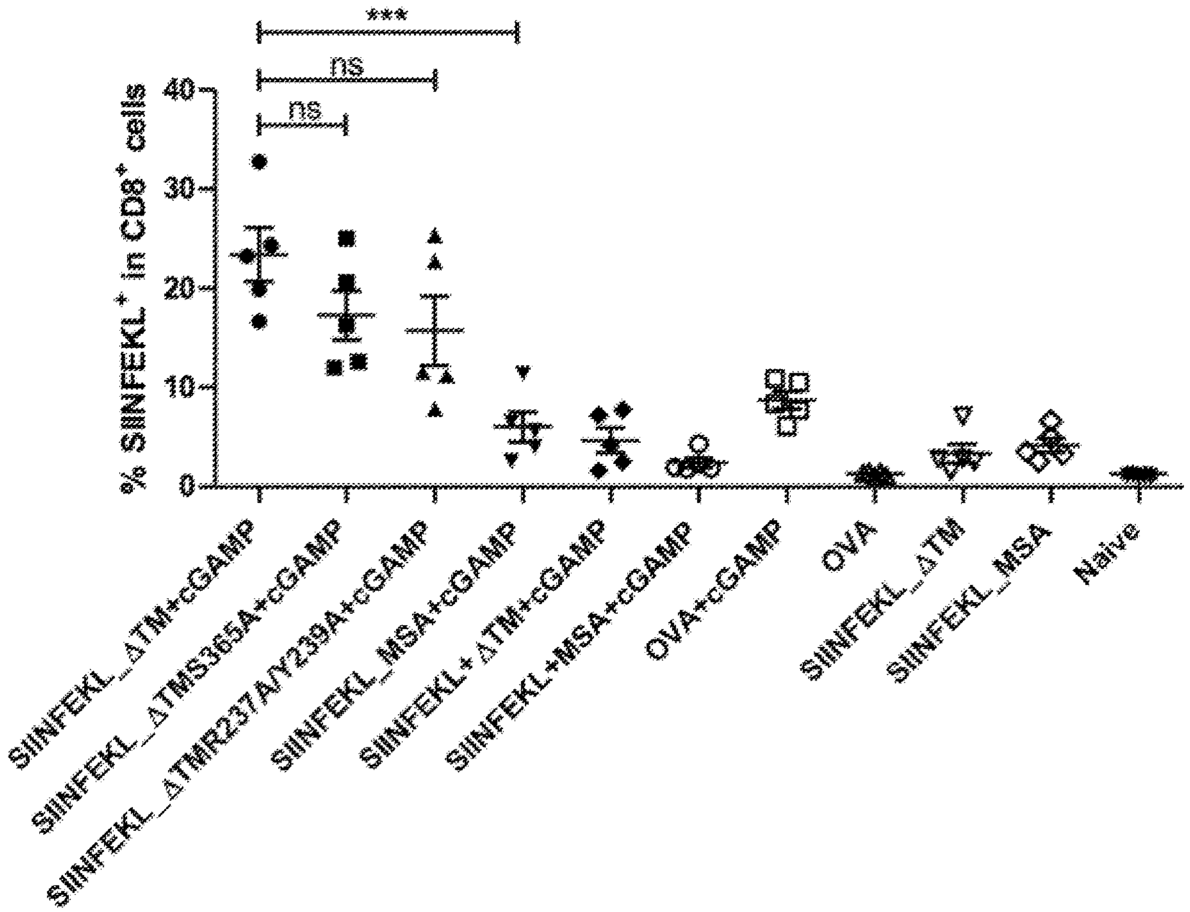
FIG. 37 shows a plot demonstrating the flow cytometry analysis for SIINFEKL-specific CD8 T cells. Groups of BL/6 mice were vaccinated with cGAMP/SIINFEKL-STINGΔTM along with controls at week 0 and 2. At week 3 mice blood were collected for CD8 antibody and SIINFEKL tetramer staining followed by flow cytometry analysis for SIINFEKL-specific CD8 T cells.

Finally, groups of BL/6 mice were vaccinated with cGAMP-SIINFEKL-STINGΔTM and a varied panel of controls, including but not limited to various SIINFEKL-STINGΔTM mutants, cGAMP+SIINFEKL peptide+STINGΔTM and cGAMP+SIINFEKL-MSA protein (FIG. 37). Blood was collected at Week 3 following the initial prime dose and a boost at Week 2, after which peripheral blood mononuclear cells (PBMCs) were stained with CD8 antibody and SIINFEKL-Tetramer. Treatment with cGAMP-SIINFEKL-STINGΔTM resulted in the strongest average antigen-specific T-cell response amongst all groups, with no statistical difference between the two mutants and $P<0.0001$ between all remaining groups. Notably, this comparison includes the SIINFEKL-MSA+cGAMP and SIINFEKL-MSA-only treatment groups, both of which have been reported to increase trafficking to the draining lymph nodes. The strategy produces a larger average antigen-specific T cell response than this current standard, highlighting the special advantage of the delivery platform in enhancing T cell priming through its active signaling function and carrier nature.

Figure 38:
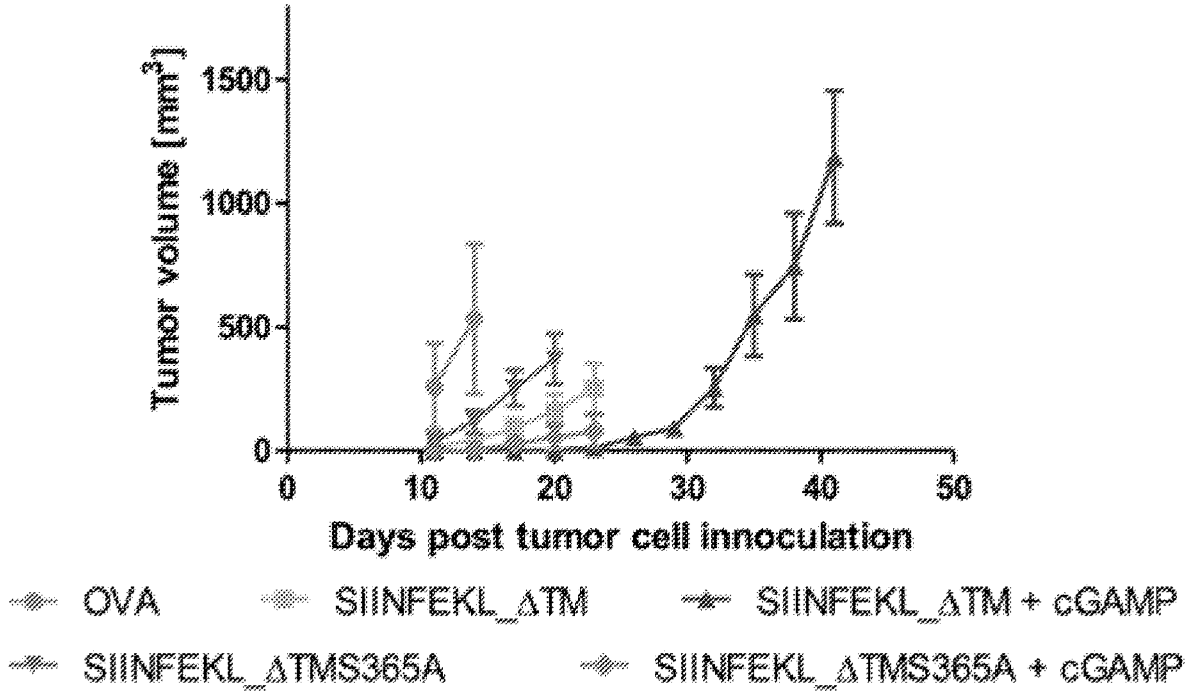
FIG. 38 shows a plot demonstrating total tumor volume progression. Groups of BL/6 mice were immunized with cGAMP-SIINFEKL-STINGΔTM along with other controls via tail base injection on day 0 and day 7. On day 21, mice were challenged with 1 million B16-OVA cells subcutaneously.
Figure 39:
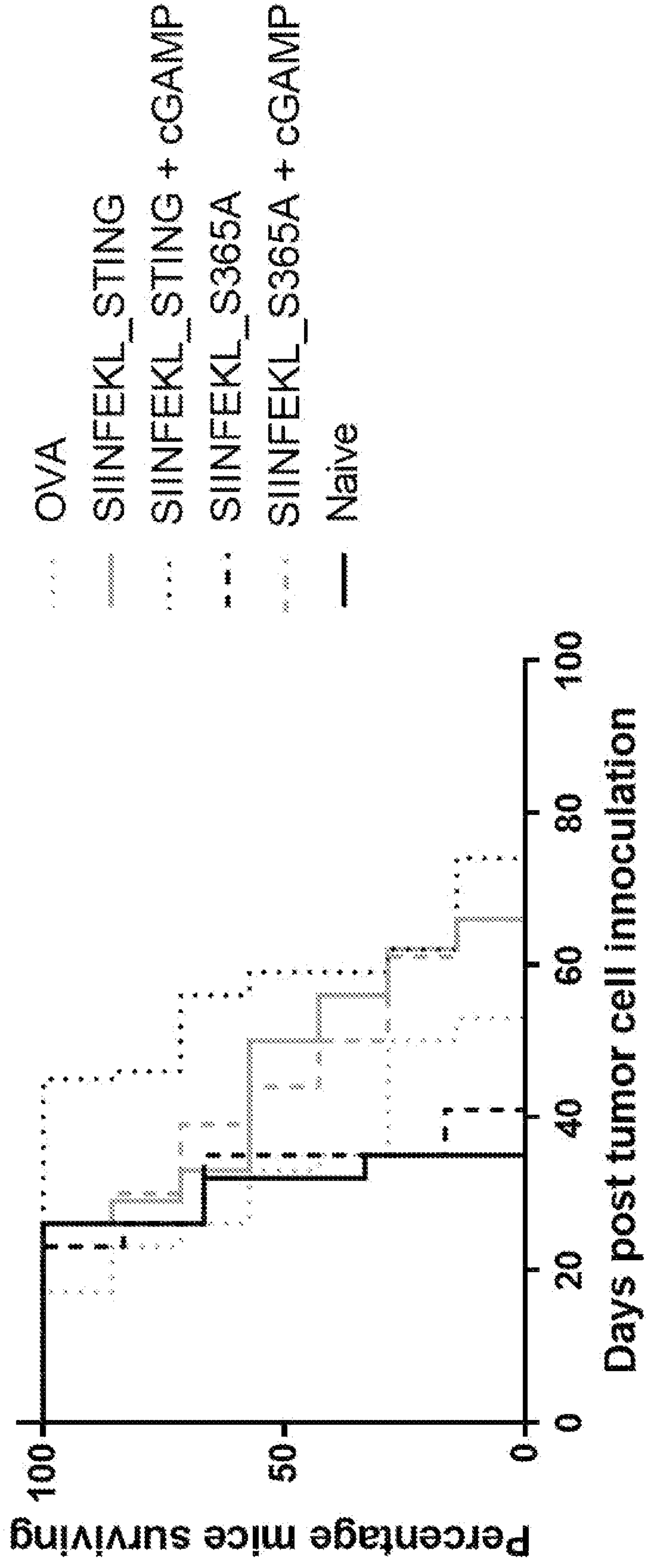
FIG. 39 shows plots demonstrating survival under the protocol described for FIG. 38.
Figure 40:
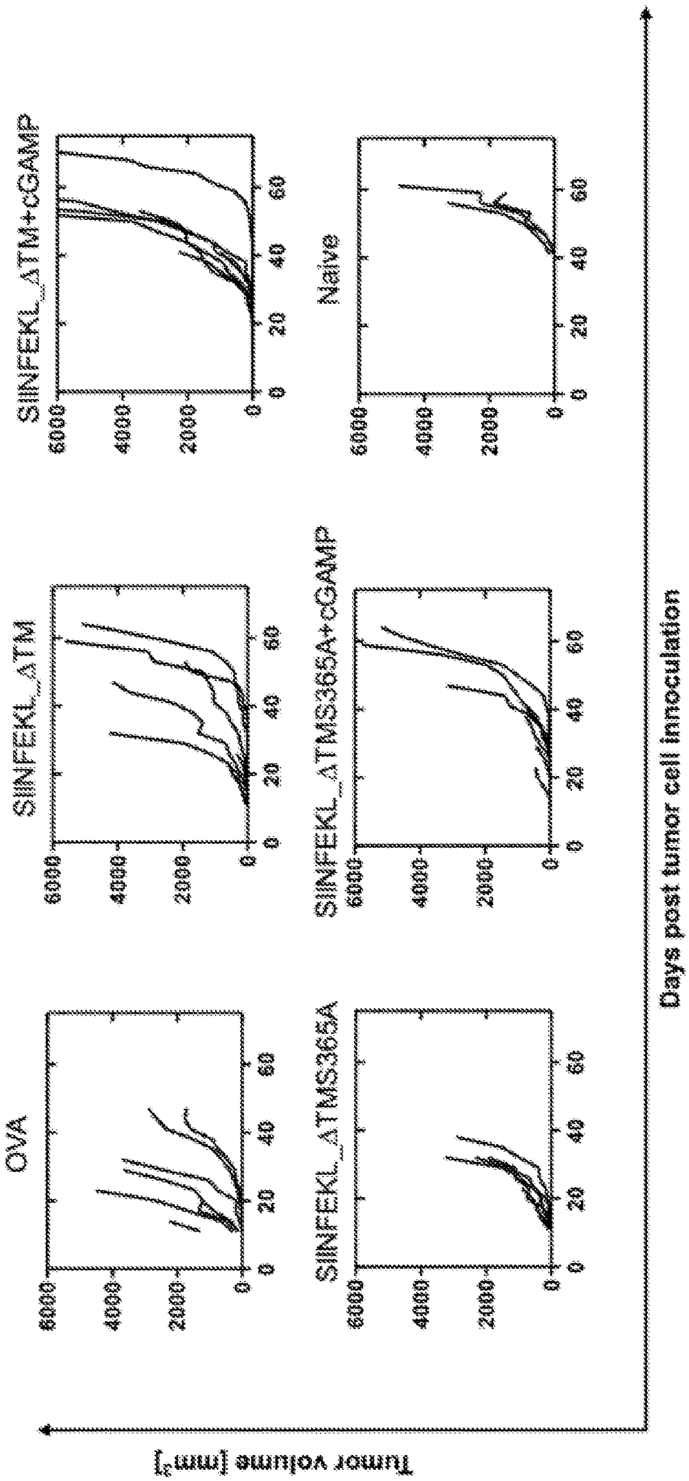
FIG. 40 shows plots demonstrating individual tumor volume progression under the protocol described for FIG. 38.
Figure 41:
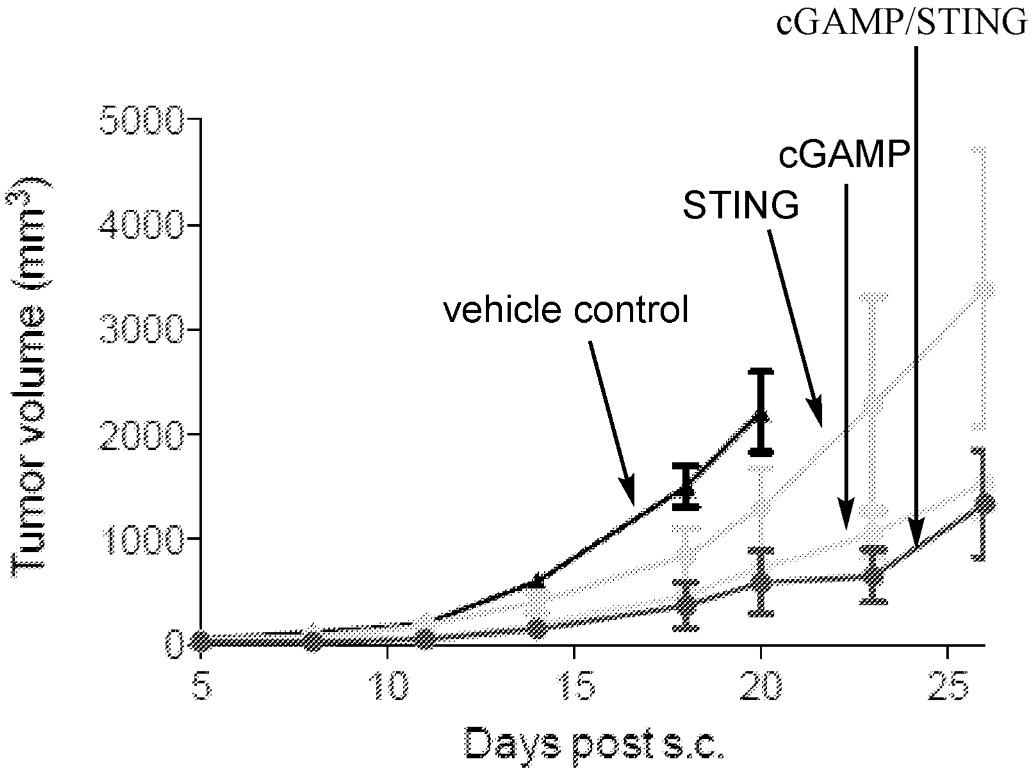
FIG. 41 shows a plot demonstrating tumor volume change in the group of mice treated with mSTINGΔTM, cGAMP, or cGAMP/.
Figure 42:
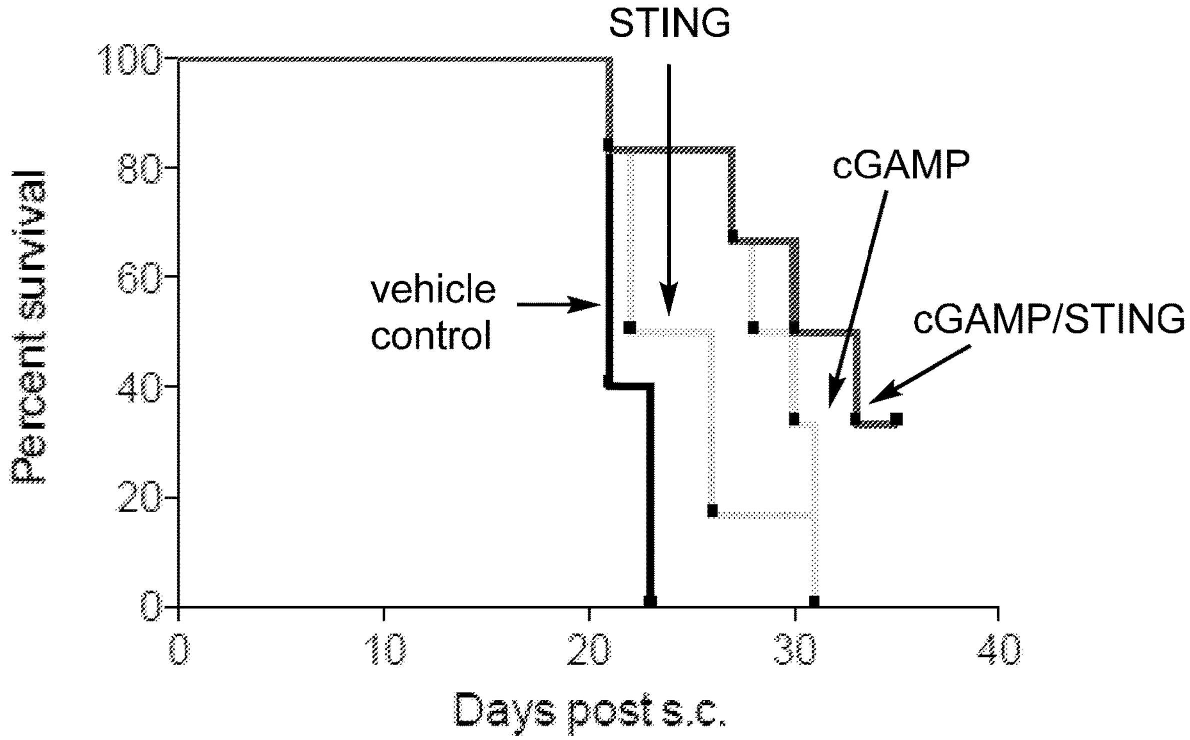
FIG. 42 shows a plot demonstrating survival in the group of mice treated with mSTINGΔTM, cGAMP, or cGAMP/mSTINGΔTM.
Figure 43:
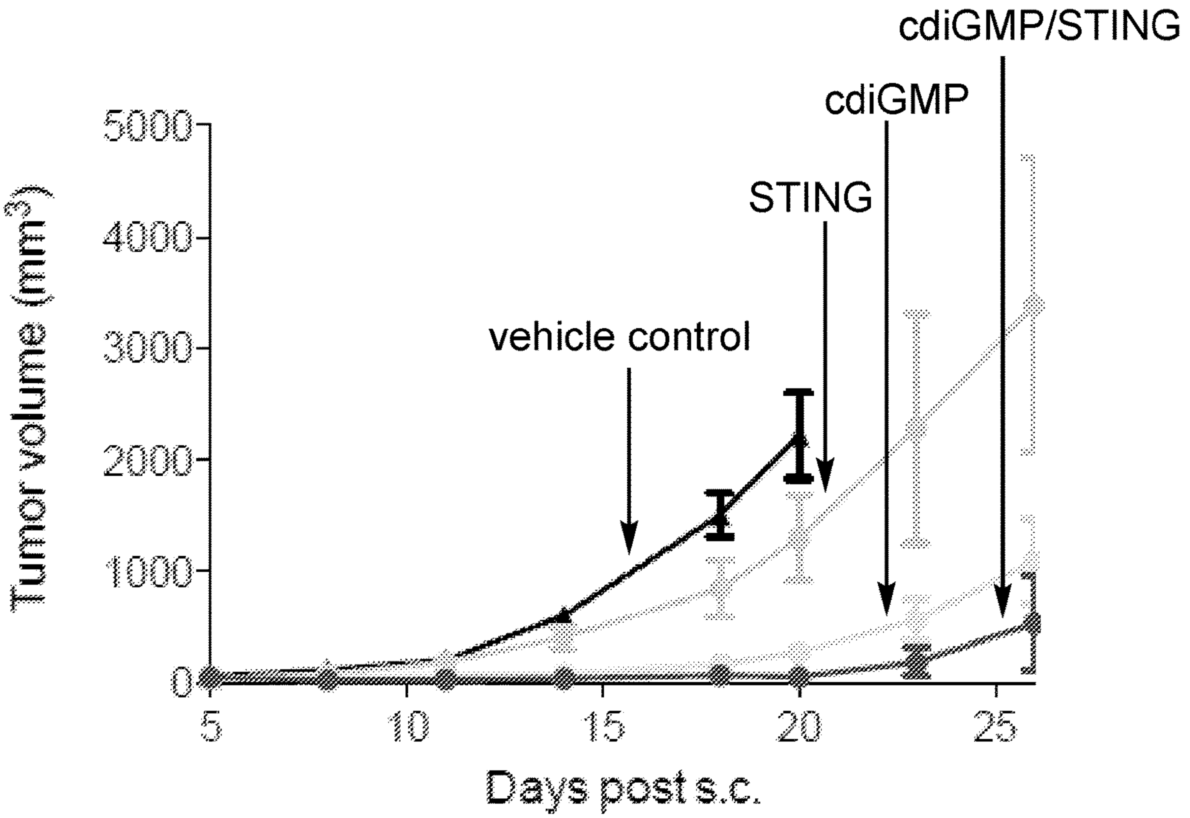
FIG. 43 shows a plot demonstrating tumor volume change in the group of mice treated with mSTINGΔTM, cdiGMP, or cdiGMP/mSTINGΔTM.
Figure 44:
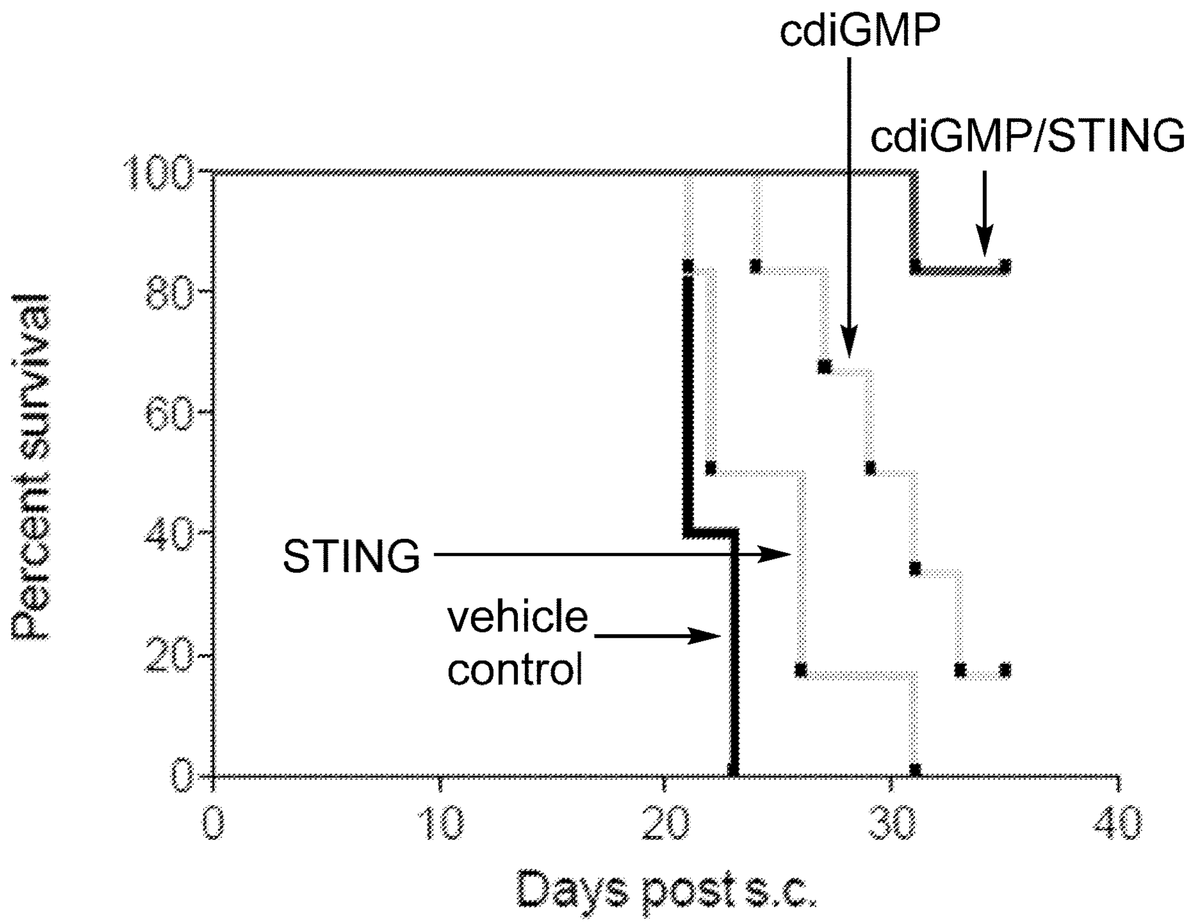
FIG. 44 shows a plot demonstrating survival in the group of mice treated with mSTINGΔTM, cGAMP, or cGAMP/mSTINGΔTM.

Anti-tumoral immunity: to evaluate the anti-tumoral efficacy of this peptide delivery system, groups of BL/6 mice were tail-base vaccinated with cGAMP-SIINFEKL-STINGΔTM alongside several controls. Mice were primed at Day 0, received a boost at Day 7, and challenged at Day 21 with a subcutaneous inoculation of 1 million B16-OVA melanoma cells expressing SIINFEKL peptide on their surface. Tumor growth and survival of these challenged mice were then monitored over time (FIGS. 38-40). Overall, the cGAMP-SIINFEKL-STINGΔTM vaccinated group resulted in the greatest inhibition of tumor growth and the most prolonged survival, affirming the potential of this platform as a tool for peptide vaccine delivery.

Despite their many benefits in cost and ease of synthesis, the effective delivery of peptide-based vaccines remains a challenge due to poor immunogenicity and inefficient lymphatic accumulation. Disclosed herein is a platform for a peptide-based cancer vaccine that simultaneously traffics the peptide to draining lymph nodes and activates the STING signaling pathway, circumventing the aforementioned issues through cGAMP-induced self-assembly and enhanced adjuvanticity. Fusion of the SIINFEKL epitope peptide to the N-terminus of STINGΔTM protein and subsequent complexation with cGAMP results in a well-defined tetrameric structure of desirable size for draining lymph node trafficking; inclusion of the STING protein activates STING signaling in vitro and boosts antigen presentation ex vivo. Moreover, cGAMP-SIINFEKL-STINGΔTM is shown to induce a robust T cell response, as well as potent anti-tumoral immunity. These results signal the promise in introducing peptide vaccines as part of a cGAMP-peptide-STINGΔTM complex, which provides an effective platform for the co-localized delivery of peptide with a strong adjuvant. Ultimately, this strategy may not only benefit the field of cancer immunotherapy, but also find applications in other fields, such as vaccine research against infectious diseases.

An effective therapeutic vaccine and related method of treatment by inducing humoral and cellular immune responses against malignant cells is described in this disclosure. The vaccine may comprise a complex that incorporates at least one peptide whose sequence encompasses a patient-specific genetic mutation associated with malignancy (neoantigen), a STINGΔTM peptide, and a STING protein agonist. The disclosed vaccine and related method provide a synergistic effect that induces a more effective immune response, uniquely tailored for an individual patient's tumor cells, directed against the patient's malignant cells.

As used herein, a "non-covalent complex" means a molecular entity formed by the assembly of component molecules into an aggregate. Examples of aggregates include, but are not limited to, aggregates (1) of oppositely charged free ions or ion pairs; (2) of molecules held together by electrostatic attraction; and (3) where one molecule or a plurality of molecules forms a cavity in which another molecule is located. There is no covalent bonding between the molecules, the attraction being generally due to van der Waals forces.

As used herein, the terms "peptide", "polypeptide", "protein" and variations of these terms refer to peptide, oligopeptide, oligomer or protein including fusion protein, respectively, comprising at least two amino acids joined to each other preferably by a normal peptide bond, or, alternatively, by a modified peptide bond, such as for example in the cases of isosteric peptides. A peptide, polypeptide or protein can be composed of L-amino acids and/or D-amino acids. Preferably, a peptide, polypeptide or protein is either (entirely) composed of L-amino acids or (entirely) of D-amino acids, thereby forming "retro-inverso peptide sequences". The term "retro-inverso (peptide) sequences" refers to an isomer of a linear peptide sequence in which the direction of the sequence is reversed and the chirality of each amino acid residue is inverted (see e.g. Jameson et al., Nature, 368, 744-746 (1994); Brady et al., Nature, 368, 692-693 (1994)). The terms "peptide", "polypeptide", "protein" can also include "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. In particular, a peptide, polypeptide or protein can comprise amino acids other than the 20 amino acids defined by the genetic code in addition to these amino acids, or it can be composed of amino acids other than the 20 amino acids defined by the genetic code. In particular, a peptide, polypeptide or protein in the context of the present invention can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, N.Y.; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" preferably include for example lipopeptides, lipoproteins, glycopeptides, glycoproteins and the like.

In some embodiments, peptide, polypeptide or protein as disclosed herein is a "classical" peptide, polypeptide or protein, whereby a "classical" peptide, polypeptide or protein is typically composed of amino acids selected from the 20 amino acids defined by the genetic code, linked to each other by a normal peptide bond.

As used herein, the term "protein A comprises protein B" means that the amino acid sequence of protein A comprises the amino acid sequence of protein B, and can further comprise additional unrecited amino acid sequences.

As used herein, the term "recombinant protein" refers to a protein that is not a naturally occurring protein. The term "recombinant protein" is not intended to restrict the means of producing or obtaining the protein. The recombinant protein of the invention may be produced by any known methods, including, but not limited to, genetic engineering methods and artificial synthesis methods.

The polypeptides provided herein may be functional fragments of the disclosed polypeptide. As used herein, a "fragment" or "functional fragment" is a portion of an amino acid sequence that is identical in sequence to but shorter in length than a reference sequence. A fragment may comprise up to the entire length of the reference sequence, minus at least one amino acid residue. For example, a fragment may comprise from 5 to 155 contiguous amino acid residues of a reference polypeptide, respectively. In some embodiments, a fragment may comprise at least 5, 10, 15, 20, 25, 30, 40, 50, 60, 70, 80, 90, 100, or 150 contiguous amino acid residues of a reference polypeptide. Fragments may be preferentially selected from certain regions of a molecule. The term "at least a fragment" encompasses the full-length polypeptide. A fragment of a polypeptide may comprise or consist essentially of a contiguous portion of an amino acid sequence of the polypeptide. A fragment may include an N-terminal truncation, a C-terminal truncation, or both truncations relative to the full-length polypeptide.

As used herein, the term "adjuvant" refers to a non-specific immunopotentiator, which can enhance immune response to an antigen or change the type of immune response in an organism when it is delivered together with the antigen to the organism or is delivered to the organism in advance.

As used herein, an "antigen" is any structural substance which serves as a target for the receptors of an adaptive immune response, in particular as a target for antibodies, T cell receptors, and/or B cell receptors.

An "epitope", also known as "antigenic determinant", is the part (or fragment) of an antigen that is recognized by the immune system, in particular by antibodies, T cell receptors, and/or B cell receptors. Thus, one antigen has at least one epitope, i.e. a single antigen, or has one or more epitopes. As used herein, the term "epitope peptide" refers to a peptide fragment on an antigen that can form an epitope or act as an epitope. Under some conditions, an epitope peptide alone can be specifically recognized/bound by an antibody against the epitope. Under some other conditions, an epitope peptide has to be fused to a polypeptide carrier to facilitate the epitope peptide to be specifically recognized by an antibody. The epitope comprised in an epitope peptide may be a linear epitope, or a conformational epitope. When an epitope peptide comprises a linear epitope, it may comprise or is a contiguous amino acid segment (i.e., a peptide fragment) forming the epitope in an antigen. When an epitope peptide comprises a conformational epitope, it may comprise or is a contiguous amino acid segment (i.e., a peptide fragment) covering all the amino acid residues involved in the conformational epitope. In some embodiments of the invention, an epitope peptide preferably has a length of no more than 500 amino acid residues, for example, a length of no more than 400 amino acid residues, a length of no more than 300 amino acid residues, a length of no more than 200 amino acid residues, a length of no more than 100 amino acid residues, a length of no more than 90 amino acid residues, a length of no more than 80 amino acid residues, a length of no more than 70 amino acid residues, a length of no more than 60 amino acid residues, a length of no more than 50 amino acid residues, a length of no more than 40 amino acid residues, a length of no more than 30 amino acid residues, or a length of no more than 25 amino acid residues.

As used herein, "cancer epitope" means an epitope from a cancer-associated antigen or from a cancer-specific antigen. Accordingly, "tumor epitope" means an epitope from a tumor-associated antigen or from a tumor-specific antigen. Such epitopes are typically specific (or associated) for a certain kind of cancer/tumor. In particular, cancer/tumor-associated (also cancer/tumor-related) antigens are antigens which are expressed by both cancer/tumor cells and normal cells. These antigens are normally present since birth (or even before). Accordingly, there is a chance that the immune system developed self-tolerance to those antigens. Cancer/tumor-specific antigens, in contrast, are antigens which are expressed specifically by cancer/tumor cells, but not by normal cells. Cancer/tumor-specific antigens include in particular neoantigens. In general neoantigens are antigens which were not present before appearance of cancer cells and are, thus, "new" to the immune system. In the context of cancer/tumors, cancer/tumor-specific neoantigens were typically not present before the cancer/tumor developed and cancer/tumor-specific neoantigens are usually encoded by somatic gene mutations in the cancerous cells/tumor cells. Since neoantigens are new to the immune system, the risk of self-tolerance of those antigens is considerably lower as compared to cancer/tumor-associated antigens.

Specific examples of cancer/tumor-associated, in particular tumor-related, or tissue-specific antigens useful in a complex for use as described herein include, but are not limited to, the following antigens: Her-2/neu, SPAS-1, TRP-2, tyrosinase, Melan A/Mart-1, gplOO, BAGE, GAGE, GM2 ganglioside, kinesin 2, TATA element modulatory factor 1, tumor protein D52, MAGE D, ING2, HIP-55, TGF-1 anti-apoptotic factor, HOM-Mel-40/SSX2, epithelial antigen (LEA 135), DF31MUC1 antigen (Apostolopoulos et al., 1996 Immunol. Cell. Biol. 74: 457-464; Pandey et al., 1995, Cancer Res. 55: 4000-4003), MAGE-1, HOM-Mel-40/SSX2, NY-ESO-1, EGFR, CEA, Epha2, Epha4, PCDGF, HAAH, Mesothelin; EPCAM; NY-ESO-1, glycoprotein MUC1 and NIUC10 mucins p5 (especially mutated versions), EGFR, cancer-associated serum antigen (CASA) and cancer antigen 125 (CA 125) (Kierkegaard et al., 1995, Gynecol. Oncol. 59: 251-254), the epithelial glycoprotein 40 (EGP40) (Kievit et al., 1997, Int. J. Cancer 71: 237-245), squamous cell carcinoma antigen (SCC) (Lozza et al., 1997 Anticancer Res. 17: 525-529), cathepsin E (Mota et al., 1997, Am. J Pathol. 150: 1223-1229), tyrosinase in melanoma (Fishman et al., 1997 Cancer 79: 1461-1464), cell nuclear antigen (PCNA) of cerebral cavernomas (Notelet et al., 1997 Surg. Neurol. 47: 364-370), a 35 kD tumor-associated autoantigen in papillary thyroid carcinoma (Lucas et al., 1996 Anticancer Res. 16: 2493-2496), CDC27 (including the mutated form of the protein), antigens triosephosphate isomerase, 707-AP, A60 mycobacterial antigen (Macs et al., 1996, J. Cancer Res. Clin. Oncol. 122: 296-300), Annexin II, AFP, ART-4, BAGE, β-catenin/m, BCL-2, bcr-abl, bcr-abl p190, bcr-abl p210, BRCA-1, BRCA-2, CA 19-9 (Tolliver and O'Brien, 1997, South Med. J. 90: 89-90; Tsuruta at al., 1997 Urol. Int. 58: 20-24), CAMEL, CAP-1, CASP-8, CDC27/m, CDK-4/m, CEA (Huang et al., Exper Rev. Vaccines (2002)1:49-63), CT9, CT10, Cyp-B, Dekcain, DAM-6 (MAGE-B2), DAM-10 (MAGE-B1), EphA2 (Zantek et al., Cell Growth Differ. (1999) 10:629-38; Carles-Kinch et al., Cancer Res. (2002) 62:2840-7), EphA4 (Cheng at al., 2002, Cytokine Growth Factor Rev. 13:75-85), tumor associated Thomsen-Friedenreich antigen (Dahlenborg et al., 1997, Int. J Cancer 70: 63-71), ELF2M, ETV6-AML1, G250, GAGE-1, GAGE-2, GAGE-3, GAGE-4, GAGE-5, GAGE-6, GAGE-7B, GAGE-8, GnT-V, gp100 (Zajac et al., 1997, Int. J Cancer 71: 491-496), HAGE, HER2/neu, HLA-A*0201-R1701, HPV-E7, HSP70-2M, HST-2, hTERT, hTRT, iCE, inhibitors of apoptosis (e.g., survivin), KH-1 adenocarcinoma antigen (Deshpande and Danishefsky, 1997, Nature 387: 164-166), KIAA0205, K-ras, LAGE, LAGE-1, LDLR/FUT, MAGE-1, MAGE-2, MAGE-3, MAGE-6, MAGE-A1, MAGE-A2, MAGE-A3, MAGE-A4, MAGE-A6, MAGE-A10, MAGE-A12, MAGE-B5, MAGE-B6, MAGE-C2, MAGE-C3, MAGE D, MART-1, MART-1/Melan-A (Kawakami and Rosenberg, 1997, Int. Rev. Immunol. 14: 173-192), MC1R, MDM-2, Myosin/m, MUC1, MUC2, MUM-1, MUM-2, MUM-3, neo-polyA polymerase, NA88-A, NY-ESO-1, NY-ESO-la (CAG-3), PAGE-4, PAP, Proteinase 3 (Molldrem et al., Blood (1996) 88:2450-7; Molldrem et al., Blood (1997) 90:2529-34), P15, p190, Pml/RARα, PRAME, PSA, PSM, PSMA, RAGE, RAS, RCAS1, RU1, RU2, SAGE, SART-1, SART-2, SART-3, SP17, SPAS-1, TEL/AML1, TPI/m, Tyrosinase, TARP, TRP-1 (gp75), TRP-2, TRP-2/INT2, WT-1, and alternatively translated NY-ESO-ORF2 and CAMEL proteins, derived from the NY-ESO-1 and LAGE-1 genes. Numerous other cancer antigens are well known in the art.

The term "sequence variant", as used herein, refers to any alteration in a reference sequence. The term "sequence variant" includes nucleotide sequence variants and amino acid sequence variants. Preferably, a reference sequence is any of the sequences listed in the section below "Sequences and SEQ ID Numbers" (Sequence listing), i.e. SEQ ID NO: 1 to SEQ ID NO: 23. Preferably, a sequence variant shares, in particular over the whole length of the sequence, at least 70%, at least 75%, preferably at least 80%, more preferably at least 85%, even more preferably at least 90%, particularly preferably at least 95%, most preferably at least 99% sequence identity with a reference sequence, whereby sequence identity is calculated as described below. In particular, a sequence variant preserves the specific function of the reference sequence. Sequence identity is calculated as described below. In particular, an amino acid sequence variant has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 70%, at least 75%, preferably at least 80%, more preferably at least 85%, even more preferably at least 90%, particularly preferably at least 95%, most preferably at least 99% identical to the reference sequence. For example, variant sequences which are at least 90% identical have no more than 10 alterations, i.e. any combination of deletions, insertions or substitutions, per 100 amino acids of the reference sequence.

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA can include cDNA, genomic DNA, synthetic DNA, and semi-synthetic DNA.

As used herein, the term "an effective amount" refers to an amount that is sufficient to achieve or at least partially achieve a desired effect. For example, an effective amount for preventing a disease (e.g., cancer) refers to an amount that is sufficient to prevent, suppress or delay the development of the disease; a therapeutically effective amount refers to an amount that is sufficient to cure or at least partially suppress a disease and its complications in a patient with the disease. For example, an effective amount refers to at least an amount effective, at dosages and for periods of time necessary, to achieve the desired result, e.g., an enhanced immune response to an antigen, an amplification of vaccine immunity, an inhibition of tumor growth and metastasis, etc. An effective amount can be provided in one or more administrations. Determination of such an effective amount is completely within the ability of a person skilled in the art.

For example, an amount effective for a therapeutic use depends on the severity degree of a disease to be treated, general state of the immune system in a patient, general conditions of a patient, such as age, body weight and gender, administration routes of drugs, additional therapies used simultaneously, and the like.

As used herein, the term "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to a disease, e.g., cancer, will be enhanced and/or the clinical severity of the disease reduced. Such protection will be demonstrated by either a reduction in number or severity of, or lack of one or more of the symptoms associated with the disease.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. (Remington: *The Science and Practice of Pharmacy,* 22nd Edition, by Pharmaceutical Press, 2013) describes various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; and phosphate buffer solutions, as well as other non-toxic compatible lubricants such as sodium lauryl sulfate and magnesium stearate, as well as coloring agents, releasing agents, coating agents, preservatives and antioxidants can also be present in the composition, according to the judgment of the formulator.

As used herein, a "fragment" of an antigen comprises at least 10 consecutive amino acids of the antigen, preferably at least 15 consecutive amino acids of the antigen, more preferably at least 20 consecutive amino acids of the antigen, even more preferably at least 25 consecutive amino acids of the antigen and most preferably at least 30 consecutive amino acids of the antigen. A "sequence variant" is as defined above, namely a sequence variant has an (amino acid) sequence which is at least 70%, at least 75%, preferably at least 80%, more preferably at least 85%, even more preferably at least 90%, particularly preferably at least 95%, most preferably at least 99% identical to the reference sequence. A "functional" sequence variant means in the context of an antigen/antigen fragment/epitope, that the function of the epitope(s), e.g. comprised by the antigen (fragment), is not impaired or abolished. Preferably, however, the amino acid sequence of the epitope(s), e.g. comprised by the cancer/tumor antigen (fragment) as described herein, is not mutated and, thus, identical to the reference epitope sequence.

As used herein, an amino acid sequence "sharing a sequence identity" of at least, for example, 95% to a query amino acid sequence of the present invention, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted, preferably within the above definitions of variants or fragments. The same, of course, also applies similarly to nucleic acid sequences.

For (amino acid or nucleic acid) sequences without exact correspondence, a "% identity" of a first sequence may be determined with respect to a second sequence. In general, these two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length.

Methods for comparing the identity and homology of two or more sequences are well known in the art. The percentage to which two sequences are identical can e.g. be determined using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S.A 85, 2444-2448). Sequences which are identical to other sequences to a certain extent can be identified by these programs. Furthermore, programs available in the Wisconsin Sequence Analysis Package, version 9.1 (Devereux et al., 1984, Nucleic Acids Res., 387-395), for example the programs BESTFIT and GAP, may be used to determine the % identity between two polynucleotides and the % identity and the % homology or identity between two polypeptide sequences. BESTFIT uses the "local homology" algorithm of (Smith and Waterman (1981), J. Mol. Biol. 147, 195-197) and finds the best single region of similarity between two sequences.

Proteins or molecules of the MHC are proteins capable of binding peptides that result from the proteolytic cleavage of protein antigens and representing potential T-cell epitopes, transporting them to the cell surface and presenting them there to specific cells, in particular cytotoxic T-lymphocytes or T-helper cells. The MHC of an individual's genome comprises the genetic region whose gene products expressed on the cell surface are important for binding and presenting endogenous and/or foreign antigens for regulating immune response. The major histocompatibility complex is classified into two gene groups coding for different proteins, namely molecules of MHC class I and molecules of MHC class II. The molecules of the two MHC classes are specialized for different antigen sources. The molecules of MHC class I present endogenously synthesized antigens, for example viral proteins and tumor antigens.

A "vaccine" is a material, such as a protein, a nucleic acid, or an inactivated or weakened pathogen, that is administered to a vertebrate host, such as a mammal, e.g., a human, to stimulates the host's immune system to recognize the pathogen (e.g., a virus or a bacterium) or a malignancy, such as tumor. A "therapeutic vaccine" is a vaccine administered to a vertebrate host which already has the disease being targeted and is designed to induce an immune response that causes disease regression, delayed disease progression, prolonged disease-free survival and/or overall survival. A "prophylactic vaccine" is administered to a healthy host and is designed to induce an immune response that will prevent the disease or ameliorate its effects.

Definitions of common terms in cell biology and molecular biology can be found in The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present disclosure is performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); and Current Protocols in Protein Science (CPPS) (John E. Coligan, et. al., ed., John Wiley and Sons, Inc.), which are all incorporated by reference herein in their entireties. As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" means to decrease, suppress, attenuate, diminish, arrest, or stabilize the development or progression of a disease (e.g., a disease or disorder delineated herein), lessen the severity of the disease or improve the symptoms associated with the disease. Treatment includes treating a symptom of a disease, disorder or condition.

As used herein, "preventing" a disorder or condition refers to a treatment that, in a statistical sample, reduces the occurrence of the disorder or condition in the treated sample relative to an untreated control sample, or delays the onset or reduces the severity of one or more symptoms of the disorder or condition relative to the untreated control sample.

Other aspects of the disclosure relate to a method of cancer treatment by inducing humoral and cellular immune responses against cancer cells in a patient that includes the steps of genetically sequencing a tumor-tissue sample from a patient to identify a plurality of neoantigens present in the tumor-tissue sample, and wherein the neoantigens include tumor-associated genetic mutation peptides. At least one neoantigen is selected based upon a predicted affinity for binding to the MHC of the patient, wherein the corresponding MHC proteins on the surface of the antigen-presenting cells of the patient bind and present the neoantigens to helper and effector T cells of the patient's immune system. Resultantly, the patient's immune system then directs an effective immune response to the cancer cells in a patient. To identify those neoantigens that have the highest affinity for binding to the particular patient's MHC, a genetic sequencing (i.e., nucleic acid) is performed on the biopsy material to identify the full range of genetic mutations (i.e., neoantigens), present in the proteins associated with the biopsy material. Again, the genetic sequencing of a patient's cancer sample may be performed by techniques readily known to one skilled in the art or by using standard procedures, as described above.

According to another aspect, the method of cancer treatment by inducing humoral and cellular immune responses against cancer cells in a patient may include administering the vaccine to the patient at a prescribed dose by intradermal, subcutaneous, intramuscular, intranodal, or intra-tumoral injection, or any combination thereof. According to another aspect, the patient receives multiple vaccine injections at separate sites or the patient may receive multiple vaccine injections at the same site. According to yet another aspect, the patient receives multiple vaccinations at prescribed time intervals. According to other aspects, the time intervals may include time intervals such as every 1, 2, 3, or 4 weeks or every 2 to 4 weeks.

Sequences and SEQ ID Numbers

In the SEQ ID Nos. 1-10 below corresponding to variants of human STINGΔTM, the Leucine indicated in bold and underlined (L) corresponds to amino acid 139 in the full-length WT human STING (SEQ ID NO: 11), which is also underlined and in bold.

SEQ ID NO: 1

[hSTINGΔTM (human STING amino acids 139-379)]

Type: PRT

Length: 241

Organism: artificial sequence

LAPAEISAVCEKGNFNVAHGLAWSYYIGYLRLILPELQARIRTYNQHYN

NLLRGAVSQRLYILLPLDCGVPDNLSMADPNIRFLDKLPQQTGDRAGIK

DRVYSNSIYELLENGQRAGTCVLEYATPLQTLFAMSQYSQAGFSREDRL

EQAKLFCRTLEDILADAPESQNNCRLIAYQEPADDSSFSLSQEVLRHLR

QEEKEEVTVGSLKTSAVPSTSTMSQEPELLISGMEKPLPLRTDFS

SEQ ID NO: 2

[hSTINGΔTM TEV-cleaved]

Type: PRT

Length: 242

Organism: artificial sequence

SLAPAEISAVCEKGNFNVAHGLAWSYYIGYLRLILPELQARIRTYNQHY

NNLLRGAVSQRLYILLPLDCGVPDNLSMADPNIRFLDKLPQQTGDRAGI

KDRVYSNSIYELLENGQRAGTCVLEYATPLQTLFAMSQYSQAGFSREDR

LEQAKLFCRTLEDILADAPESQNNCRLIAYQEPADDSSFSLSQEVLRHL

RQEEKEEVTVGSLKTSAVPSTSTMSQEPELLISGMEKPLPLRTDFS

SEQ ID NO: 3
[hSTINGΔTM S366A]
Type: PRT
Length: 241
Organism: artificial sequence LAPAEISAVCEKGNFNVAHGLAWSYYIGYLRLILPELQARIRTYNQHYN
NLLRGAVSQRLYILLPLDCGVPDNLSMADPNIRFLDKLPQQTGDRAGIK
DRVYSNSIYELLENGQRAGTCVLEYATPLQTLFAMSQYSQAGFSREDRL
EQAKLFCRTLEDILADAPESQNNCRLIAYQEPADDSSFSLSQEVLRHLR
QEEKEEVTVGSLKTSAVPSTSTMSQEPELLIAGMEKPLPLRTDFS SEQ ID NO: 4
[hSTINGΔTM S366A TEV-cleaved]
Type: PRT
Length: 264
Organism: artificial sequence SLAPAEISAVCEKGNFNVAHGLAWSYYIGYLRLILPELQARIRTYNQHY
NNLLRGAVSQRLYILLPLDCGVPDNLSMADPNIRFLDKLPQQTGDRAGI
KDRVYSNSIYELLENGQRAGTCVLEYATPLQTLFAMSQYSQAGFSREDR
LEQAKLFCRTLEDILADAPESQNNCRLIAYQEPADDSSFSLSQEVLRHL
RQEEKEEVTVGSLKTSAVPSTSTMSQEPELLIAGMEKPLPLRTDFS SEQ ID No: 5
[hSTINGΔTM L374A]
Type: PRT
Length: 241
Organism: artificial sequence LAPAEISAVCEKGNFNVAHGLAWSYYIGYLRLILPELQARIRTYNQHYN
NLLRGAVSQRLYILLPLDCGVPDNLSMADPNIRFLDKLPQQTGDRAGIK
DRVYSNSIYELLENGQRAGTCVLEYATPLQTLFAMSQYSQAGFSREDRL
EQAKLFCRTLEDILADAPESQNNCRLIAYQEPADDSSFSLSQEVLRHLR
QEEKEEVTVGSLKTSAVPSTSTMSQEPELLISGMEKPLPARTDFS SEQ ID No: 6
[hSTINGΔTM L374A TEV-cleaved]
Type: PRT
Length: 242
Organism: artificial sequence SLAPAEISAVCEKGNFNVAHGLAWSYYIGYLRLILPELQARIRTYNQHY
NNLLRGAVSQRLYILLPLDCGVPDNLSMADPNIRFLDKLPQQTGDRAGI
KDRVYSNSIYELLENGQRAGTCVLEYATPLQTLFAMSQYSQAGFSREDR
LEQAKLFCRTLEDILADAPESQNNCRLIAYQEPADDSSFSLSQEVLRHL
RQEEKEEVTVGSLKTSAVPSTSTMSQEPELLISGMEKPLPARTDFS SEQ ID NO: 7
[hSTINGΔTM R238A/Y240A]
Type: PRT
Length: 241
Organism: artificial sequence LAPAEISAVCEKGNFNVAHGLAWSYYIGYLRLILPELQARIRTYNQHYN
NLLRGAVSQRLYILLPLDCGVPDNLSMADPNIRFLDKLPQQTGDRAGIK
DAVASNSIYELLENGQRAGTCVLEYATPLQTLFAMSQYSQAGFSREDRL
EQAKLFCRTLEDILADAPESQNNCRLIAYQEPADDSSFSLSQEVLRHLR
QEEKEEVTVGSLKTSAVPSTSTMSQEPELLISGMEKPLPLRTDFS SEQ ID NO: 8
[hSTINGΔTM R238A/Y240A TEV-cleaved]
Type: PRT
Length: 242
Organism: artificial sequence SLAPAEISAVCEKGNFNVAHGLAWSYYIGYLRLILPELQARIRTYNQHY
NNLLRGAVSQRLYILLPLDCGVPDNLSMADPNIRFLDKLPQQTGDRAGI
KDAVASNSIYELLENGQRAGTCVLEYATPLQTLFAMSQYSQAGFSREDR
LEQAKLFCRTLEDILADAPESQNNCRLIAYQEPADDSSFSLSQEVLRHL
RQEEKEEVTVGSLKTSAVPSTSTMSQEPELLISGMEKPLPLRTDFS SEQ ID NO: 9
[hSTINGΔTM ΔC9 (deletion of the last 9 amino acids from C-terminus)]
Type: PRT
Length: 232
Organism: artificial sequence LAPAEISAVCEKGNFNVAHGLAWSYYIGYLRLILPELQARIRTYNQHYN
NLLRGAVSQRLYILLPLDCGVPDNLSMADPNIRFLDKLPQQTGDRAGIK
DRVYSNSIYELLENGQRAGTCVLEYATPLQTLFAMSQYSQAGFSREDRL
EQAKLFCRTLEDILADAPESQNNCRLIAYQEPADDSSFSLSQEVLRHLR
QEEKEEVTVGSLKTSAVPSTSTMSQEPELLISGMEK SEQ ID NO: 10
[hSTINGΔTM ΔC9 TEV-cleaved]
Type: PRT
Length: 233
Organism: artificial sequence SLAPAEISAVCEKGNFNVAHGLAWSYYIGYLRLILPELQARIRTYNQHY
NNLLRGAVSQRLYILLPLDCGVPDNLSMADPNIRFLDKLPQQTGDRAGI
KDRVYSNSIYELLENGQRAGTCVLEYATPLQTLFAMSQYSQAGFSREDR
LEQAKLFCRTLEDILADAPESQNNCRLIAYQEPADDSSFSLSQEVLRHL
RQEEKEEVTVGSLKTSAVPSTSTMSQEPELLISGMEK SEQ ID NO: 11
[hSTING wild type]
Type: PRT
Length: 379
Organism: *Homo sapiens*

```
MPHSSLHPSIPCPRGHGAQKAALVLLSACLVTLWGLGEPPEHTLRYLVL
HLASLQLGLLLNGVCSLAEELRHIHSRYRGSYWRTVRACLGCPLRRGAL
LLLSIYFYYSLPNAVGPPFTWMLALLGLSQALNILLGLKGLAPAEISAV
CEKGNFNVAHGLAWSYYIGYLRLILPELQARIRTYNQHYNNLLRGAVSQ
RLYILLPLDCGVPDNLSMADPNIRFLDKLPQQTGDRAGIKDRVYSNSIY
ELLENGQRAGTCVLEYATPLQTLFAMSQYSQAGFSREDRLEQAKLFCRT
LEDILADAPESQNNCRLIAYQEPADDSSFSLSQEVLRHLRQEEKEEVTV
GSLKTSAVPSTSTMSQEPELLISGMEKPLPLRTDFS
```

SEQ ID NO: 12
[hSTING HAQ (R71H-G230A-R293Q)]
Type: PRT
Length: 379
Organism: *Homo sapiens*

```
MPHSSLHPSIPCPRGHGAQKAALVLLSACLVTLWGLGEPPEHTLRYLVL
HLASLQLGLLLNGVCSLAEELHHIHSRYRGSYWRTVRACLGCPLRRGAL
LLLSIYFYYSLPNAVGPPFTWMLALLGLSQALNILLGLKGLAPAEISAV
CEKGNFNVAHGLAWSYYIGYLRLILPELQARIRTYNQHYNNLLRGAVSQ
RLYILLPLDCGVPDNLSMADPNIRFLDKLPQQTADRAGIKDRVYSNSIY
ELLENGQRAGTCVLEYATPLQTLFAMSQYSQAGFSREDRLEQAKLFCQT
LEDILADAPESQNNCRLIAYQEPADDSSFSLSQEVLRHLRQEEKEEVTV
GSLKTSAVPSTSTMSQEPELLISGMEKPLPLRTDFS
```

In the SEQ ID Nos. 13-22 below corresponding to variants of murine STINGΔTM, the Leucine indicated in bold and underlined (L) corresponds to amino acid 138 in the full-length WT murine STING (SEQ ID NO: 23), also underlined and in bold.

SEQ ID NO: 13
[mSTINGΔTM (mouse STING amino acids 138-378)]
Type: PRT
Length: 241
Organism: artificial sequence

```
LTPAEVSAVCEEKKLNVAHGLAWSYYIGYLRLILPGLQARIRMFNQLHN
NMLSGAGSRRLYILFPLDCGVPDNLSVVDPNIRFRDMLPQQNIDRAGIK
NRVYSNSVYEILENGQPAGVCILEYATPLQTLFAMSQDAKAGFSREDRL
EQAKLFCRTLEEILEDVPESRNNCRLIVYQEPTDGNSFSLSQEVLRHIR
QEEKEEVTMNAPMTSVAPPPSVLSQEPRLLISGMDQPLPLRTDLI
```

SEQ ID NO: 14
[mSTINGΔTM TEV-cleaved]
Type: PRT
Length: 242
Organism: artificial sequence

```
SLTPAEVSAVCEEKKLNVAHGLAWSYYIGYLRLILPGLQARIRMFNQLH
NNMLSGAGSRRLYILFPLDCGVPDNLSVVDPNIRFRDMLPQQNIDRAGI
KNRVYSNSVYEILENGQPAGVCILEYATPLQTLFAMSQDAKAGFSREDR
LEQAKLFCRTLEEILEDVPESRNNCRLIVYQEPTDGNSFSLSQEVLRHI
RQEEKEEVTMNAPMTSVAPPPSVLSQEPRLLISGMDQPLPLRTDLI
```

SEQ ID NO: 15
[mSTINGΔTM 5365A]
Type: PRT
Length: 241
Organism: artificial sequence

```
LTPAEVSAVCEEKKLNVAHGLAWSYYIGYLRLILPGLQARIRMFNQLHN
NMLSGAGSRRLYILFPLDCGVPDNLSVVDPNIRFRDMLPQQNIDRAGIK
NRVYSNSVYEILENGQPAGVCILEYATPLQTLFAMSQDAKAGFSREDRL
EQAKLFCRTLEEILEDVPESRNNCRLIVYQEPTDGNSFSLSQEVLRHIR
QEEKEEVTMNAPMTSVAPPPSVLSQEPRLLIAGMDQPLPLRTDLI
```

SEQ ID NO: 16
[mSTINGΔTM S365A TEV-cleaved]
Type: PRT
Length: 242
Organism: artificial sequence

```
SLTPAEVSAVCEEKKLNVAHGLAWSYYIGYLRLILPGLQARIRMFNQLH
NNMLSGAGSRRLYILFPLDCGVPDNLSVVDPNIRFRDMLPQQNIDRAGI
KNRVYSNSVYEILENGQPAGVCILEYATPLQTLFAMSQDAKAGFSREDR
LEQAKLFCRTLEEILEDVPESRNNCRLIVYQEPTDGNSFSLSQEVLRHI
RQEEKEEVTMNAPMTSVAPPPSVLSQEPRLLIAGMDQPLPLRTDLI
```

SEQ ID NO: 17
[mSTINGΔTM L373A]
Type: PRT
Length: 241
Organism: artificial sequence

```
LTPAEVSAVCEEKKLNVAHGLAWSYYIGYLRLILPGLQARIRMFNQLHN
NMLSGAGSRRLYILFPLDCGVPDNLSVVDPNIRFRDMLPQQNIDRAGIK
NRVYSNSVYEILENGQPAGVCILEYATPLQTLFAMSQDAKAGFSREDRL
EQAKLFCRTLEEILEDVPESRNNCRLIVYQEPTDGNSFSLSQEVLRHIR
QEEKEEVTMNAPMTSVAPPPSVLSQEPRLLISGMDQPLPARTDLI
```

SEQ ID NO: 18
[mSTINGΔTM L373A TEV-cleaved]
Type: PRT
Length: 242
Organism: artificial sequence SLTPAEVSAVCEEKKLNVAHGLAWSYYIGYLRLILPGLQARIRMFNQLH
NNMLSGAGSRRLYILFPLDCGVPDNLSVVDPNIRFRDMLPQQNIDRAGI
KNRVYSNSVYEILENGQPAGVCILEYATPLQTLFAMSQDAKAGFSREDR
LEQAKLFCRTLEEILEDVPESRNNCRLIVYQEPTDGNSFSLSQEVLRHI
RQEEKEEVTMNAPMTSVAPPPSVLSQEPRLLISGMDQPLPARTDLI SEQ ID NO: 19
[mSTINGΔTM R237A-Y239A]
Type: PRT
Length: 241
Organism: artificial sequence LTPAEVSAVCEEKKLNVAHGLAWSYYIGYLRLILPGLQARIRMFNQLHN
NMLSGAGSRRLYILFPLDCGVPDNLSVVDPNIRFRDMLPQQNIDRAGIK
NAVASNSVYEILENGQPAGVCILEYATPLQTLFAMSQDAKAGFSREDRL
EQAKLFCRTLEEILEDVPESRNNCRLIVYQEPTDGNSFSLSQEVLRHIR
QEEKEEVTMNAPMTSVAPPPSVLSQEPRLLISGMDQPLPLRTDLI SEQ ID NO: 20
[mSTINGΔTM R237A-Y239A TEV-cleaved]
Type: PRT
Length: 242
Organism: artificial sequence SLTPAEVSAVCEEKKLNVAHGLAWSYYIGYLRLILPGLQARIRMFNQLH
NNMLSGAGSRRLYILFPLDCGVPDNLSVVDPNIRFRDMLPQQNIDRAGI
KNAVASNSVYEILENGQPAGVCILEYATPLQTLFAMSQDAKAGFSREDR
LEQAKLFCRTLEEILEDVPESRNNCRLIVYQEPTDGNSFSLSQEVLRHI
RQEEKEEVTMNAPMTSVAPPPSVLSQEPRLLISGMDQPLPLRTDLI SEQ ID NO: 21
[mSTINGΔTM ΔC9 (deletion of the last 9 amino acids from C-terminus)]
Type: PRT
Length: 232
Organism: artificial sequence LTPAEVSAVCEEKKLNVAHGLAWSYYIGYLRLILPGLQARIRMFNQLHN
NMLSGAGSRRLYILFPLDCGVPDNLSVVDPNIRFRDMLPQQNIDRAGIK
NRVYSNSVYEILENGQPAGVCILEYATPLQTLFAMSQDAKAGFSREDRL
EQAKLFCRTLEEILEDVPESRNNCRLIVYQEPTDGNSFSLSQEVLRHIR
QEEKEEVTMNAPMTSVAPPPSVLSQEPRLLISGMDQ SEQ ID NO: 22
[mSTINGΔTM ΔC9 with His-tags and TEV cleave site]
Type: PRT
Length: 233
Organism: artificial sequence SLTPAEVSAVCEEKKLNVAHGLAWSYYIGYLRLILPGLQARIRMFNQLH
NNMLSGAGSRRLYILFPLDCGVPDNLSVVDPNIRFRDMLPQQNIDRAGI
KNRVYSNSVYEILENGQPAGVCILEYATPLQTLFAMSQDAKAGFSREDR
LEQAKLFCRTLEEILEDVPESRNNCRLIVYQEPTDGNSFSLSQEVLRHI
RQEEKEEVTMNAPMTSVAPPPSVLSQEPRLLISGMDQ SEQ ID NO: 23
[mSTING wild type]
Type: PRT
Length: 378
Organism: *Mus musculus*

MPYSNLHPAIPRPRGHRSKYVALIFLVASLMILWVAKDPPNHTLKYLAL
HLASHELGLLLKNLCCLAEELCHVQSRYQGSYWKAVRACLGCPIHCMAM
ILLSSYFYFLQNTADIYLSWMFGLLVLYKSLSMLLGLQSLTPAEVSAVC
EEKKLNVAHGLAWSYYIGYLRLILPGLQARIRMFNQLHNNMLSGAGSRR
LYILFPLDCGVPDNLSVVDPNIRFRDMLPQQNIDRAGIKNRVYSNSVYE
ILENGQPAGVCILEYATPLQTLFAMSQDAKAGFSREDRLEQAKLFCRTL
EEILEDVPESRNNCRLIVYQEPTDGNSFSLSQEVLRHIRQEEKEEVTMN
APMTSVAPPPSVLSQEPRLLISGMDQPLPLRTDLI

SEQ ID NO: 24
[hSTING transmembrane domain]
Type: PRT
Length: 138
Organism: artificial sequence MPHSSLHPSIPCPRGHGAQKAALVLLSACLVTLWGLGEPPEHTLRYLVL
HLASLQLGLLLNGVCSLAEELRHIHSRYRGSYWRTVRACLGCPLRRGAL
LLLSIYFYYSLPNAVGPPFTWMLALLGLSQALNILLGLKG SEQ ID NO: 25
[SIINFEKL]
Type: PRT
Length: 20
Organism: artificial sequence
GLEQLESIINFEKLTEWTSS DNA sequences of STING alleles: WT Human STING (SEQ ID NO: 26), REF Human STING (SEQ ID NO: 27), and AQ Human Sting (SEQ ID NO: 28).

SEQ ID NO: 26
[WT Human STING]
Type: DNA
Length: 1140
Organism: *Homo sapiens*

Atgccccactccagcctgcatccatccatcccgtgtcccaggggtcacg
gggcccagaaggcagccttggttctgctgagtgcctgcctggtgaccat
tgggggctaggagagccaccagagcacactctccggtacctggtgctcc -continued acctagcctccctgcagctgggactgctgttaaacggggtctgcagcct ggctgaggagctgcgccacatccactccaggtaccggggcagctactgg aggactgtgcgggcctgcctgggctgccccctccgccgtggggccctgt tgctgctgtccatctatttctactactccctcccaaatgcggtcggccc gcccttcacttggatgcttgccctcctgggcctctcgcaggcactgaac atcctcctgggcctcaagggcctggccccagctgagatctctgcagtgt gtgaaaaagggaatttcaacgtggcccatgggctggcatggtcatatta catcggatatctgcggctgatcctgccagagctccaggcccggattcga acttacaatcagcattacaacaacctgctacggggtgcagtgagccagc ggctgtatattctcctcccattggactgtggggtgcctgataacctgag tatggctgaccccaacattcgcttcctggataaactgccccagcagacc ggtgaccgggctggcatcaaggatcgggtttacagcaacagcatctatg agatctggagaacgggcagcgggcgggcacctgtgtcctggagtacgcc accccccttgcagactttgtttgccatgtcacaatacagtcaagctggct ttagccgggaggataggcttgagcaggccaaactatctgccggacactt gaggacatcctggcagatgcccctgagtctcagaacaactgccgcctca ttgcctaccaggaacctgcagatgacagcagatctcgctgtcccaggag gttctccggcacctgcggcaggaggaaaaggaagaggttactgtgggca gcttgaagacctcagcggtgcccagtacctccacgatgtcccaagagcc tgagctcctcatcagtggaatggaaaagcccctccctctccgcacggat ttctcttga SEQ ID NO: 27
[REF Human STING]
Type: DNA
Length: 1140
Organism: *Homo sapiens* atgccccactccagcctgcatccatccatcccgtgtcccaggggtcacg gggcccagaaggcagccttggttctgctgagtgcctgcctggtgaccat tgggggctaggagagccaccagagcacactctccggtacctggtgctcc acctagcctccctgcagctgggactgctgttaaacggggtctgcagcct ggctgaggagctgcgccacatccactccaggtaccggggcagctactgg aggactgtgcgggcctgcctgggctgccccctccgccgtggggccctgt tgctgctgtccatctatttctactactccctcccaaatgcggtcggccc gccatcacttggatgatgccctcctgggcctctcgcaggcactgaacat cctcctgggcctcaagggcctggccccagctgagatctctgcagtgtgt gaaaaagggaatttcaacgtggcccatgggctggcatggtcatattaca tcggatatctgcggctgatcctgccagagctccaggcccggattcgaac ttacaatcagcattacaacaacctgctacggggtgcagtgagccagcgg ctgtatattctcctcccattggactgtggggtgcctgataacctgagta tggctgaccccaacattcgatcctggataaactgccccagcagaccggt gaccatgctggcatcaaggatcgggtttacagcaacagcatctatgagc ttctggagaacgggcagcgggcgggcacctgtgtcctggagtacgccac cccatgcagactttgtttgccatgtcacaatacagtcaagctggcttta gccgggaggataggcttgagcaggccaaactatctgccggacacttgag gacatcctggcagatgcccctgagtctcagaacaactgccgcctcattg cctaccaggaacctgcagatgacagcagatctcgctgtcccaggaggtt ctccggcacctgcggcaggaggaaaaggaagaggttactgtgggcagct tgaagacctcagcggtgcccagtacctccacgatgtcccaagagcctga gctcctcatcagtggaatggaaaagcccctccctctccgcacggatttc tcttga SEQ ID NO: 28
[AQ Human STING]
Type: DNA
Length: 1140
Organism: *Homo sapiens*

Atgccccactccagcctgcatccatccatcccgtgtcccaggggtcacg gggcccagaaggcagccttggttctgctgagtgcctgcctggtgaccct ttgggggctaggagagccaccagagcacactctccggtacctggtgctc cacctagcctccctgcagctgggactgctgttaaacggggtctgcagcc tggctgaggagctgcgccacatccactccaggtaccggggcagctactg gaggactgtgcgggcctgcctgggctgccccctccgccgtggggccctg ttgctgctgtccatctatttctactactccctcccaaatgcggtcggcc cgcccttcacttggatgcttgccctcctgggcctctcgcaggcactgaa catcctcctgggcctcaagggcctggccccagctgagatctctgcagtg tgtgaaaaagggaatttcaacgtggcccatgggctggcatggtcatatt acatcggatatctgcggctgatcctgccagagctccaggcccggattcg aacttacaatcagcattacaacaacctgctacggggtgcagtgagccag cggctgtatattctcctcccattggactgtggggtgcctgataacctga gtatggctgaccccaacattcgcttcctggataaactgccccagcagac cgctgaccgagctggcatcaaggatcgggtttacagcaacagcatctat gagcttctggagaacgggcagcgggcgggcacctgtgtcctggagtacg ccaccccccttgcagactttgrngccatgtcacaatacagtcaagctggc tttagccgggaggataggcttgagcaggccaaactcttctgccagacac ttgaggacatcctggcagatgcccctgagtctcagaacaactgccgcct cattgcctaccaggaacctgcagatgacagcagcttctcgctgtcccag gaggttctccggcacctgcggcaggaggaaaaggaagaggttactgtgg gcagcttgaagacctcagcggtgcccagtacctccacgatgtcccaaga gcctgagctcctcatcagtggaatggaaaagcccctccctctccgcacg gatttctcttga Agonists (i.e. cyclic dinucleotides) of the stimulator of interferon gene (STING) pathway have been gaining increasing attention as promising therapeutics to augment the maturation of dendritic cells (DCs) and the cross-presentation of DCs to cytotoxic T cells, as well as to overcome resistance against immune checkpoint inhibitors.

Cyclic dinucleotides (CDNs) suffer from fast clearance from the tumor microenvironment (TME) and susceptibility to enzymatic degradation. To address these challenges, existing efforts focus on novel biomaterials to improve their bioavailability in the TME, and chemical modifications to increase their metabolic stability. Because CDNs induce immune responses via binding to their common receptor, STING, current efforts fail to solve the following problems: (1) Low or lack of STING expression is frequently detected in certain cancers due to epigenetic silencing and therefore confers insensitivity to CDNs; (2) ~19% of the population exhibits nonsynonymous mutations in STING and is insensitive to natural CDNs; (3) While hydrophobic small molecule drugs can be encapsulated by amphiphilic structures (e.g. micelles), nucleic acids (e.g. DNA and mRNA) can be condensed by ionic polymers or lipid nanoparticles. In contrast, the hydrophilicity and low charge density of CDNs render them difficult to package in existing carriers.

A preassembled CDN-STING complex in the form of a ribonucleoprotein (RNP) addresses the abovementioned problems, based on utilizing RNPs to improve the efficacy of mRNA delivery and RNA interference. In nature, the STING protein forms a dimer to sandwich one CDN ligand with a nanomolar (nM) dissociation constant, which suggests a strong interaction that can achieve great RNP stability from both formulation and delivery perspectives. The STING protein can be genetically fused with a cell penetrating peptide and/or tumor-specific peptide to simultaneously serve as a carrier for CDNs and as a functional complex to activate STING signaling in DCs and the TME. Alternatively, the RNP can be encapsulated by existing delivery platforms that have been developed for protein delivery.

Current efforts to solely increase the bioavailability of CDNs in the TME cannot fully activate STING signaling in tumors when there is low or lack of expression of the CDN receptor STING. For instance, in lung and gastric cancers, low STING expression correlates with cancer progression and poor prognosis. Moreover, ~19% of the population exhibits nonsynonymous mutations in STING and is insensitive to natural CDNs. Additionally, since CDNs must form a bound complex with STING protein inside cells to activate its downstream signaling, codelivery of preassembled CDN/STING complexes can circumvent the requirement for preexisting STING expression.

These techniques described herein can provide a new mode of delivery for STING agonists to greatly enhance therapeutic efficacy by activating STING signaling in multiple cancer types. In addition to acting as a monotherapy, the delivery of RNPs including or consisting of STING and CDNs can be integrated with existing immunotherapy approaches including combination with immune checkpoint inhibitors to mitigate their resistance in a majority of cancer patients, and co-administration with tumor neoantigens to enhance personalized cancer vaccines.

The following Detailed Description references the accompanying drawings which form a part this application, and which show, by way of illustration, specific example implementations. Other implementations may be made without departing from the scope of the disclosure.

An example implementation and corresponding experimental results are provided in Appendix II, which forms a part of this Specification and is hereby incorporated by reference.

Reference numbers in parentheses in Appendix II "( )" refer to the corresponding literature listed in the attached Bibliography which forms a part of this Specification, and the literature is incorporated by reference herein.

Presentation slides are presented in Appendix I, which forms part of this Specification and is hereby incorporated by reference. In Appendix I, In slide 6, 1 million MC38 colon cells were implanted s.c. in 100 ul OptiMEM medium to 6-week old female B6 mice from Jackson lab on Nov. 15, 2017. Mice were injected intratumorally: 1st injection on Nov. 20, 2017: 10 ug cGAMP (cayman), bug cGAMP/20 ug Wt STING (w/w=1:2), bug cdiGMP (cayman), bug cdiGMP/20 ug Wt STING (w/w=1:2), or 20 ug Wt STING alone using RNAimax (5 ul RNAimax per mouse); 2nd injection on Nov. 27, 2017: 10 ug cGAMP (TAMU), bug cGAMP/20 ug Wt STING (w/w=1:2), bug cdiGMP (cayman), bug cdiGMP/20 ug Wt STING (w/w=1:2), or 20 ug Wt STING alone using N4(TEP) (5/1 N/P ratio); 3rd injection on Dec. 4, 2017: 10 ug cGAMP (TAMU), bug cGAMP/20 ug Wt STING (w/w=1:1), bug cdiGMP (cayman), bug cdiGMP/20 ug Wt STING (w/w=1:1), or bug Wt STING alone using Lipofectamine 2000 (5 ul lipofectamine 2000 per mouse). In slide 7, images show 12052017 MC38-bearing mice were photographed 20 days post tumor challenge. In slide 8, some mice from each group of different treatments are singled out.

The literature for which citations appear in the slides of Appendix I, as listed below, are incorporated by reference herein:

i. S Dowdy. Nature Biotechnology 35, 222-229 (2017)
ii. J. Li, et al. ACS Nano. 2017, March
iii. J. Li, et al. Angew Chem Int Ed Engl. 2017, October
iv. J. Li, et al. PNAS. 2018, February
v. H Aini et al. Sci Rep. 2016 Jan. 5; 6:18743
vi. CY Li, et al. Journal of Controlled Release 235 (2016)
vii. Immunity. 2012 Jun. 29; 36(6):1073-86.
viii. Sci Signal. 2012 Mar. 6; 5(214):ra20.

In various embodiments the present invention is

1. A ribonucleoprotein (RNP) complex comprising a recombinant transmembrane (TM)-deficient STING protein and a cyclic dinucleotide (CDN).

2. The RNP complex of claim 1, wherein the CDN is cyclic guanosine monophosphate-adenosine monophosphate (cGAMP).

3. The RNP complex of claim 2, wherein the RNP complex is about 120 kDa molecular weight and comprises a tetramer of cGAMP and transmembrane (TM)-deficient STING protein.

4. A method of treating cancer in a subject by administering to the subject the RNP complex of claim 1 in an amount effective to treat cancer.

5. The method of claim 4, wherein the RNP complex is administered in combination with other immunotherapy treatments.

6. The method of claim 5 wherein the immunotherapy treatment is either administering a checkpoint inhibitor or administering a tumor neoantigen.

7. The method of claim 6, wherein the checkpoint inhibitor is either a PD(L)1 or CTLA4 inhibitor.

8. A method of in vivo activating the STING signaling pathway in a subject by administering to the subject the RNP complex of claim 1.

9. A method of delivering cGAMP to a subject by administering to the subject the RNP complex of claim 1.

10. A method of enhancing the innate and adaptive immune response in a subject by administering to the subject the RNP complex of claim 1.

The stimulator of interferon (IFN) genes (STING) pathway constitutes a highly important part of immune responses against various cancers and infections. Consequently, administration of STING agonists such as cyclic GMP-AMP (cGAMP) has been identified as a promising approach to target these diseases. In cancer cells, STING signaling is frequently impaired by epigenetic silencing of STING; hence, conventional delivery of only its agonist cGAMP may be insufficient to trigger STING signaling. While expression of STING lacking the transmembrane (TM) domain is known to be unresponsive to STING agonists and is dominant negative when coexpressed with the full-length STING inside cells, herein it is observed that the recombinant TM-deficient STING protein complexed with cGAMP could effectively trigger STING signaling when delivered in vitro and in vivo, including in STING-deficient cell lines. Thus, this bio-\inspired method using TM-deficient STING may present a new and universally applicable platform for cGAMP delivery.

In the first embodiment, the present invention is a non-covalent complex, comprising: a tetramer of a recombinant protein; and an agonist of a Stimulator of Interferon Gene (STING) protein or a pharmaceutically acceptable salt thereof, wherein the recombinant protein comprises a STING protein lacking a transmembrane domain (STINGΔTM protein).

In a first aspect of the first embodiment, the STINGΔTM protein is a murine STINGΔTM protein. For example, the STINGΔTM protein has an amino acid sequence selected from SEQ ID NOs. 13-22.

In a second aspect of the first embodiment, the STINGΔTM protein is a human STINGΔTM protein. For example, the STINGΔTM protein has an amino acid sequence selected from SEQ ID NOs. 1-10. For example, the STINGΔTM protein has an amino acid sequence selected from SEQ ID NOs. 1 or 2, e.g., SEQ ID NO. 1.

In a third aspect of the first embodiment, the STING protein agonist is a cyclic dinucleotide (CDN). For example, the CDN is selected from cyclic dimeric guanosine monophosphate (cdiGMP), cyclic dimeric adenosine monophosphate (cdiAMP), cyclic 2'3'-guanosine monophosphate-adenosine monophosphate (2'3'-cGAMP), cyclic 3'3'-guanosine monophosphate-adenosine monophosphate (3'3'-cGAMP), or a compound represented by one of the following structural formulas:

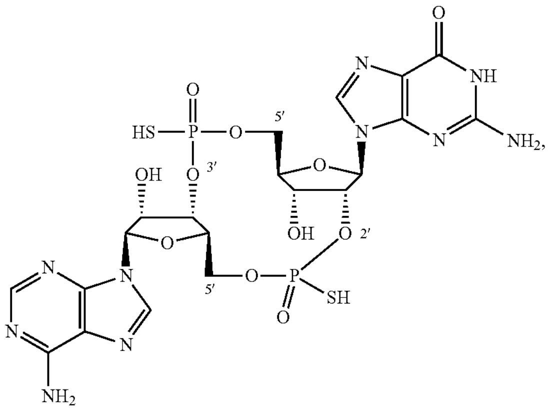

-continued

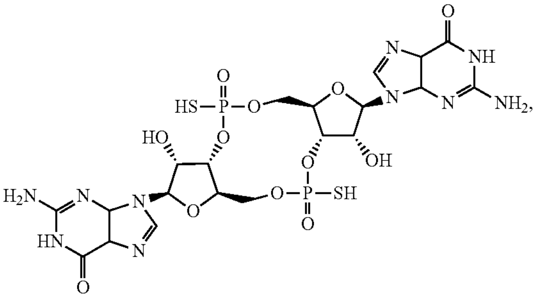

and

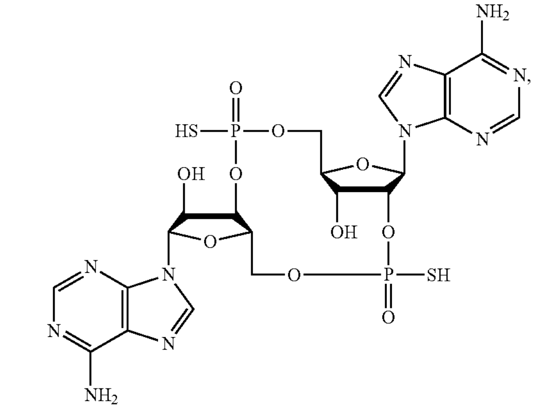

or a pharmaceutically acceptable salt thereof. For example, the CDN is selected from cdiGMP, cdiAMP, 3'3'-cGAMP, or a compound represented by one of the following structural formulas:

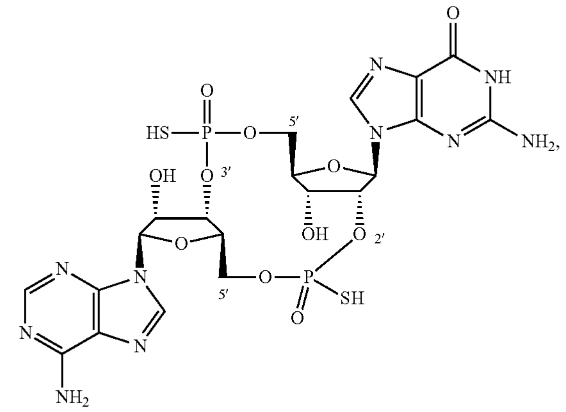

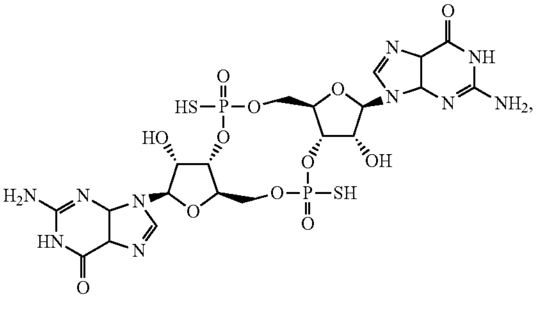

and

-continued

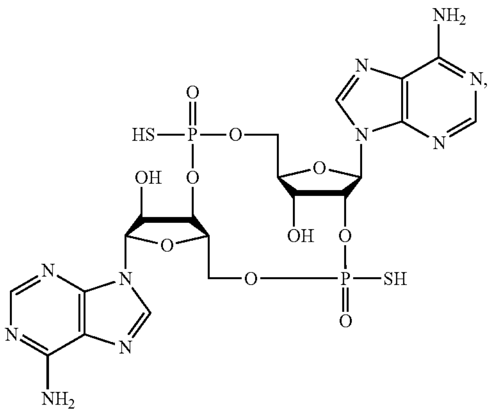

or a pharmaceutically acceptable salt thereof. For example, the CDN is 2'3'-cGAMP. Additionally or alternatively, the CDN is cdiGMP. The remainder of the features and example feature of the variables of the complex are as described above with respect to the first and second aspects of the first embodiment.

Additional CDNs and methods of their synthesis are described, for example, in U.S. Pat. Nos. 10,246,480 and 10,011,630, each of which is incorporated herein by reference in its entirety.

In a fourth aspect of the first embodiment, the STING protein agonist is a compound represented by one of the following structural formulas:

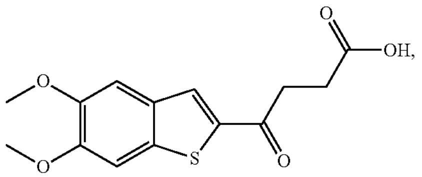

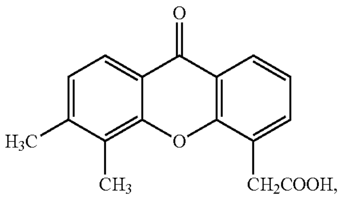

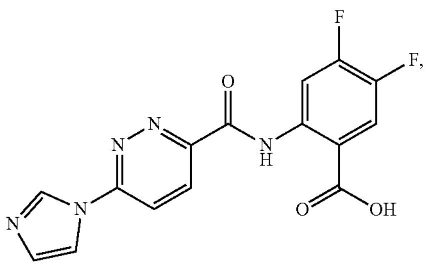

-continued

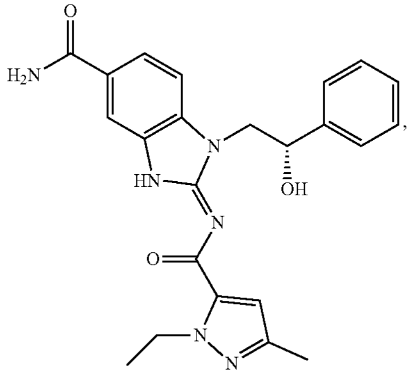

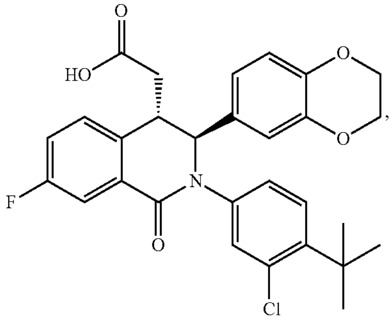

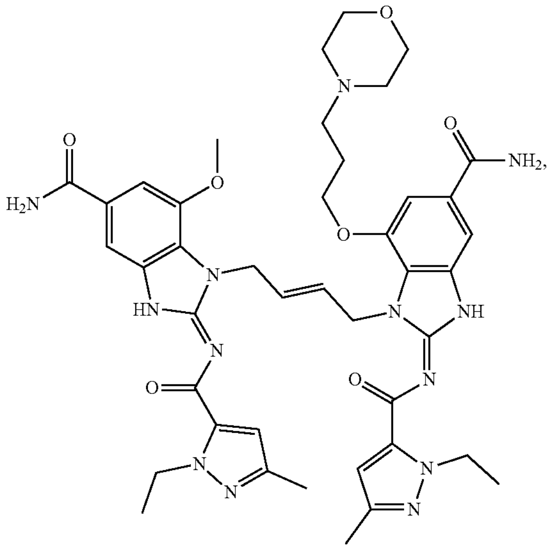

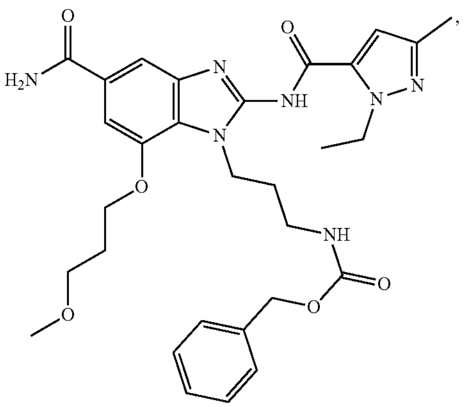

and

-continued

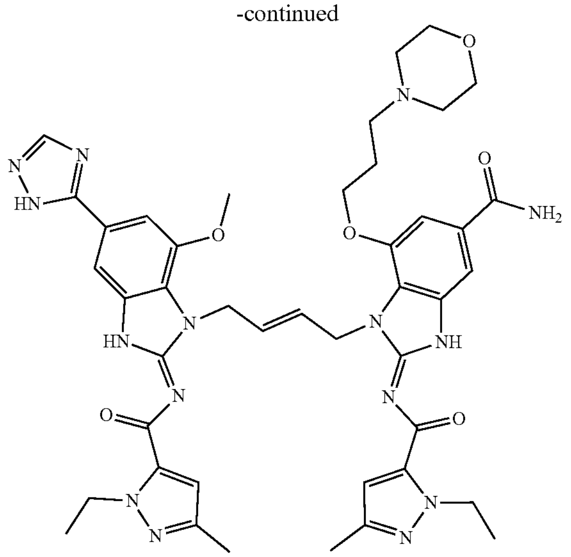

or a pharmaceutically acceptable salt thereof. The remainder of the features and example feature of the variables of the complex are as described above with respect to the first and second aspects of the first embodiment.

In a fifth aspect of the first embodiment, the recombinant protein further comprises a tumor epitope. For example, the tumor epitope is attached to the N-terminus of STINGΔTM. Alternatively, the tumor epitope is attached to the C-terminus of STINGΔTM. For example, the tumor epitope is an epitope of an antigen selected from the group consisting of CMV, EGFRvIII, EphA2, gp100, Her2/neu, IL-13Rα2, survivin, hTert, TRP-2, MAGE-A1, MAGE-A3, YKL-40, brevican, neuroligin 4 and PTPRzl, EpCAM, HER-2, MUC-1, TOMM34, RNF 43, KOC1, VEGFR, βhCG, CEA, TGFβR2, p53, KRas, OGT, CASP5, COA-1, MAGE, SART and IL13Ralpha2, MART-1, tyrosinase, and NY-ESO-1. The remainder of the features and example feature of the variables of the complex are as described above with respect to the first through fourth aspects of the first embodiment.

In a sixth aspect of the first embodiment, the recombinant protein is the STINGΔTM protein having an amino acid sequence selected from SEQ ID NOs: 1 and 2. For example, the recombinant protein is the STINGΔTM protein having an amino acid sequence of SEQ ID NO: 1. Alternatively, the recombinant protein is the STINGΔTM protein having an amino acid sequence of SEQ ID NO: 2. The remainder of the features and example feature of the variables of the complex are as described above with respect to the second through fifth aspects of the first embodiment.

In a seventh aspect of the first embodiment, the recombinant protein is the STINGΔTM protein having an amino acid sequence selected from SEQ ID Nos: 1 and 2; and the agonist of STING protein is 2'3'-cGAMP. For example, the recombinant protein is the STINGΔTM protein having an amino acid sequence of SEQ ID NOs: 1. Alternatively, the recombinant protein is the STINGΔTM protein having an amino acid sequence of SEQ ID NO: 2.

In the second embodiment, the present invention is a pharmaceutical composition comprising the complex described herein with respect to the first embodiment and various aspects thereof.

In the third embodiment, the present invention is a method of treating or preventing cancer in a subject in need thereof, comprising: administering to the subject in need thereof an effective amount of a non-covalent complex, comprising: a recombinant protein; and an agonist of a STING protein or a pharmaceutically acceptable salt thereof, wherein the recombinant protein comprises a STINGΔTM protein.

In a first aspect of the third embodiment, the complex comprises a tetramer of the recombinant protein.

In a second aspect of the third embodiment, the STINGΔTM protein is a human STINGΔTM protein. For example, the STINGΔTM protein has an amino acid sequence selected from SEQ ID Nos: 1-10. For example, the STINGΔTM protein has an amino acid sequence selected from SEQ ID Nos: 1 or 2, e.g., SEQ ID NO: 1. The remainder of the features and example feature of the variables of the method are as described above with respect to the first aspect of the third embodiment.

In a third aspect of the third embodiment, the STING protein agonist is a CDN. For example, the CDN is selected from cdiGMP, cdiAMP, 2'3'-cGAMP, 3'3'-cGAMP, or a compound represented by one of the following structural formulas:

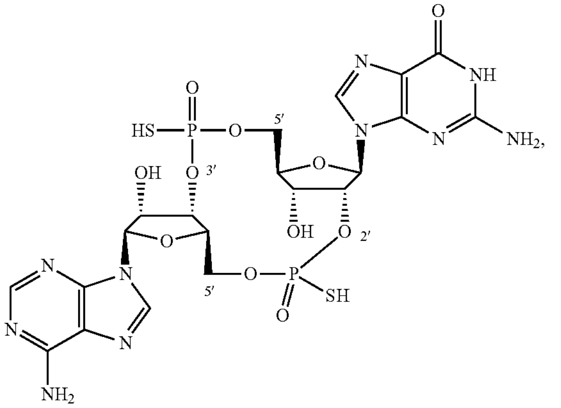

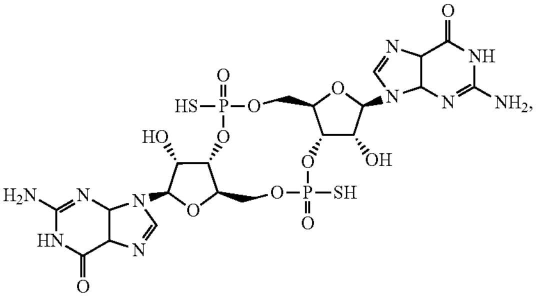

and

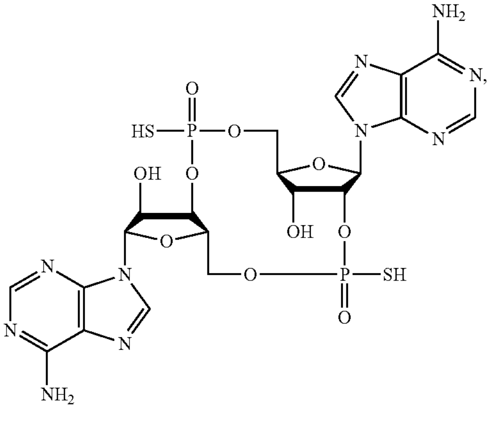

or a pharmaceutically acceptable salt thereof. For example, the CDN is selected from cdiGMP, cdiAMP, 3'3'-cGAMP, or a compound represented by one of the following structural formulas:

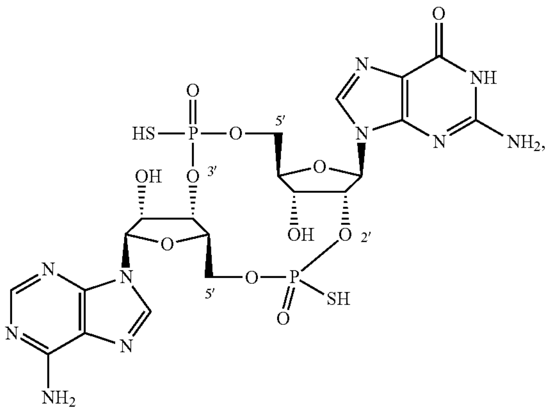

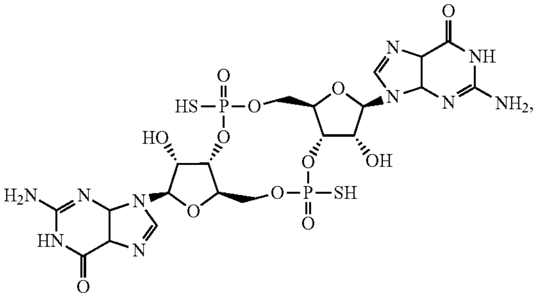

and

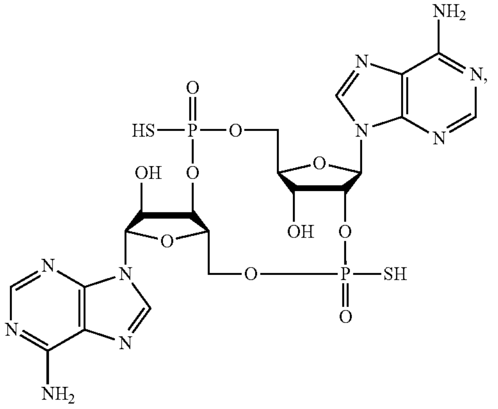

or a pharmaceutically acceptable salt thereof. For example, the CDN is 2'3'-cGAMP. Additionally or alternatively, the CDN is cdiGMP. The remainder of the features and example feature of the variables of the method are as described above with respect to the first and second aspects of the third embodiment.

In a fourth aspect of the third embodiment, the STING protein agonist is a compound represented by one of the following structural formulas:

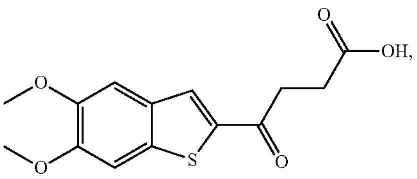

-continued

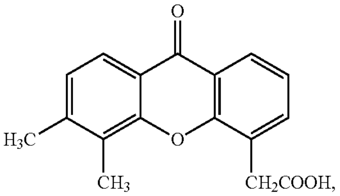

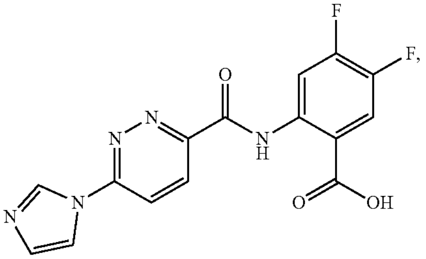

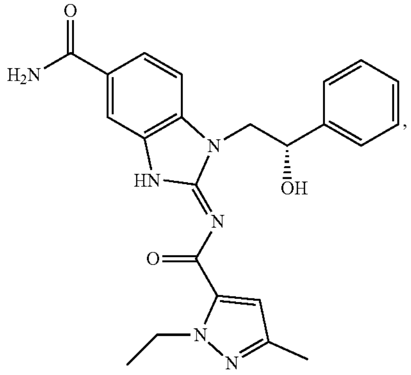

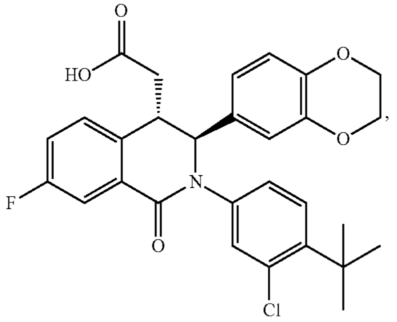

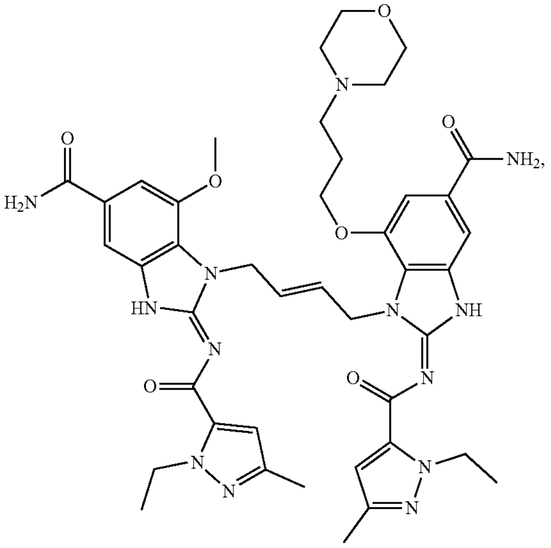

-continued

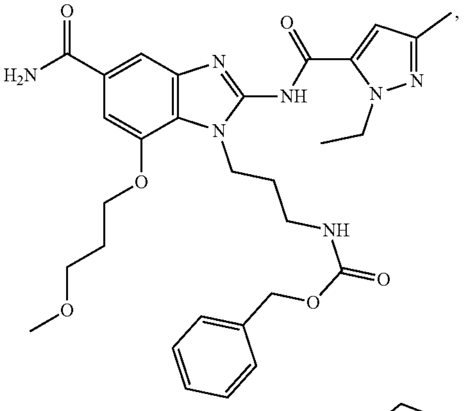

, and

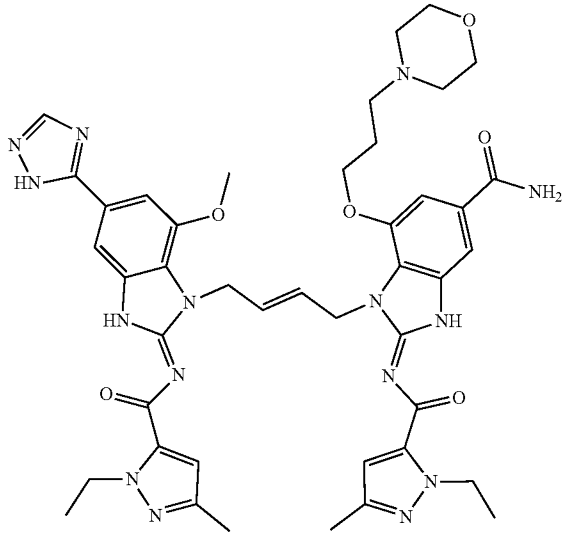

or a pharmaceutically acceptable salt thereof. The remainder of the features and example feature of the variables of the method are as described above with respect to the first and second aspects of the third embodiment.

In a fifth aspect of the third embodiment, the recombinant protein further comprises a tumor epitope. For example, the tumor epitope is attached to the N-terminus of STINGΔTM. Alternatively, the tumor epitope is attached to the C-terminus of STINGΔTM. For example, the tumor epitope is an epitope of an antigen selected from the group consisting of CMV, EGFRvIII, EphA2, gp100, Her2/neu, IL-13Ra2, survivin, hTert, TRP-2, MAGE-AL MAGE-A3, YKL-40, brevican, neuroligin 4 and PTPRzl, EpCAM, HER-2, MUC-1, TOMM34, RNF 43, KOC1, VEGFR, βhCG, CEA, TGFβR2, p53, KRas, OGT, CASP5, COA-1, MAGE, SART and IL13Ralpha2, MART-1, tyrosinase, and NY-ESO-1. The remainder of the features and example feature of the variables of the method are as described above with respect to the first through fourth aspects of the third embodiment.

In a sixth aspect of the third embodiment, the recombinant protein is the STINGΔTM protein having an amino acid sequence selected from SEQ ID Nos: 1 and 2. For example, the recombinant protein is the STINGΔTM protein having an amino acid sequence of SEQ ID NO: 1. Alternatively, the recombinant protein is the STINGΔTM protein having an amino acid sequence of SEQ ID NO: 2. The remainder of the features and example feature of the variables of the method are as described above with respect to the first through fifth aspects of the third embodiment.

In a seventh aspect of the third embodiment, the recombinant protein is the STINGΔTM protein having an amino acid sequence selected from SEQ ID NOs: 1 and 2; and the agonist of STING protein is 2'3'-cGAMP. For example, the recombinant protein is the STINGΔTM protein having an amino acid sequence of SEQ ID NO: 1. Alternatively, the recombinant protein is the STINGΔTM protein having an amino acid sequence of SEQ ID NO: 2.

In an eighth aspect of the third embodiment, the cancer is selected from skin cancer, colon cancer, breast cancer, lung cancer, pancreatic cancer, oral cancer, brain cancer, leukemia, lymphoma. For example, the cancer is selected from melanoma, metastatic breast cancer, glioma, T cell lymphoma, acute myeloid leukemia, or non-small cell lung cancer. For example, wherein the cancer is melanoma or colon cancer. The remainder of the features and example feature of the variables of the method are as described above with respect to the first through seventh aspects of the third embodiment.

In an ninth aspect of the third embodiment, the method further comprises administering to the subject an effective amount of an additional pharmaceutically active agent. For example, the additional agent is a checkpoint inhibitor, such as an anti-PD-1 antibody, anti-PD-L1 antibody, or an anti-CTLA4 antibody. The remainder of the features and example feature of the variables of the method are as described above with respect to the first through eighth aspects of the third embodiment.

In a tenth aspect of the third embodiment, the subject has a STING allele selected from a wild type STING allele, a HAQ STING allele, an AQ STING allele, or a REF STING allele. The remainder of the features and example feature of the variables of the method are as described above with respect to the first through ninth aspects of the third embodiment.

In the fourth embodiment, the present invention is a vaccine composition, comprising a non-covalent complex and a pharmaceutically acceptable carrier, wherein the non-covalent complex comprises: a recombinant protein comprising a STINGΔTM protein and a tumor epitope; and an agonist of a STING protein or a pharmaceutically acceptable salt thereof.

In a first aspect of the fourth embodiment, the complex comprises a tetramer of the recombinant protein.

In a second aspect of the fourth embodiment, the STINGΔTM protein is a human STINGΔTM protein. For example, the STINGΔTM protein has an amino acid sequence selected from SEQ ID NOs: 1-10. For example, the STINGΔTM protein has an amino acid sequence selected from SEQ ID NOs: 1 or 2, e.g., SEQ ID NO. 1. The remainder of the features and example feature of the variables of the vaccine composition are as described above with respect to the first aspect of the fourth embodiment.

In a third aspect of the fourth embodiment, the STING protein agonist is a CDN. For example, the CDN is selected from cdiGMP, cdiAMP, 2'3'-cGAMP, 3'3'-cGAMP, or a compound represented by one of the following structural formulas:

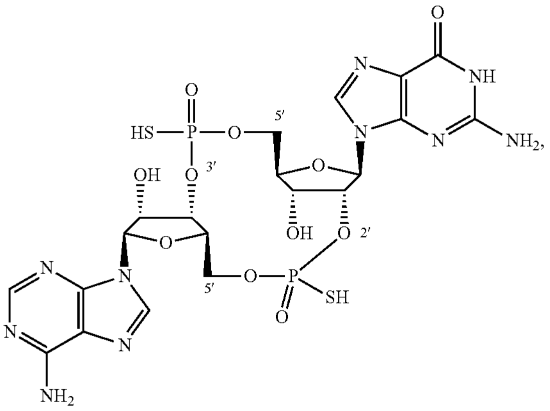

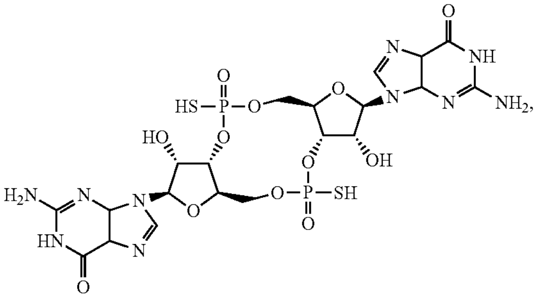

and

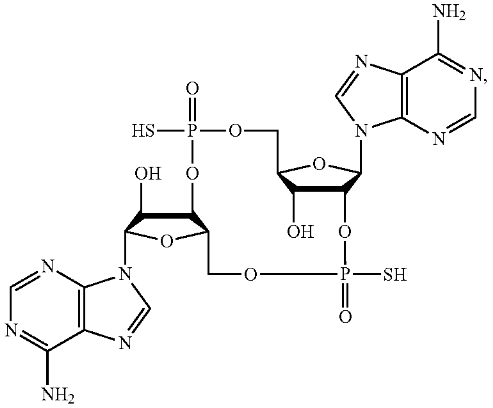

or a pharmaceutically acceptable salt thereof. For example, the CDN is selected from cdiGMP, cdiAMP, 3'3'-cGAMP, or a compound represented by one of the following structural formulas:

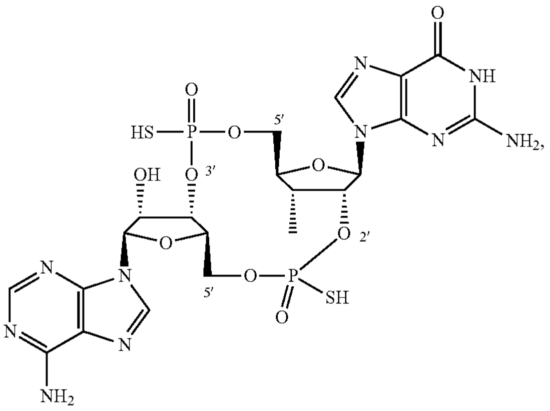

-continued

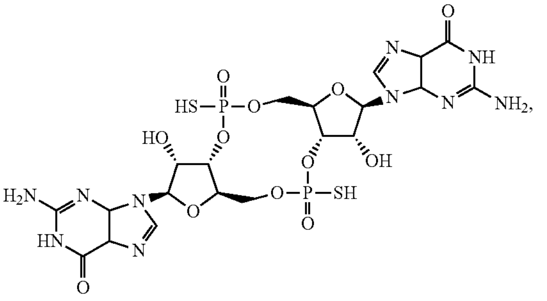

and

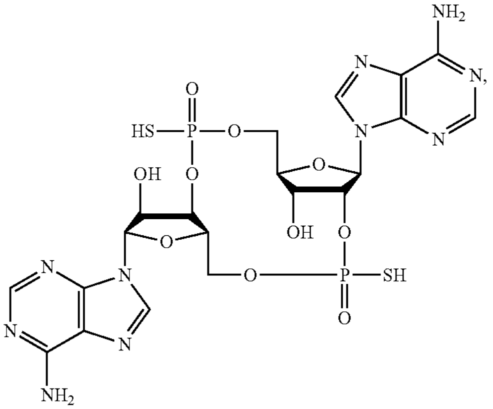

or a pharmaceutically acceptable salt thereof. For example, the CDN is 2'3'-cGAMP. Additionally or alternatively, the CDN is cdiGMP. The remainder of the features and example feature of the variables of the vaccine composition are as described above with respect to the first and second aspects of the fourth embodiment.

In a fourth aspect of the fourth embodiment, the STING protein agonist is a compound represented by one of the following structural formulas:

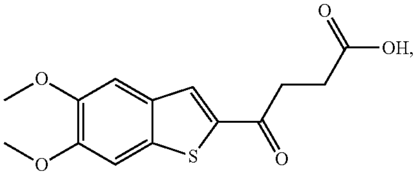

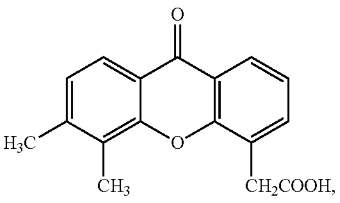

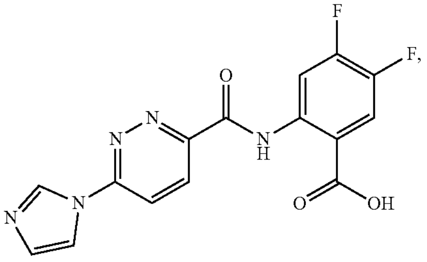

-continued

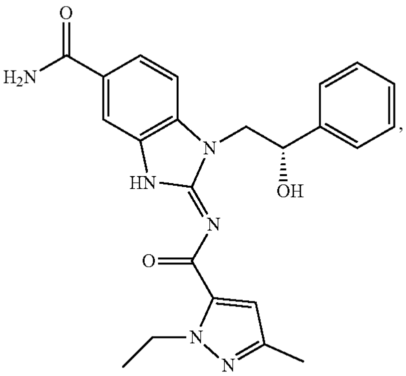

,

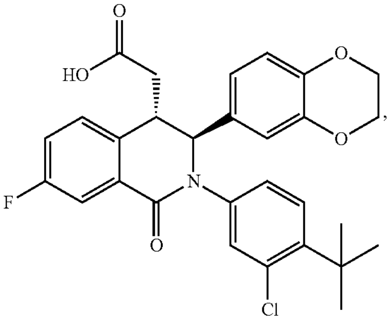

,

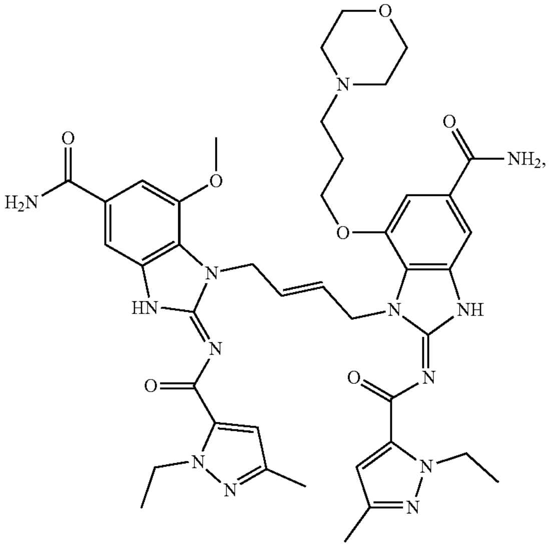

,

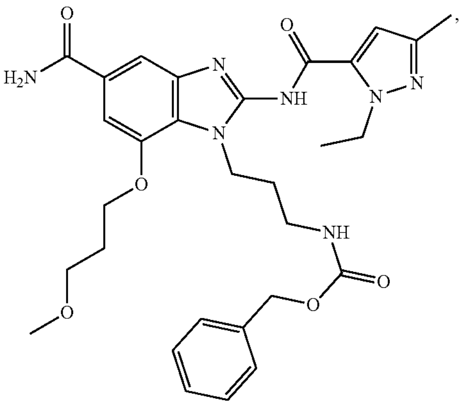

, and

-continued

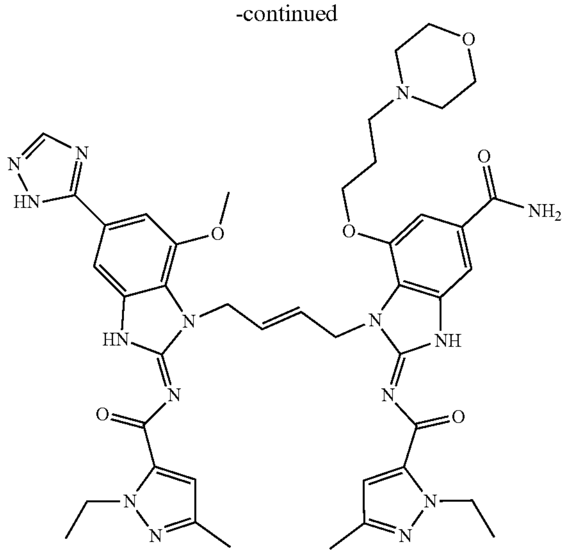

or a pharmaceutically acceptable salt thereof. The remainder of the features and example feature of the variables of the vaccine composition are as described above with respect to the first and second aspects of the fourth embodiment.

In a fifth aspect of the fourth embodiment, tumor epitope is attached to the N-terminus of STINGΔTM. Alternatively, the tumor epitope is attached to the C-terminus of STINGΔTM. For example, the tumor epitope is an epitope of an antigen selected from the group consisting of CMV, EGFRvIII, EphA2, gp100, Her2/neu, IL-13Ra2, survivin, hTert, TRP-2, MAGE-A1, MAGE-A3, YKL-40, brevican, neuroligin 4 and PTPRzl, EpCAM, HER-2, MUC-1, TOMM34, RNF 43, KOC1, VEGFR, βhCG, CEA, TGFβR2, p53, KRas, OGT, CASP5, COA-1, MAGE, SART and IL13Ralpha2, MART-1, tyrosinase, and NY-ESO-1. The remainder of the features and example feature of the variables of the vaccine composition are as described above with respect to the first through fourth aspects of the fourth embodiment.

In a sixth aspect of the fourth embodiment, the STINGΔTM protein has an amino acid sequence selected from SEQ ID NOs: 1 and 2; and the agonist of STING protein is 2'3'-cGAMP. For example, the STINGΔTM protein has an amino acid sequence of SEQ ID NO: 1. Alternatively, the STINGΔTM protein has an amino acid sequence of SEQ ID NO: 2.

In a seventh aspect of the fourth embodiment, the vaccine is a therapeutic vaccine. The remainder of the features and example feature of the variables of the vaccine composition are as described above with respect to the first through sixth aspects of the fourth embodiment.

In an eighth aspect of the fourth embodiment, the vaccine is a prophylactic vaccine. The remainder of the features and example feature of the variables of the vaccine composition are as described above with respect to the first through sixth aspects of the fourth embodiment.

In the fifth embodiment, the present invention is a method of initiating, enhancing or prolonging an immune response in a subject, comprising administering the subject an effective amount of the vaccine composition described herein with respect to the fourth embodiment and various aspects thereof.

In a first aspect of the fifth embodiment, the subject has cancer. For example, the cancer is selected from skin cancer, colon cancer, breast cancer, lung cancer, pancreatic cancer, oral cancer, brain cancer, leukemia, lymphoma. For example, the cancer is selected from melanoma, metastatic breast cancer, glioma, T cell lymphoma, acute myeloid leukemia, or non-small cell lung cancer. For example, wherein the cancer is melanoma or colon cancer.

In a second aspect of the fifth embodiment, the method further comprises administering to the subject an effective amount of an additional pharmaceutically active agent. For example, the additional agent is a checkpoint inhibitor, such as an anti-PD-1 antibody, anti-PD-L1 antibody, or an anti-CTLA4 antibody. The remainder of the features and example feature of the variables of the method are as described above with respect to the first aspect of the fifth embodiment.

In a second aspect of the fifth embodiment, the subject has a STING allele selected from a wild type STING allele, a HAQ STING allele, an AQ STING allele, or a REF STING allele. The remainder of the features and example feature of the variables of the method are as described above with respect to the first and second aspects of the fifth embodiment.

In the sixth embodiment, the present invention is a kit, comprising: a pharmaceutical composition described herein with respect to the second embodiment and various aspects thereof or a vaccine composition described herein with respect to the fourth embodiment and various aspects thereof; and a pharmaceutical composition comprising an additional pharmaceutically active agent.

In a first aspect of the sixth embodiment, the additional agent is a checkpoint inhibitor, such as an anti-PD-1 antibody, anti-PD-L1 antibody, or an anti-CTLA4 antibody.

EXAMPLES

Example 1. Studies of STINGΔTM/CDN Complexes

STINGΔTM Protein purification: The STINGΔTM protein of mouse (138-378aa) and human (139-379aa) were synthesized by gblock (IDT) and cloned into pSH200 plasmid (a gift from Prof. Xiling Shen at Duke University) via NcoI and NotI. Mutants were created by site-specific mutagenesis based on the plasmids encoding for STINGΔTM (primers shown in FIG. 28). His-tagged STINGΔTM protein was expressed in DE3 *E. coli* (mSTINGΔTM in BL21 DE3, hSTINGΔTM in RosettaTM DE3), cultured at 37° C. till OD600 reaches 0.4, and then induced with 0.5 mM IPTG at 18° C. overnight. After induction cells were centrifuged and lysed at room temperature for 20 min in protein binding buffer (50 mM sodium phosphate, 0.5 M NaCl, 10 mM imidazole) with 1% Triton-100 and 1 mg/mL lysozyme and sonicated at 18 W (with 3 s on, 5 s off intervals) for a total of 5 min on ice. Cell lysate was then centrifuged at 14000 g, 4° C. for 30 min and incubated with Cobalt beads (HisPurTM Cobalt Resin, ThermoFisher, 89964) followed by washing (50 mM sodium phosphate, 0.5 M NaCl, 10 mM imidazole, 0.1% Triton-114), elution (50 mM sodium phosphate, 0.5 M NaCl, 150 mM imidazole) and desalting (buffer exchange to 20 mM HEPES, 150 mM NaCl, 10% glycerol, and 1 mM DTT). Protein concentration was determined by BCA assay and protein purity was verified by SDS-PAGE and FPLC.

FPLC characterization of cGAMP-STINGΔTM complex: The ribonucleoprotein complexes of cGAMP-STINGΔTM (and R238A/Y240A, Q272A/A276Q mutants) were analyzed using an AKTA Pure FPLC. 300 μg protein in 0.5 mL PBS with various molar ratios of cGAMP was first mixed and incubated at room temperature for 30 min. The sample was injected into 10 mL superloop, then loaded onto a SuperdexTM 200 Increase 10/300 GL column (column volume 23.56 mL), followed by isocratic elution of 1.25 column volume with PBS at 1 mL/min flow rate. The protein concentration was monitored with OD 280. A fraction collector was used to collect 0.5 mL fractions for SDS-PAGE analyses.

Cell culture: HEK293T cells were obtained from American Type Culture Collection (ATCC, Rockville, Md., USA) and cultured in DMEM (Invitrogen) with 10% FBS and 1% penicillin/streptomycin. NF-κB Reporter Raw 264.7 (Raw-BlueTM cells) were obtained from Invivogen and cultured in DMEM with 10% heat inactivated FBS and 1% penicillin/streptomycin. All cell lines were used at low passage number and tested negative for Mycoplasma contamination.

In vitro STING signaling activation assays: RAW-BlueTM cells were seeded in 96-well plates at 3×105 cells/mL in 100 μL DMEM with 10% heat inactivated FBS and 1% penicillin/streptomycin per well. After 24 h incubation, 5 μg mSTING ΔTM protein (or mutants) with 0.125 μg cGAMP premixed and equilibrated in 20 μL OptiMEM media was added to each well and incubated overnight. After incubation, 20 μL of the induced RAW-BlueTM cell supernatant was added to 180 μL QUANTI-BlueTM solution per well of a 96-well plate. The plate was incubated in 37° C. for 6-10 h until a visible color difference was observed. IFN-SEAP activity was then determined by the absorbance at 635 nm with a spectrophotometer.

For the HEK293T cells, a reporter derivative from this cell line was first generated by transfecting pGL4.45[luc2P/ISRE/Hygro] (Promega company) and stably selected in 200 μg/ml hydromycin. The pGL4.45[luc2P/ISRE/Hygro] vector contains five copies of an interferon-stimulated response element (ISRE) that drives transcription of the luciferase reporter gene luc2P (Photinus pyralis). luc2p is a synthetically-derived luciferase sequence with humanized codon optimization that is designed for high expression and reduced anomalous transcription. The luc2P gene contains hPEST, a protein destabilization sequence, which allows luc2P protein levels to respond more quickly than those of luc2p to induction of transcription. The cells was seeded in 6-well plates at 3×105 cells/mL in 2.5 mL DMEM with 10% FBS and 1% penicillin/streptomycin. After overnight incubation, the cells were transiently transfected with plasmids (a gift from Dr. Lei Jin, University of Florida) encoding for expression of full length hSTING (1-379aa) WT, HAQ, S366A, and L374A, plus the transmembrane domain deficient hSTING (139-379aa). Commercial transfection reagent TransIT-X2TM was used to help transfection (2 μg pDNA mixed with 4 μL TransIT-X2TM in 250 μL Opti-MEM media for each 6-well). The following day, cells were redistributed into 96-well plates at a seeding density of 3×105 cells/mL in 100 μL media per well to be treated with cGAMP-STINGΔTM after 24 h incubation (2 μg protein with or without 0.05 μg cyclic dinucleotides cGAMP, cGAM(PS)2, or cdi-GMP per well, with the help of 4 μL TransIT-X2TM). For assays with chemical inhibitors, HEK293T cells were treated with TBK1 inhibitor MRT67307 (Invivogen, catalog inh-mrt, 6 h prior to cGAMP-STINGΔTM treatment), chloroquine (Enzo, catalog 51005-CLQ, 2 h prior to cGAMP-STINGΔTM treatment), Bafilomycin A1 (Invivogen, catalog tlrl-baf1, 2 h prior to cGAMP-STINGΔTM treatment), and Brefeldin A (Invivogen, catalog inh-bfa, 2 h prior to cGAMP-STINGΔTM treatment). Transfected cells were also harvested for western blotting.

Western blotting: Cells were washed with PBS and collected in T-PER Tissue Protein Extraction Reagent (30 μL per million cells) with HaltTM Protease and Phosphatase Inhibitor Cocktail (ThermoFisher, #78442). The cells were lysed at 4° C. for 30 min and centrifuged at 14,000 g for 10 min. The protein concentration in supernatant was determined via BCA assay and SDS-PAGE samples were prepared as 50 μg total protein in 30 μL SDS-PAGE loading buffer. Anti-TBK1 (Cell Signaling, #3504), anti-STING (Novus Bio, NBP2-24683), anti-beta actin (Cell signaling), and anti-tubulin (Cell signaling).

Quantification of STING signaling-associated protein expression by qPCR: Total RNA was extracted by RNeasy micro kit (Qiagen, 74004) and reverse transcribed to cDNA with reverse transcription kit (ThermoFisher, 4374966). cDNA was amplified and quantified by a Roche LightCycler 480 real-time PCR system. qPCR primers used for detection are shown in FIG. 28. All sequences are DNA artificial sequences; F stands for forward primer and R stands for reverse.

Immunocytochemistry: Transfection and immune staining were performed in Millicell® EZ chamber slides (Millipore Sigma, Temecula, Calif., USA). Cells were fixed by 4% formaldehyde in PBS for 15 min, permeabilized by 0.4% Triton X-100 on ice for 10 min, and stained with rabbit anti-STING antibody (1:400, Novus bio, NBP2-24683) overnight at 4° C. or in the case of cells transfected with FLAG-STINGΔTM, stained with Cy3-conjugated anti-FLAG antibody (Sigma, A9594). For recombinant STING, proteins were conjugated with NHS-Alexa 488 (Thermofisher). Other primary antibodies used are anti-TBK1 (Abcam, ab235253), anti-LAMP1 (Cell Signaling, 9091S), and anti-EEA1 (Cell Signaling, 3288S). After washing with PBS containing 0.05% Tween-20, cells were stained with secondary antibodies including Alexa 568-conjugated goat anti-rabbit IgG antibody (Thermofisher, #A-11011), and Alexa 488-conjugated donkey anti-rabbit IgG antibody (Thermofisher, #A-32790). Nuclei were counter stained with DAPI and Golgi apparatus were stained with Golgi-ID green detection kit (Enzo, 51028-GG). Cells were imaged with an Inverted Olympus IX83 microscope equipped with a Hamamatsu ImagEM high sensitivity camera at the Swanson Biotechnology Center (MIT).

Mice and immunizations: C56BL/6 (B6), C57BL/6-Tg (TcraTcrb)1100Mjb/J (OT-1) mice were purchased from The Jackson Laboratory and housed in the MIT Animal Facility. All mouse studies were performed according to the protocols approved by the MIT Division of Comparative Medicine (MIT DCM). Experiments were conducted using female mice of 8-12 weeks old. For immunizations performed with tail base injections, 50 μL injected per side of the tail, 100 μL dosage total in PBS. Blood was collected via cheek bleeding, 100-150 μL blood each time collected in 5 μL of 0.5 M EDTA at pH 8. For the humoral response experiments, B6 mice were immunized with 10 μg OVA alone, or OVA mixed with 2.5 μg cGAMP and/or 100 μg mSTING ATM or both on days 0 and 7. Sera were collected on a biweekly basis starting from day 14 for ELISA analyses of anti-OVA total IgG level. For the tetramer, intracellular cytokine staining, and B16 prophylactic study, groups of B6 mice received 50 μg OVA, or OVA mixed with lug cGAMP or plus 40 mSTING (or S365A) ATM protein on days 0 and 7. On day 14 PBMCs were collected for tetramer and intracellular cytokine staining. For the memory T cell precursor study, B6 mice were immunized with the same dosage at day 0 as prime and day 14 as boost. On day 21 blood was collected via cheek bleeding, draining lymph node (dLN) inguinal lymph nodes and spleens were harvested. Blood was processed in the same way to obtain PBMCs. For the in vivo dendritic cell activation study, B6 mice were immunized with the same dosage at day 0 and sacrificed at day 1.5 to harvest for inguinal lymph nodes. For the systemic toxicity study, groups of B6 mice were bled before and 2 h after tail base injections of 1 μg cGAMP mixed with 24, TransIT-X2TM or 40 μg mSTING dissolved in 100 μL PBS, or PBS only as control. ATM protein PBMCs of OT-1 mice were collected as a positive control for SIINFEKL-specific T cell activation. On day 21 mice were inoculated with 1 million B16-OVA cells s.c. in the right hind flank. For the MC38 treatment study, groups of B6 mice were inoculated with 1 million MC38 cells s.c. in the right hind flank on day 0, then treated weekly with 100 μg mSTING ATM protein (or S365A, R238A/Y240A) with or without 2.5 μg cGAMP starting on day 7 for 5 times.

ELISA, intracellular cytokine staining and tetramer staining: Blood collected were centrifuged at 500 g for 3 min. Sera were removed for ELISA detection of IL-6 (R&D, catalog DY406), TNF-α (R&D, catalog DY410), and OVA-specific antibody levels. ELISA assays were made in house by coating high-binding ELISA plate (Corning) with 10 μg/ml protein (OVA) or capture antibody for mouse IL-6 and TNF-α in 50 mM sodium bicarbonate buffer (pH 9.6) overnight. On the next day, wells were washed with PBS followed by blocking with 1% BSA in PBS at RT for an hour. Diluted sera were added into wells and incubated at RT for two hours. Detection antibodies for IL-6 and TNF-α, or anti-mouse IgG, HRP-linked Antibody (Cell signaling, catalog 7076) was diluted in 1% BSA in PBS at 1:5000. Samples were washed extensively with 1×PBS containing 0.05% Tween 20 in between. TMB (Biolegend) was used as the substrate, and reaction was quenched by HCl. Plates were measured at OD 450 nm.

The blood cells pellet was lysed with red blood cell lysing buffer hybrid-max (Sigma, R7757) and washed with PBS to obtain PBMCs. Inguinal lymph nodes and spleens were first homogenized with frosted microscope slides and filtered through cell strainers in FACS buffer. Lymphocytes were then ready for staining. Splenocytes were processed with red blood cell lysis buffer before staining. For intracellular cytokine staining, the PBMCs were first stimulated by resuspending in 400 μL of RPMI media with 10% FBS, 0.1 mM of non-essential amino acids, 50 μM β-mercaptoethanol, 1% penicillin/streptomycin, 1 μg/mL SIINFEKL peptide (Anaspec Inc, AS-60193-1) and BD GolgiStopTM (4 μL of BD GolgiStopTM for every 6 mL) and incubated at 37° C. for 4 h. The PBMCs were then treated with Fc-blocker (anti-mouse CD16/CD32 monoclonal antibodies) followed by viability staining (Live/dead fixable aqua stain, Thermo, L34965) and surface staining with anti-CD8 antibodies (Biolegend, 100707, clone 53-6.7). After the surface staining, the PBMCs were then fixed, permeabilized, and stained with anti-mouse IFN-γ, (biolegend, 505825, clone: XMG1.2) and anti-mouse TNF-α (biolegend, 506107, clone: TN3-19.12) antibodies then analyzed on a BD Canto flow cytometer. For tetramer staining, the PBMCs obtained from blood were likewise directly treated with Fc-blocker, viability staining, surface staining with anti-CD8 and H-2Kb/SIINFEKL tetramer then fixed with formaldehyde. For the memory T cell precursor study, PBMCs, lymphocytes, and splenocytes were treated with Fc-blocker, viability staining, surface staining with anti-CD8, H-2Kb/SIINFEKL tetramer, anti-mouse CD27 (biolegend, 124212, clone: LG.3A10), anti-mouse KLRG1 (biolegend, 138416, clone: 2F1/KLRG1), and anti-mouse CD62L (biolegend, 104436, clone: MEL-14). For the dendritic cell maturation study, lymphocytes were treated with Fc-blocker, viability staining, surface staining with anti-mouse CD11c (biolegend, 117310, clone: N418) and anti-mouse MHC class II (biolegend, 107606, clone: M5/114.15.2). Stained cells were then washed and analyzed on a BD Celesta and Fortessa flow cytometer.

In vivo imaging: Balb/c mice tail base injected (on both sides of the tail) with Cy7-NHS ester labelled STINGΔTM—cGAMP complex, Cy7 labelled STINGΔTM and Cy7 labelled cGAMP were imaged under isoflurane anesthesia with Xenogen IVIS system. Acquisition and analysis of images were performed with Living Image software (Xenogen).

Statistical analysis: All statistical analysis were performed using GraphPad Prism 5.03 (San Diego, Calif., USA). Data were analyzed with one-way ANOVA followed by Student's t test for statistical significance.

Mice treated with CDN/STINGΔTM: C56BL/6 (B6) mice were purchased from The Jackson Laboratory and housed in the MIT Animal Facility. All mouse studies were performed according to the protocols approved by the MIT Division of Comparative Medicine (MIT DCM). Experiments were conducted using female mice of 8-12 weeks old. Groups of B6 mice (N=5) were inoculated with 1 million MC38 cells in 100 μL subcutaneously in the right hind flank on day 0, then treated with intratumoral injection of 100 μg mSTINGΔTM protein with or without 2.5 μg CDN (cGAMP or cdiGMP), or with CDN only, starting on day 5 for 3 times every week (i.e. on day 5, day 12, and day 19). Tumor size and survival was monitored. The tumor volume was measured with a caliper and estimated as (length×width^2)/2, where length is the largest tumor diameter and width is the corresponding perpendicular diameter. Overall, groups treated with CDN/mSTINGΔTM showed the least tumor burden and most prolonged survival compared with the control groups. (FIGS. 41-44).

Example 2. Studies of SIINFEKL-STINGΔTM and SIINFEKL-STINGΔTM/CDN Complexes

Protein expression and purification: Model peptide vaccine GLEQLESIINFEKLTEWTSS from chicken ovalbumin amino acids 252-272 was fused to the N-terminus of mouse serum albumin (MSA) and both the N- and C-terminus of STINGΔTM protein (amino acids 138-378 of mouse STING or 139-379 of human STING) and cloned into pSH200 backbone via NcoI and NotI restriction enzyme sites. A hexameric histidine tag was placed at the N-terminus of all proteins for purification. Site-specific mutagenesis was applied to generate mutant proteins such as SIINFEKL-mSTINGΔTM R237A\Y239A and S365A. DE3 *Escherichia coli* (*E. coli*) was used to express the peptide-fused STINGΔTM proteins, BL21 DE3 was used for mouse STINGΔTM and Rosetta DE3 was used for human STINGΔTM and MSA. 1L of *E. coli* was cultured in Luria-Bertani (LB) broth (with antibiotics 100 mg/mL ampicillin for BL21 DE3, 100 mg/mL ampicillin and 35 mg/mL chloramphenicol for Rosetta DE3) at 37° C., 220 rpm till OD600 reaches 0.4. Isopropyl-β-D-thiogalactopyranoside (IPTG) was added to 0.5 mM working concentration for induction at 20° C., 220 rpm overnight. After induction, the bacteria culture was centrifuged to collect the pellet, which was then washed with phosphate buffer saline (PBS), re-suspended in protein binding buffer (50 mM sodium phosphate, 0.5 M NaCl, and 10 mM imidazole) and lysed with 1 mg/mL lysozyme, 1% Triton X-100, and 1 mM phenylmethylsulfonyl fluoride (PMSF) at room temperature for 20 min. A probe sonicator was then used to further disrupt the cells on ice water at 18 W with 3-sec on and 5-sec off intervals for a total of 5 min. The cell lysate was then centrifuged, and the supernatant was incubated with cobalt beads for 1 hr followed by two washing steps with 0.1% Triton-114 protein binding buffer for endotoxin removal. The cobalt beads were then loaded onto gravity flow columns (Poly-Prep chromatography column, Bio-Rad, 7311550) and eluted with 1.5 mL protein elution buffer (50 mM sodium phosphate, 0.5 M NaCl, and 150 mM imidazole). Protein elution was then loaded onto size exclusion desalting columns (Zeba™ Spin Desalting Columns 40k MWCO 10 ml, Thermo Fisher Scientific, 87772) and buffer exchanged to protein storage buffer (20 mM HEPES, 150 NaCl, 10% glycerol, and 1 mM 1,4-Dithiothreitol). Protein concentration was determined with DC™ Protein Assay Kit I (Biorad 5000111) and protein purity was verified with SDS-PAGE.

FPLC characterization of cGAMP-binding induced SIINFEKL-STINGΔTM tetramerization: AKTA pure fast protein liquid chromatography (FPLC) with Superdex 200 Increase 10/300 GL size exclusion column was used to analyze the interaction between cGAMP and SIINFEKL-STINGΔTM proteins. cGAMP concentration was confirmed using Nanodrop. For each run, 300 μg of protein with different molar ratios of cGAMP was first mixed in 500 μL PBS and equilibrated at room temperature for 30 min. The sample was then loaded onto the column followed by isocratic elution of PBS at 1 mL/min flow rate. The protein concentration was monitored with OD280. A protein standard mix for size exclusion chromatography was used to calibrate FPLC elution time to molecular weight.

Cell culture: HEK293T and RAW264.7 cells were obtained from the American Type Culture Collection (ATCC). DC2.4 cells were obtained from the Rock lab at University of Massachusetts Medical School, MA, USA. RAW-Blue™ ISG cells were obtained from Invivogen. HEK293T and RAW264.7 cells were cultured in Dulbecco's modified Eagle's medium (DMEM) with 10% fetal bovine serum (FBS) and 1% penicillin/streptomycin. For SEAP-IFN assay, RAW-Blue™ ISG cells were cultured in DMEM with 10% heat-inactivated (56° C., 30 min) FBS and 1% penicillin/streptomycin. DC2.4 cells were cultured in Roswell Park Memorial Institute (RPMI) medium with 10% FBS and 1% penicillin/streptomycin. All cells are cultured in a 37° C., 5% CO2 incubator, used at low passage number and tested negative for Mycoplasma contamination.

Western blotting: Cells were first washed with PBS and then collected in T-PER tissue protein extraction reagent (30 μL per million cells) with Halt protease and phosphatase inhibitor cocktail (Thermo Fisher Scientific, 78442) and incubated at 4° C. for 30 min with gentle vortexing. The lysate was then centrifuged, and the supernatant was collected to measure the total protein concentration with DC™ Protein Assay Kit I (Biorad 5000111). 50 μg of total protein was loaded onto each lane of SDS-PAGE and subsequently transferred to nitrocellulose membrane, which was then blocked with 5% w/v non-fat milk (Cell signaling, 9999S) and incubated with primary antibodies mouse anti-α-tubulin (Cell signaling, 3873S), rabbit anti-STING (Cell signaling, 13647S), rabbit anti-IRF3 (Cell signaling, 4302S), rabbit anti-mcGAS (Cell signaling, 31659S), rabbit anti-hcGAS (Cell signaling, 83623S), rabbit anti-TBK1 (Abcam, 235253), and secondary antibodies anti-rabbit HRP (Cell signaling, 7074S) and anti-mouse HRP (Thermo Fisher Scientific, 62-6520).

Detection of in vitro STING activation with luc2p-ISRE reporter in HEK293T cell:

HEK293T-luc2p/ISRE/Hygro cells were seeded in clear bottom flat white (or black) 96-well plates 100 μL per well at a density of $3.5\times10^5$ cells/mL. Following overnight incubation, each well of cells were treated with a mixture of 1 μg of SIINFEKL-STINGΔTM protein, 0.025 μg of cGAMP, and 1 μL of TransIT-X2 in a total volume of 20 μL OptiMEM media. After treated cells had been incubated for 24 hr, a firefly luciferase assay kit (Biotium, 30075-2) was used to determine the luciferase expression following the manufacturer's protocol. Briefly, the medium was aspirated and cells were lysed then mixed with luciferase assay buffer containing 0.2 mg/mL freshly added D-luciferin, followed by plate-reading for bioluminescence.

Detection of in vitro STING activation with mCXCL10 ELISA in RAW264.7 and DC2.4 cells: RAW264.7 or DC2.4 cells were seeded in 96-well plates 100 μL per well at a density of $2\times10^5$ cells/mL. Following overnight incubation, each well of cells was treated with a mixture of 1 μg of SIINFEKL-STINGΔTM protein, 0.025 μg of cGAMP, and 1 μL of TransIT-X2 in a total volume of 20 μL OptiMEM media. For vehicle-free treatment, each well of cells were treated with 5 μg of SIINFEKL-STINGΔTM protein and 0.125 μg of cGAMP in 20 μL OptiMEM media. Treated cells were incubated for 48 hr. ELISA was performed according to the manufacturer's protocol: Mouse CXCL10 ELISA kit (R&D, DY466).

In vivo imaging: SIINFEKL-STINGΔTM and SIINFEKL-MSA proteins were first labeled with Cy7-NHS ester (Lumiprobe, 25020), mixed with cGAMP then injected into the tail base of Balb/c mice. 24 hr post injection, inguinal lymph nodes of the mice were collected and imaged with Xenogen in vivo imaging system (IVIS). Acquisition and analysis of images were performed with Living Image software (Xenogen).

Mice: C57BL/6 (BL/6) and C57BL/6-Tg(TcraTcrb) 1100Mjb/J (OT1) mice were purchased from the Jackson laboratory and housed in the MIT Koch Institute animal facility. All mouse studies were performed according to the protocols approved by the MIT Division of Comparative Medicine Committee on Animal Care (CAC). Immunizations were performed on female BL/6 mice 8 to 12 weeks old. Lymphocytes for ex vivo antigen presentation and flow cytometer $SIINFEKL^+$ CD8+ T cell control were collected from OT1 mice 8 to 12 weeks old.

Ex vivo antigen presentation: DC2.4 cells were seeded in 48-well plates for 200 μL/well with a density of $10^5$ cells/mL. After overnight incubation, each well of cells were treated with 5 μg OVA, 4 μg SIINFEKL-STINGΔTM, 0.1 μg cGAMP mixed in 20 OptiMEM. As a positive control, SIINFEKL peptides were added to the wells at a working concentration of 0.1-1 μg/mL. The following day, OT1 lymphocytes were extracted from OT1 mice inguinal lymph nodes and stained with 1 μM CFSE in PBS at room temperature for 20 min. Fresh FBS was added to 10% to stop the reaction and wash once with PBS. Cells were re-suspended in RPMI with 10 ng/4 IL-2, 50 μM β-mercaptoethanol, and 0.1 mM non-essential amino acids and incubated at 37° C. for 2 hr. OT1 lymphocytes were added to each well to have approximately 1:10 DC to OT1 cells. After three days of co-culture, cells were washed, blocked with Fc-blocker (anti-mouse CD16/32), and stained with anti-CD8-APC antibody. Flow cytometric analysis was performed on a BD FACS Celesta flow cytometer.

Mice immunization and quantification of antigen-specific T cells with intracellular cytokine staining and tetramer staining: Groups of female BL/6 mice were immunized via tail base injection with 40 μg SIINFEKL-STING or 100 μg SIINFEKL-MSA mixed with 1 jag cGAMP along with other control groups on days 0 and 14. On day 21, mice blood was collected by cheek bleeding, followed by lysis of red blood cells (Millipore Sigma, R7757) to obtain peripheral blood mononuclear cells (PBMCs).

For intracellular cytokine staining, PBMCs were first stimulated 1 μg/mL SIINFEKL peptide in RPMI media with 50 μM β-mercaptoethanol, 0.67 μL/mL GolgiStop and 0.1 mM non-essential amino acids and incubated at 37° C. for 4 hr. The PBMCs were then treated with Fc blocker followed by viability staining with LIVE/DEAD fixable aqua stain (Thermo Fisher Scientific, L34965) and staining with anti-CD8 (BioLegend, 100707). The PBMCs were then fixed and permeabilized and stained with anti-IFNγ (BioLegend, 505825) and anti-TNF-α (BioLegend, 506107) antibodies, then analyzed on flow cytometer.

For tetramer staining, PBMCs were similarly blocked with Fc blocker and stained with LIVE/DEAD fixable aqua stain, followed by surface staining with anti-CD8 and H-2Kb/SIINFEKL tetramer, and then analyzed on flow cytometer.

Prophylactic study with B16-OVA melanoma cell line: Groups of BL/6 mice were immunized via tail base injection with 40 μg SIINFEKL-STING with 1 μg cGAMP as well as other control groups on days 0 and 14. On day 21, mice were challenged with 1 million B16-OVA cells inoculated subcutaneously in the right hind flank. The mice survival was monitored, and tumor volumes were measured every two to three days and calculated as $(\text{Length}\times\text{Width}^2)/2$.

Statistical analysis: Statistical analyses were carried out using GraphPad Prism 5. Data were analyzed with one-way analysis of variance (ANOVA) followed by Student's t test for statistical significance.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A non-covalent complex, comprising:

a tetramer of a recombinant protein; and an agonist of a Stimulator of Interferon Gene (STING) protein or a pharmaceutically acceptable salt thereof, wherein the recombinant protein comprises a STING protein lacking a transmembrane domain (STINGΔTM protein) fused to a tumor epitope.

2. The complex of claim 1, wherein the STINGΔTM protein is a human or murine STINGΔTM protein.

3. The complex of claim 2, wherein the STINGATM protein has an amino acid sequence selected from SEQ ID NOs: 1-4, 9-10, 13-16, and 21-22.

4. The complex of claim 1, wherein the STING protein agonist is a cyclic dinucleotide (CDN).

5. The complex of claim 4, wherein the CDN is selected from cyclic dimeric guanosine monophosphate (cdiGMP), cyclic dimeric adenosine monophosphate (cdiAMP), cyclic 2' 3 '-guanosine monophosphate-adenosine monophosphate (2'3'-cGAMP), cyclic 3'3'-guanosine monophosphate-adenosine monophosphate (3'3'-cGAMP), or a compound represented by one of the following structural formulas:

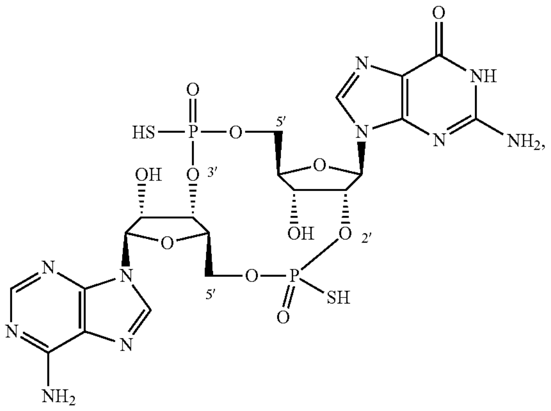

-continued

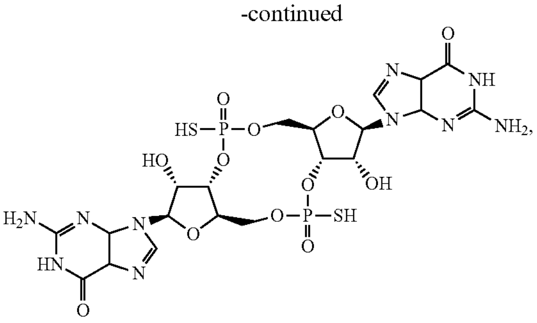

and

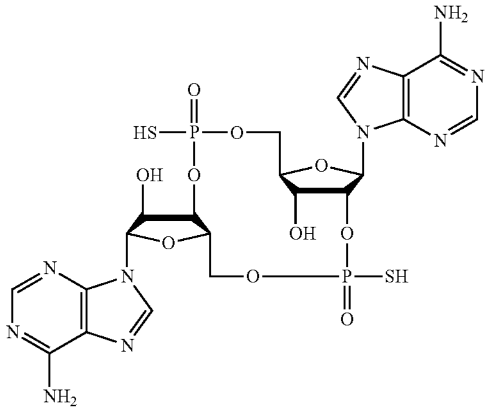

or a pharmaceutically acceptable salt thereof.

6. The complex of claim 5, wherein the CDN is selected from cdiGMP, cdiAMP, 3'3'-cGAMP, or a compound represented by one of the following structural formulas:

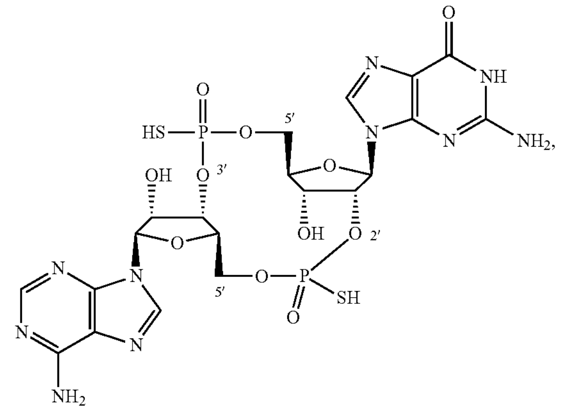
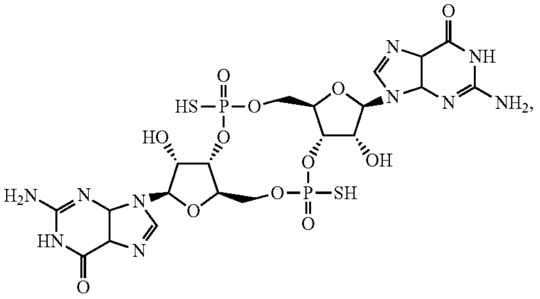
and
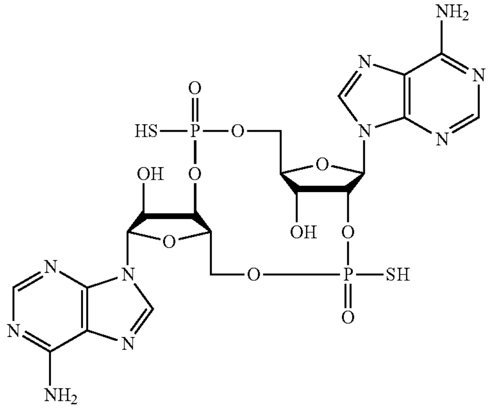
or a pharmaceutically acceptable salt thereof.
7. The complex of claim 1, wherein the STING protein agonist is a compound represented by one of the following structural formulas:
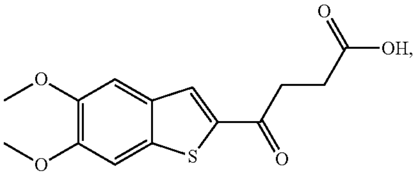
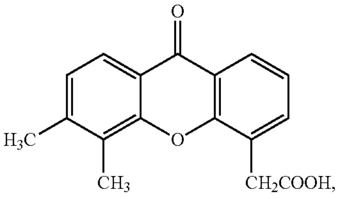
-continued
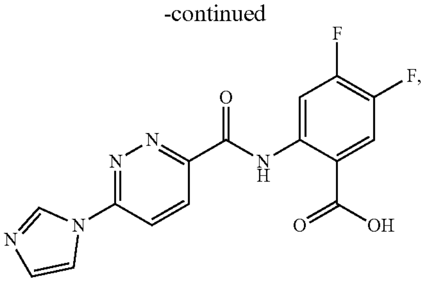
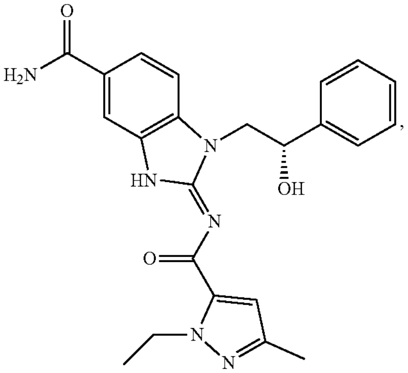
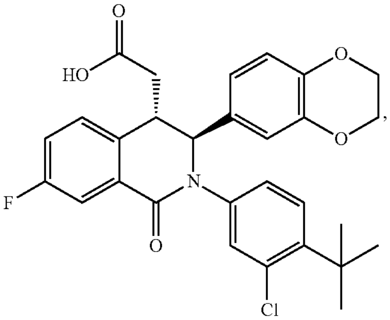
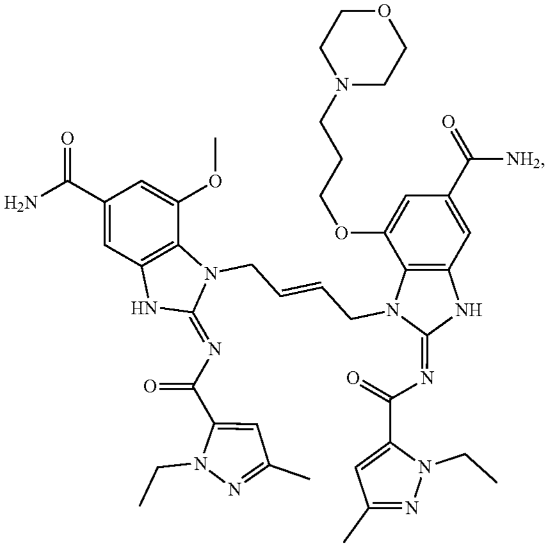

-continued

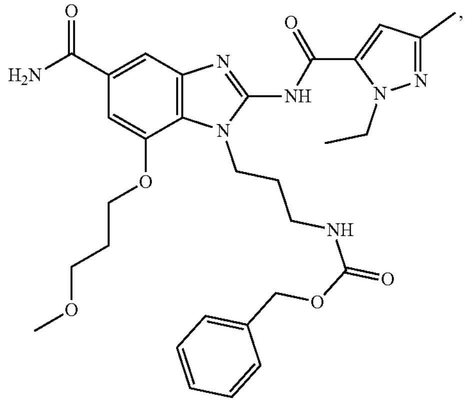

, and

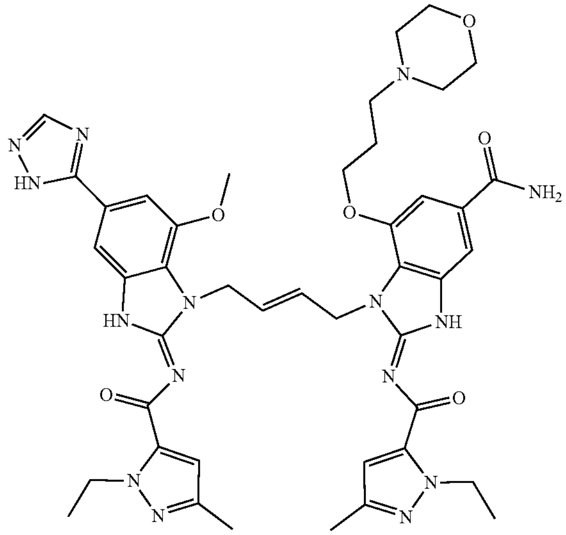

or a pharmaceutically acceptable salt thereof.

8. The complex of claim 1, wherein the tumor epitope is an epitope of an antigen selected from the group consisting of CMV, EGFRvIII, EphA2, gp1OO, Her2/neu, IL-13Ra2, survivin, hTert, TRP-2, MAGE-A1, MAGE-A3, YKL-40, brevican, neuroligin 4 and PTPRzl, EpCAM, HER-2, MUC-1, TOMM34, RNF 43, KOC1, VEGFR, hCG, CEA, TGFpR2. p53, KRas, OGT, CASP5, COA-1, MAGE, SART and IL13Ralpha2, MART-1, tyrosinase, and NY-ESO-1.

9. The complex of claim 1, wherein the recombinant protein is the STINGΔTM protein having an amino acid sequence selected from SEQ ID NOs: 1 and 2; and the agonist of STING protein is 2'3'-cGAMP.

10. A pharmaceutical composition comprising the complex of claim 1 and a pharmaceutically acceptable carrier.

11. A kit, comprising:

a pharmaceutical composition of claim 10; and a pharmaceutical composition comprising an additional pharmaceutically active agent.

12. The kit of claim 11, wherein the additional agent is a checkpoint inhibitor.

13. The kit of claim 12, wherein the checkpoint inhibitor is an anti-PD-1, anti-PD-L1, or an anti-CTLA4 antibody.

14. A vaccine composition, comprising non-covalent complex of claim 1 and a pharmaceutically acceptable carrier.

15. A method of initiating, enhancing or prolonging an immune response in a subject, comprising administering the subject an effective amount of the vaccine composition of claim 14.

16. A method of treating cancer in a subject n need thereof, comprising:

administering to the subject n need thereof an effective amount of the non-covalent complex of claim 1.

* * * * *